United States Patent
Stewart et al.

(10) Patent No.: US 12,297,184 B2
(45) Date of Patent: May 13, 2025

(54) NIRAPARIB SALTS

(71) Applicant: Tesaro, Inc., Waltham, MA (US)

(72) Inventors: Alistair James Stewart, Waltham, MA (US); Yi Wang, Waltham, MA (US); George Wu, Waltham, MA (US); Jianguo Yin, Waltham, MA (US)

(73) Assignee: Tesaro, Inc., Wilmington, DE (US)

( * ) Notice: Subject to any disclaimer, the term of this patent is extended or adjusted under 35 U.S.C. 154(b) by 498 days.

(21) Appl. No.: 17/282,344

(22) PCT Filed: Oct. 3, 2019

(86) PCT No.: PCT/US2019/054534
§ 371 (c)(1),
(2) Date: Apr. 1, 2021

(87) PCT Pub. No.: WO2020/072797
PCT Pub. Date: Apr. 9, 2020

(65) Prior Publication Data
US 2021/0347760 A1     Nov. 11, 2021

Related U.S. Application Data

(60) Provisional application No. 62/740,869, filed on Oct. 3, 2018.

(51) Int. Cl.
C07D 401/02     (2006.01)
A61K 31/435    (2006.01)
A61P 35/00     (2006.01)
C07D 401/10    (2006.01)
C07D 401/12    (2006.01)

(52) U.S. Cl.
CPC ........ C07D 401/12 (2013.01); *C07B 2200/13* (2013.01)

(58) Field of Classification Search
CPC ............... C07D 401/02; C07D 401/10; C07B 2200/13; A61K 31/435; A61P 35/00
See application file for complete search history.

(56) References Cited

U.S. PATENT DOCUMENTS

| | | | |
|---|---|---|---|
| 3,119,742 A | 1/1964 | Heimlich et al. | |
| 3,492,397 A | 1/1970 | Peters et al. | |
| 3,538,214 A | 11/1970 | Polli et al. | |
| 4,060,598 A | 11/1977 | Groppenbacher et al. | |
| 4,173,626 A | 11/1979 | Dempski et al. | |
| 6,100,283 A | 8/2000 | Griffin et al. | |
| 6,310,082 B1 | 10/2001 | Griffin et al. | |
| 6,448,271 B1 | 9/2002 | Lubisch et al. | |
| 6,509,365 B1 | 1/2003 | Lubisch et al. | |
| 6,696,437 B1 | 2/2004 | Lubisch et al. | |
| 6,737,421 B1 | 5/2004 | Lubisch et al. | |
| 7,041,675 B2 | 5/2006 | Lubisch et al. | |
| 7,087,637 B2 | 8/2006 | Grandel et al. | |
| 8,071,623 B2 | 12/2011 | Jones et al. | |
| 8,436,185 B2 | 5/2013 | Foley et al. | |
| 2006/0063926 A1 | 3/2006 | Ma et al. | |
| 2006/0084650 A1 | 4/2006 | Dong et al. | |
| 2006/0229289 A1 | 10/2006 | Zhu et al. | |
| 2006/0229351 A1 | 10/2006 | Zhu et al. | |
| 2007/0112047 A1 | 5/2007 | Penning et al. | |
| 2007/0259937 A1 | 11/2007 | Giranda et al. | |
| 2009/0062268 A1 | 3/2009 | Chu | |
| 2009/0197863 A1 | 8/2009 | Chu | |
| 2009/0275619 A1 | 11/2009 | Boueres et al. | |
| 2010/0286203 A1 | 11/2010 | Foley et al. | |
| 2021/0347758 A1 | 11/2021 | Stewart et al. | |

FOREIGN PATENT DOCUMENTS

| CA | 2349227 | 2/2008 |
|---|---|---|
| CN | 101932572 | 12/2010 |
| CN | 106496187 | 3/2017 |
| CN | 108203404 | 6/2018 |
| CN | 108530425 | 9/2018 |
| EA | 007430 | 10/2006 |
| EP | 0879820 | 12/2001 |
| JP | H083170 | 1/1996 |
| JP | 2003005323 | 1/2003 |
| JP | 2006528187 | 12/2006 |
| JP | 3701964 B | 12/2008 |
| JP | 2011509252 | 3/2011 |
| WO | WO 1997/004771 | 2/1997 |
| WO | WO 1999/059973 | 11/1999 |
| WO | WO 2000/026192 | 5/2000 |
| WO | WO 2000/026193 | 5/2000 |
| WO | WO 2000/029384 | 5/2000 |
| WO | WO 2000/032579 | 6/2000 |
| WO | WO 2000/064878 | 11/2000 |
| WO | WO 2000/068206 | 11/2000 |

(Continued)

OTHER PUBLICATIONS

Gupta et al. "Salts of Therapeutic Agents: Chemical, Physicochemical, and Biological Considerations". Molecules. 23(7): 1719. (Year: 2018).*
Becker et al.("Tumor Heterogeneity in Glioblastomas: From Light Microscopy to Molecular Pathology." Cancers (Basel). Feb. 12, 2021;13(4):761. doi: 10.3390/cancers13040761. PMID: 33673104; PMCID: PMC7918815). (Year: 2021).*
American Brain Tumor Association (ABTA) http://www.abta.org/brain-tumor-information/types-of-tumors/glioma.html?print=t. Accessed Mar. 9, 2016. 3 pages. (Year: 2016).*
Hu et al. (Cell Death Discovery (2023) 9:124 ; https://doi.org/10.1038/s41420-023-01428-8 ). (Year: 2023).*
Cancer Research UK ("Types of cancer." https://www.cancerresearchuk.org/about-cancer/what-is-cancer/how-cancer-starts/ types-of-cancer. Last reviewed: Oct. 9, 2023). (Year: 2023).*
Bastin et al. "Salt Selection and Optimisation Procedures for Pharmaceutical New Chemical Entities", Organic Process Research Development, Jul. 2000, 4(5): 427-435.

(Continued)

*Primary Examiner* — Amanda L. Aguirre
*Assistant Examiner* — Chris E Simmons
(74) *Attorney, Agent, or Firm* — Fish & Richardson P.C.

(57) ABSTRACT

Novel salts of niraparib are provided. Also provided are pharmaceutical compositions comprising those salts, as well as methods and uses pertaining to the same.

15 Claims, 26 Drawing Sheets

(56) References Cited

FOREIGN PATENT DOCUMENTS

| WO | WO 2001/021615 | | 3/2001 | | |
|---|---|---|---|---|---|
| WO | WO 2001/057038 | | 8/2001 | | |
| WO | WO 2001/085687 | | 11/2001 | | |
| WO | WO 2002/068407 | | 9/2002 | | |
| WO | WO 2003/007959 | | 1/2003 | | |
| WO | WO 2003/062234 | | 7/2003 | | |
| WO | WO 2003/106430 | | 12/2003 | | |
| WO | WO 2004/014861 | | 2/2004 | | |
| WO | WO 2004/063155 | | 7/2004 | | |
| WO | WO 2005/047290 | | 5/2005 | | |
| WO | WO 2005/051916 | | 6/2005 | | |
| WO | WO 2005/066136 | | 7/2005 | | |
| WO | WO 2006/003146 | | 1/2006 | | |
| WO | WO 2007/041357 | | 4/2007 | | |
| WO | WO 2007/113596 | | 10/2007 | | |
| WO | WO 2008/084261 | | 7/2008 | | |
| WO | WO 2009/087381 | | 7/2009 | | |
| WO | WO 2014/088983 | | 6/2014 | | |
| WO | WO 2014/179664 | | 11/2014 | | |
| WO | WO 2016/126858 | | 8/2016 | | |
| WO | WO 2016/161270 | | 10/2016 | | |
| WO | WO 2017/218365 | | 12/2017 | | |
| WO | WO 2018/005818 | | 1/2018 | | |
| WO | WO 2018/085468 | | 5/2018 | | |
| WO | WO 2018/085469 | | 5/2018 | | |
| WO | WO 2018/108160 | | 6/2018 | | |
| WO | WO-2018108160 | A1 * | 6/2018 | ......... | A61K 31/4439 |
| WO | WO 2018/122168 | | 7/2018 | | |
| WO | WO 2018/129553 | | 7/2018 | | |
| WO | WO 2018/129559 | | 7/2018 | | |
| WO | WO 2018/018354 | | 10/2018 | | |
| WO | WO 2018/183354 | | 10/2018 | | |
| WO | WO 2018/200517 | | 11/2018 | | |
| WO | WO 2018/201096 | | 11/2018 | | |
| WO | WO 2018/213732 | | 11/2018 | | |

OTHER PUBLICATIONS

Curtin et al., "Therapeutic applications of PARP inhibitors: Anticancer therapy and beyond", Molecular Aspects of Medicine, Dec. 2013, 34(6): 1217-1256.

Gras et al., "Niraparib Hydrochloride", Drugs of the Future, Oct. 1, 2013, 38(10):679-685.

Grever et al., "The National Cancer Institute: Cancer Drug Discovery and Development Program", Seminars in Oncology, Dec. 1992, 19(6):622-638.

Horig et al., "From bench to clinic and back: Perspective on the 1st IQPC Translational Research Conference", Journal of Translational Medicine, Dec. 2004, 2:44-51.

Hughes, "Patent Review of Manufacturing Routes to Recently Approved PARP Inhibitors: Olaparib, Rucaparib, and Niraparib", Organic Process Research & Development, Aug. 2017, 65 pages.

Ison et al., "FDA Approval Summary: Niraparib for the Maintenance Treatment of Patients with Recurrent Ovarian Cancer in Response to Platinum-Based Chemotherapy", Clinical Cancer Research, Sep. 2018, 24(17):4066-4071.

Jones et al., "Discovery of 2-{4-[(3S)-Piperidin-3-yl]phenyl}-2H-indazole-7-carboxamide (MK-4827): A Novel Oral Poly(ADP-ribose)polymerase (PARP) Inhibitor Efficacious in BRCA-1 and—2 Mutant Tumors", Journal of Medicinal Chemistry, Oct. 2009, 52(22):7170-7185.

Kelley et al., "Targeting DNA repair pathways for cancer treatment: what's new?", Future Oncology, May 2014, 10(7):1215-1237.

Lord et al., "Targeted therapy for cancer using PARP inhibitors", Current Opinion in Pharmacology, Aug. 2008, 8:363-369.

Murai et al., "Trapping of PARP1 and PARP2 by Clinical PARP Inhibitors", Cancer Research, 2012, 72:5588-5599.

International Preliminary Report on Patentability in International Application No. PCT/US2019/054533, dated Mar. 23, 2021, 7 pages.

International Preliminary Report on Patentability in International Application No. PCT/US2019/054534, dated Mar. 23, 2021, 7 pages.

International Search Report and Written Opinion in International Application No. PCT/US2019/054533, dated Dec. 6, 2019, 9 pages.

International Search Report and Written Opinion in International Application No. PCT/US2019/054534, dated Dec. 10, 2019, 9 pages.

Rouleau et al., "PARP inhibition: PARP1 and beyond", Nature Reviews/Cancer, Mar. 2010, 10:293-301.

Schafer et al., "Failure is an option: learning from unsuccessful proof-of-concept trials", Drug Discovery Today, Nov. 2008, 13(21/22):913-916.

Thomas et al., "Preclinical selection of a novel poly (ADP-ribose) polymerase inhibitor for clinical trial", Molecular Cancer Research, Mar. 2007, 6(3):945-956.

Thorsell et al., "Structural Basis for Potency and Promiscuity in Poly(ADP-ribose) Polymerase (PARP) and Tankyrase Inhibitors", Journal of Medicinal Chemistry, Dec. 2016, 60:1262-1271.

training.seer.cancer.gov [online], "Cancer Classification", Jul. 2019, retrieved on Sep. 10, 2021, retrieved from URL <https://training.seer.cancer.gov/disease/categories/classification.html>, 3 pages.

Underhill et al., "A review of PARP inhibitors: from bench to bedside", Annals of Oncology Advance Access, Jul. 2010, pp. 1-12.

U.S. Appl. No. 17/282,358, filed Apr. 1, 2021, Alistair James Stewart.

Desai et al., "Epithelial ovarian cancer: An overview," World Journal of Translational Medicine, Dec. 16, 2014, 3(1):1-15.

Hirayama, "Handbook of Preparation of Organic Compound Crystals," 2008, pp. 17-23, 37-40, 45-51, 57-65; 34 pages (with partial English Translation).

Hughes et al., "Patent Review of Manufacturing Routes to Recently Approved PARP Inhibitors: Olaparib, Rucaparib, and Niraparib," Org. Process Res. Dev., Aug. 9, 2017, 21(9):1227-1244.

Pei et al., "Crystalline Form of Niraparib Tosylate," IP.com, Jan. 9, 2018, retrieved from URL: <https://ip.com/IPCOM/000252421>, 8 pages.

Shioji, "Manufacture Technology of Solid Tablet," CMC Publishing Co., Ltd., Jan. 27, 2003, popular edition, pp. 9, 12 and 13; 5 pages (with partial English Translation).

Terol et al., "Analyse du comportement thermique d'une serie de derives camphoriques," Journal of Thermal Analysis, Jul. 1992, 38:1545-1562 (English Abstract Only).

Yang et al., "Polymorphic Drugs (Chinese Edition," People's Medical Publishing House, Oct. 2009, pp. 6, and 24-25; 19 pages (with Machine Translation).

Anderson and Flora, "Preparation of water-soluble compounds through salt formation," Latest Medicinal Chemistry, Second Volume, Translated by Hiroshi Nagase, Japan, Technomic Co., Ltd., Sep. 25, 1999, Chapter 34, pp. 347-365 (Machine Translation Only).

Hashida, "Design and Evaluation of Oral Dosage Formulations," Japan Pharmaceutical Affairs Co., Ltd., Feb. 10, 1995, pp. 76-79 and 171-172 (Machine Translation Only).

Ishida et al., "4-Phenyl-1,2,3,6-tetrahydropyridine, an excellent fragment to improve the potency of PARP-1 inhibitors," Bioorganic & Medicinal Chemistry Letters, Oct. 2005, 15(19):4221-4225.

Parveen et al., "2-nitroimidazol-5-ylmethyl as a potential bioreductively activated prodrug system: reductively triggered release of the PARP inhibitor 5-bromoisoquinolinone," Bioorganic & Medicinal Chemistry Letters, Jul. 19, 1999, 9(14):2031-2036.

Peukert et al., "New inhibitors of poly(ADP-ribose) polymerase (PARP)," Expert Opinion on Therapeutic Patents, 2004, 14(11): 1531-1551.

Berge et al., "Pharmaceutical Salts," Journal of Pharmaceutical Sciences, Jan. 1977, 66(1):1-19.

Brittain, "X-ray Diffraction III: Pharmaceutical Applications," Spectroscopy, Jul. 2001, 16(7):14-18.

Choi et al., "Polymorph Controlling Technology of Active Pharmaceutical Ingredients," NICE (News & Information for Chemical Engineers), 2010, 28(1):38-46 (Machine Translation of Abstract).

* cited by examiner

NIRAPARIB SALTS

CROSS-REFERENCE TO RELATED APPLICATIONS

The present application claims benefit of U.S. Provisional Application No. 62/740,872, filed on Oct. 3, 2018, which is hereby incorporated by reference in its entirety.

FIELD OF THE INVENTION

This disclosure relates to novel salts of niraparib, to pharmaceutical compositions comprising such salts, and to uses of the same.

SUMMARY OF THE INVENTION

Niraparib is the international nonproprietary name for 2-{4-[(3S)-piperidin-3-yl]phenyl}-2H-indazole-7-carboxamide, and it has the following chemical structure

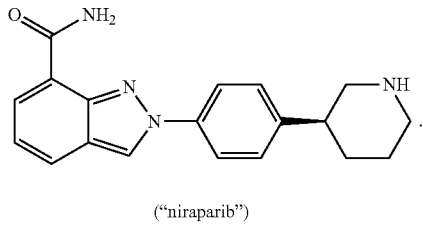 [SMILES: NC(=O)c1cccc2cn(-c3ccc([C@@H]4CCCNC4)cc3)nc12]

("niraparib")

A method for the synthesis of niraparib is given in Jones et al., *J. Med. Chem.*, 52:7170-7185, 2009.

Niraparib is an orally available, selective poly(ADP-ribose) polymerase (PARP) 1 and 2 inhibitor. Niraparib displays PARP-1 and -2 inhibition with an $IC_{50}$ of 3.8 nM and 2.1 nM, respectively, and in a whole cell assay, it inhibits PARP activity ($EC_{50}$=4 nM) and proliferation of cancer cells having mutant BRCA1 and BRCA2 ($CC_{50}$ in the 10-100 nM range) (see Jones et al., *J. Med. Chem.*, 52:7170-7185, 2009). Niraparib also can be useful in treating cancers characterized a deficiency in certain genes involved in the homologous recombination repair (HRR) pathway, including non-BRCA1/2 HRR genes. The activity of niraparib gives it the potential to treat a wide range of conditions, including cancers (especially cancers which are refractory to platinum-based chemotherapy), as well as conditions such as stroke, autoimmune diabetes, neurological diseases, inflammatory diseases, metabolic diseases and cardiovascular diseases.

Recently, niraparib has been approved for the maintenance or treatment of adult patients with recurrent epithelial ovarian, fallopian tube, or primary peritoneal cancer following a complete or partial response to platinum-based chemotherapy. The authorised product (ZEJULA™) is a capsule which contains 100 mg niraparib in the form of its mono-hydrated tosylate salt (niraparib tosylate monohydrate).

As a drug substance, niraparib tosylate monohydrate (i.e. 2-{4-[(3S)-piperidin-3-yl]phenyl}-2H-indazole-7-carboxamide 4-methylbenzenesulfonate hydrate 1:1:1) is a white to off-white, non-hygroscopic, crystalline solid with a low aqueous solubility. Methods for the preparation of niraparib tosylate monohydrate include those described in PCT/US2018/029131.

Despite the commercial success of niraparib tosylate monohydrate, there exists a need to provide further forms of niraparib which have desirable pharmaceutical properties, especially for formulation into solid (e.g. oral) pharmaceutical dosage forms.

Surprisingly, it has now been found that camphorate, mandelate and camsylate salts of niraparib have such desirable properties, including improved aqueous solubility, low hygroscopicity and/or good stability.

Accordingly, in one aspect, the invention provides a 2-{4-[(3S)-piperidin-3-yl]phenyl}-2H-indazole-7-carboxamide (niraparib) salt selected from 2-{4-[(3S)-piperidin-3-yl]phenyl}-2H-indazole-7-carboxamide (niraparib) camphorate, 2-{4-[(3S)-piperidin-3-yl]phenyl}-2H-indazole-7-carboxamide (niraparib) mandelate, and 2-{4-[(3S)-piperidin-3-yl]phenyl}-2H-indazole-7-carboxamide (niraparib) camsylate.

In aspects and embodiments, the invention provides 2-{4-[(3S)-piperidin-3-yl]phenyl}-2H-indazole-7-carboxamide (niraparib) camphorate.

In aspects and embodiments, the invention provides 2-{4-[(3S)-piperidin-3-yl]phenyl}-2H-indazole-7-carboxamide (niraparib) (1R,3S)-(+)-camphorate.

In aspects and embodiments, the invention provides a crystalline form of 2-{4-[(3S)-piperidin-3-yl]phenyl}-2H-indazole-7-carboxamide (niraparib) (1R,3S)-(+)-camphorate.

In aspects and embodiments, the invention provides a crystalline Form 1 of 2-{4-[(3S)-piperidin-3-yl]phenyl}-2H-indazole-7-carboxamide (niraparib) (1R,3S)-(+)-camphorate.

In embodiments, a crystalline form of 2-{4-[(3S)-piperidin-3-yl]phenyl}-2H-indazole-7-carboxamide (niraparib) (1R,3S)-(+)-camphorate is characterized by an X-ray powder diffraction (XRPD) pattern comprising at least three diffraction angles, when measured using Cu K radiation, selected from a group consisting of about 6.5, 11.7, 13.4, 14.1, 14.5, 15.2, 16.2, 17.5, 18.0, 20.0, 20.4, 21.6, 22.3, 22.8, 24.0, 24.5, 26.9, and 27.6 degrees 2θ.

In embodiments, a crystalline form of 2-{4-[(3S)-piperidin-3-yl]phenyl}-2H-indazole-7-carboxamide (niraparib) (1R,3S)-(+)-camphorate is characterized by an X-ray powder diffraction (XRPD) pattern comprising at least three diffraction angles, when measured using Cu K radiation, selected from a group consisting of about 11.7, 13.4, 15.2, 16.2, 17.5, 18.0, 20.0, 20.4, 21.6, 22.8, and 24.0 degrees 2θ.

In embodiments, a crystalline form of 2-{4-[(3S)-piperidin-3-yl]phenyl}-2H-indazole-7-carboxamide (niraparib) (1R,3S)-(+)-camphorate is characterized by an X-ray powder diffraction (XRPD) pattern comprising at least three diffraction angles, when measured using Cu K radiation, selected from a group consisting of about 13.4, 15.2, 16.2, 17.5, 18.0, 20.0, 20.4, 21.6, and 24.0 degrees 2θ.

In embodiments, the crystalline form of 2-{4-[(3S)-piperidin-3-yl]phenyl}-2H-indazole-7-carboxamide (niraparib) (1R,3S)-(+)-camphorate has an X-ray powder diffraction (XRPD) pattern comprising one or more XRPD diffraction angles at 16.2, 17.5, 20.0, 13.4 and/or 15.2±0.2° 2θ.

In embodiments, the crystalline form of 2-{4-[(3S)-piperidin-3-yl]phenyl}-2H-indazole-7-carboxamide (niraparib) (1R,3S)-(+)-camphorate has an XRPD pattern comprising at least two diffraction angles at 16.2, 17.5, 20.0, 13.4 and/or 15.2±0.2° 2θ.

In embodiments, the crystalline form of 2-{4-[(3S)-piperidin-3-yl]phenyl}-2H-indazole-7-carboxamide (niraparib)

(1R,3S)-(+)-camphorate has an XRPD pattern comprising at least three diffraction angles at 16.2, 17.5, 20.0, 13.4 and/or 15.2±0.2° 2θ.

In embodiments, the crystalline form of 2-{4-[(3S)-piperidin-3-yl]phenyl}-2H-indazole-7-carboxamide (niraparib) (1R,3S)-(+)-camphorate has an XRPD pattern comprising at least four diffraction angles at 16.2, 17.5, 20.0 13.4 and/or 15.2±0.2° 2θ.

In embodiments, the crystalline form of 2-{4-[(3S)-piperidin-3-yl]phenyl}-2H-indazole-7-carboxamide (niraparib) (1R,3S)-(+)-camphorate has an XRPD pattern comprising diffraction angles at 16.2, 17.5, 20.0, 13.4 and 15.2±0.2° 2θ.

In embodiments, the crystalline form of 2-{4-[(3S)-piperidin-3-yl]phenyl}-2H-indazole-7-carboxamide (niraparib) (1R,3S)-(+)-camphorate has an XRPD pattern comprising one or more XRPD diffraction angles at 20.4, 21.6, 24.0, 11.7 and/or 18.0±0.2° 2θ.

In embodiments, the crystalline form of 2-{4-[(3S)-piperidin-3-yl]phenyl}-2H-indazole-7-carboxamide (niraparib) (1R,3S)-(+)-camphorate has an XRPD pattern comprising two or more diffraction angles at 20.4, 21.6, 24.0, 11.7 and/or 18.0±0.2° 2θ.

In embodiments, the crystalline form of 2-{4-[(3S)-piperidin-3-yl]phenyl}-2H-indazole-7-carboxamide (niraparib) (1R,3S)-(+)-camphorate has an XRPD pattern comprising three or more diffraction angles at 20.4, 21.6, 24.0, 11.7 and/or 18.0±0.2° 2θ.

In embodiments, the crystalline form of 2-{4-[(3S)-piperidin-3-yl]phenyl}-2H-indazole-7-carboxamide (niraparib) (1R,3S)-(+)-camphorate has an XRPD pattern comprising four or more diffraction angles at 20.4, 21.6, 24.0, 11.7 and/or 18.0±0.2° 2θ.

In embodiments, the crystalline form of 2-{4-[(3S)-piperidin-3-yl]phenyl}-2H-indazole-7-carboxamide (niraparib) (1R,3S)-(+)-camphorate has an XRPD pattern comprising diffraction angles at 20.4, 21.6, 24.0, 11.7 and 18.0±0.2° 2θ.

In embodiments, the crystalline form of 2-{4-[(3S)-piperidin-3-yl]phenyl}-2H-indazole-7-carboxamide (niraparib) (1R,3S)-(+)-camphorate has an XRPD pattern comprising diffraction angles at 16.2, 17.5, 20.0, 13.4, 15.2, 20.4, 21.6, 24.0, 11.7 and 18.0±0.2° 2θ.

In embodiments, the crystalline form of 2-{4-[(3S)-piperidin-3-yl]phenyl}-2H-indazole-7-carboxamide (niraparib) (1R,3S)-(+)-camphorate has an XRPD pattern comprising at least one diffraction angle at 14.8, 18.0, 22.8 and/or 27.6±0.2° 2θ.

In embodiments, the crystalline form of 2-{4-[(3S)-piperidin-3-yl]phenyl}-2H-indazole-7-carboxamide (niraparib) (1R,3S)-(+)-camphorate has an XRPD pattern comprising at least two diffraction angles at 14.8, 18.0, 22.8 and/or 27.6±0.2° 2θ.

In embodiments, the crystalline form of 2-{4-[(3S)-piperidin-3-yl]phenyl}-2H-indazole-7-carboxamide (niraparib) (1R,3S)-(+)-camphorate has an XRPD pattern comprising at least three diffraction angles at 14.8, 18.0, 22.8 and/or 27.6±0.2° 2θ.

In embodiments, the crystalline form of 2-{4-[(3S)-piperidin-3-yl]phenyl}-2H-indazole-7-carboxamide (niraparib) (1R,3S)-(+)-camphorate has an XRPD pattern comprising diffraction angles at 14.8, 18.0, 22.8 and 27.6±0.2° 2θ.

In embodiments, the crystalline form of 2-{4-[(3S)-piperidin-3-yl]phenyl}-2H-indazole-7-carboxamide (niraparib) (1R,3S)-(+)-camphorate has an XRPD pattern comprising one or more diffraction angles at 16.2, 17.5, 20.0, 13.4, 15.2, 20.4, 21.6, 24.0, 11.7, 18.0, 22.8, 18.9, 14.5, 14.1, 14.8, 27.6, 26.9, 6.5, 22.3 and/or 24.5±0.2° 2θ.

In embodiments, the crystalline form of 2-{4-[(3S)-piperidin-3-yl]phenyl}-2H-indazole-7-carboxamide (niraparib) (1R,3S)-(+)-camphorate has an XRPD pattern comprising diffraction angles with the 2θ values (±0.2° 2θ), and optionally also relative intensities, according to the following table:

| Pos. [°2θ] | Rel. Int. [%] |
| --- | --- |
| 6.5 | 15.9 |
| 11.7 | 28.9 |
| 13.4 | 51.5 |
| 14.1 | 21.1 |
| 14.5 | 23.1 |
| 14.8 | 20.6 |
| 15.2 | 48.6 |
| 16.2 | 100 |
| 17.5 | 91.3 |
| 18.0 | 26.6 |
| 18.9 | 25.4 |
| 20.0 | 59.9 |
| 20.4 | 41.2 |
| 21.6 | 35.0 |
| 22.3 | 15.8 |
| 22.8 | 26.0 |
| 24.0 | 30.3 |
| 24.5 | 13.6 |
| 26.9 | 17.4 |
| 27.6 | 17.9 |

In embodiments, the crystalline form of 2-{4-[(3S)-piperidin-3-yl]phenyl}-2H-indazole-7-carboxamide (niraparib) (1R,3S)-(+)-camphorate is characterised by an XRPD pattern substantially in accordance with FIG. 3.

In embodiments, the crystalline form of 2-{4-[(3S)-piperidin-3-yl]phenyl}-2H-indazole-7-carboxamide (niraparib) (1R,3S)-(+)-camphorate is characterised by a melting point of about 260° C. to about 270° C.

In embodiments, the crystalline form of 2-{4-[(3S)-piperidin-3-yl]phenyl}-2H-indazole-7-carboxamide (niraparib) (1R,3S)-(+)-camphorate is characterised by a melting point of about 264° C.

In embodiments, the crystalline form of 2-{4-[(3S)-piperidin-3-yl]phenyl}-2H-indazole-7-carboxamide (niraparib) (1R,3S)-(+)-camphorate is characterised by a DSC thermogram in which the onset of melting (endothermic peak) is about 264° C. and/or wherein the peak minimum is about 268° C.

In embodiments, the crystalline form of 2-{4-[(3S)-piperidin-3-yl]phenyl}-2H-indazole-7-carboxamide (niraparib) (1R,3S)-(+)-camphorate is characterised by a DSC thermogram substantially as shown in FIG. 5.

In embodiments, the crystalline form of 2-{4-[(3S)-piperidin-3-yl]phenyl}-2H-indazole-7-carboxamide (niraparib) (1R,3S)-(+)-camphorate is characterised by an infra-red spectrum comprising peaks at about 3359 $cm^{-1}$, about 1693 $cm^{-1}$ and about 1649 $cm^{-1}$.

In embodiments, the crystalline form of 2-{4-[(3S)-piperidin-3-yl]phenyl}-2H-indazole-7-carboxamide (niraparib) (1R,3S)-(+)-camphorate is characterised by an infra-red spectrum substantially as shown in FIG. 2.

In embodiments, the crystalline form of 2-{4-[(3S)-piperidin-3-yl]phenyl}-2H-indazole-7-carboxamide (niraparib) (1R,3S)-(+)-camphorate is characterised by adsorbing no more than about 0.3% by weight of water up to about 90% relative humidity at about 25° C.

In embodiments, the crystalline form of 2-{4-[(3S)-piperidin-3-yl]phenyl}-2H-indazole-7-carboxamide (niraparib) (1R,3S)-(+)-camphorate is characterised by a GVS thermogram substantially as shown in FIG. 6.

In aspects and embodiments, the invention provides 2-{4-[(3S)-piperidin-3-yl]phenyl}-2H-indazole-7-carboxamide (niraparib) (1S,3R)-(–)-camphorate.

In aspects and embodiments, the invention provides a crystalline form of 2-{4-[(3S)-piperidin-3-yl]phenyl}-2H-indazole-7-carboxamide (niraparib) (1S,3R)-(–)-camphorate.

In aspects and embodiments, the invention provides crystalline Form 1 of 2-{4-[(3S)-piperidin-3-yl]phenyl}-2H-indazole-7-carboxamide (niraparib) (1S,3R)-(–)-camphorate.

In embodiments, the crystalline form of 2-{4-[(3S)-piperidin-3-yl]phenyl}-2H-indazole-7-carboxamide (niraparib) (1S,3R)-(–)-camphorate is characterized by an X-ray powder diffraction (XRPD) pattern comprising at least three diffraction angles, when measuring using Cu K radiation, selected from a group consisting of about 6.5, 11.6, 13.4, 14.0, 14.5, 15.1, 16.2, 17.4, 18.9, 19.9, 20.2, 20.3, 21.5, 21.9, 22.2, 22.3, 23.9, 24.4, and 26.9 degrees 2θ.

In embodiments, the crystalline form of 2-{4-[(3S)-piperidin-3-yl]phenyl}-2H-indazole-7-carboxamide (niraparib) (1S,3R)-(–)-camphorate is characterized by an X-ray powder diffraction (XRPD) pattern comprising at least three diffraction angle, when measuring using Cu K radiation, selected from a group consisting of about 11.6, 13.4, 15.1, 16.2, 17.4, 19.9, 20.2, 20.3, 22.2, 22.3, 24.4, and 26.9 degrees 2θ.

In embodiments, the crystalline form of 2-{4-[(3S)-piperidin-3-yl]phenyl}-2H-indazole-7-carboxamide (niraparib) (1S,3R)-(–)-camphorate is characterized by an X-ray powder diffraction (XRPD) pattern comprising at least three diffraction angle, when measuring using Cu K radiation, selected from a group consisting of about 11.6, 15.1, 16.2, 17.4, 19.9, 20.2, 20.3, 22.3, and 24.4 degrees 2θ.

In embodiments, the crystalline form of 2-{4-[(3S)-piperidin-3-yl]phenyl}-2H-indazole-7-carboxamide (niraparib) (1S,3R)-(–)-camphorate has an XRPD pattern comprising one or more diffraction angles at 20.3, 17.4, 16.2, 15.1 and/or 20.2±0.2° 2θ.

In embodiments, the crystalline form of 2-{4-[(3S)-piperidin-3-yl]phenyl}-2H-indazole-7-carboxamide (niraparib) (1S,3R)-(–)-camphorate has an XRPD pattern comprising at least two diffraction angles at 20.3, 17.4, 16.2, 15.1 and/or 20.2±0.2° 2θ.

In embodiments, the crystalline form of 2-{4-[(3S)-piperidin-3-yl]phenyl}-2H-indazole-7-carboxamide (niraparib) (1S,3R)-(–)-camphorate has an XRPD pattern comprising at least three diffraction angles at 20.3, 17.4, 16.2, 15.1 and/or 20.2±0.2° 2θ.

In embodiments, the crystalline form of 2-{4-[(3S)-piperidin-3-yl]phenyl}-2H-indazole-7-carboxamide (niraparib) (1S,3R)-(–)-camphorate has an XRPD pattern comprising at least four diffraction angles at 20.3, 17.4, 16.2, 15.1 and/or 20.2±0.2° 2θ.

In embodiments, the crystalline form of 2-{4-[(3S)-piperidin-3-yl]phenyl}-2H-indazole-7-carboxamide (niraparib) (1S,3R)-(–)-camphorate has an XRPD pattern comprising diffraction angles at 20.3, 17.4, 16.2, 15.1 and 20.2±0.2° 2θ.

In embodiments, the crystalline form of 2-{4-[(3S)-piperidin-3-yl]phenyl}-2H-indazole-7-carboxamide (niraparib) (1S,3R)-(–)-camphorate has an XRPD pattern comprising one or more diffraction angles at 24.4, 19.9, 11.6, 22.3 and/or 22.2±0.2° 2θ.

In embodiments, the crystalline form of 2-{4-[(3S)-piperidin-3-yl]phenyl}-2H-indazole-7-carboxamide (niraparib) (1S,3R)-(–)-camphorate has an XRPD pattern comprising at least two diffraction angles at 24.4, 19.9, 11.6, 22.3 and/or 22.2±0.2° 2θ.

In embodiments, the crystalline form of 2-{4-[(3S)-piperidin-3-yl]phenyl}-2H-indazole-7-carboxamide (niraparib) (1S,3R)-(–)-camphorate has an XRPD pattern comprising at least three diffraction angles at 24.4, 19.9, 11.6, 22.3 and/or 22.2±0.2° 2θ.

In embodiments, the crystalline form of 2-{4-[(3S)-piperidin-3-yl]phenyl}-2H-indazole-7-carboxamide (niraparib) (1S,3R)-(–)-camphorate has an XRPD pattern comprising at least four diffraction angles at 24.4, 19.9, 11.6, 22.3 and/or 22.2±0.2° 2θ.

In embodiments, the crystalline form of 2-{4-[(3S)-piperidin-3-yl]phenyl}-2H-indazole-7-carboxamide (niraparib) (1S,3R)-(–)-camphorate has an XRPD pattern comprising diffraction angles at 24.4, 19.9, 11.6, 22.3 and 22.2±0.2° 2θ.

In embodiments, the crystalline form of 2-{4-[(3S)-piperidin-3-yl]phenyl}-2H-indazole-7-carboxamide (niraparib) (1S,3R)-(–)-camphorate has an XRPD pattern comprising diffraction angles at 20.3, 17.4, 16.2, 15.1, 20.2, 24.4, 19.9, 11.6, 22.3 and 22.2±0.2° 2θ.

In embodiments, the crystalline form of 2-{4-[(3S)-piperidin-3-yl]phenyl}-2H-indazole-7-carboxamide (niraparib) (1S,3R)-(–)-camphorate has an XRPD pattern comprising a diffraction angle at 16.0±0.2° 2θ.

In embodiments, the crystalline form of 2-{4-[(3S)-piperidin-3-yl]phenyl}-2H-indazole-7-carboxamide (niraparib) (1S,3R)-(–)-camphorate has an XRPD pattern comprising a diffraction angle at 21.9±0.2° 2θ.

In embodiments, the crystalline form of 2-{4-[(3S)-piperidin-3-yl]phenyl}-2H-indazole-7-carboxamide (niraparib) (1S,3R)-(–)-camphorate has an XRPD pattern comprising diffraction angles at 16.0 and 21.9±0.2° 2θ.

In embodiments, the crystalline form of 2-{4-[(3S)-piperidin-3-yl]phenyl}-2H-indazole-7-carboxamide (niraparib) (1S,3R)-(–)-camphorate has an XRPD pattern comprising at least one diffraction angle at 20.3, 17.4, 16.2, 15.1, 20.2, 24.4, 19.9, 11.6, 22.3, 22.2, 13.4, 16.0, 26.9, 6.5, 23.9, 18.9, 14.5, 14.0, 21.9 and/or 21.5±0.2° 2θ.

In embodiments, the crystalline form of 2-{4-[(3S)-piperidin-3-yl]phenyl}-2H-indazole-7-carboxamide (niraparib) (1S,3R)-(–)-camphorate has an XRPD pattern comprising diffraction angles with the 2θ values (±0.2° 2θ), and optionally also relative intensities, according to the following table:

| Pos. [°2θ] | Rel. Int. [%] |
|---|---|
| 6.5 | 16.7 |
| 11.6 | 22.6 |
| 13.4 | 19.2 |
| 14.0 | 11.2 |
| 14.5 | 12.8 |
| 15.1 | 48.2 |
| 16.0 | 17.4 |
| 16.2 | 48.7 |
| 17.4 | 61.0 |
| 18.9 | 15.3 |
| 19.9 | 29.8 |
| 20.2 | 34.9 |
| 20.3 | 100 |
| 21.5 | 10.9 |
| 21.9 | 11.0 |
| 22.2 | 19.8 |
| 22.3 | 20.3 |
| 23.9 | 15.9 |
| 24.4 | 31.3 |
| 26.9 | 17.0 |

In embodiments, the crystalline form of 2-{4-[(3S)-piperidin-3-yl]phenyl}-2H-indazole-7-carboxamide (niraparib)

(1S,3R)-(−)-camphorate is characterised by an XRPD pattern substantially as shown in FIG. 9.

In embodiments, the crystalline form of 2-{4-[(3S)-piperidin-3-yl]phenyl}-2H-indazole-7-carboxamide (niraparib) (1S,3R)-(−)-camphorate is characterised by a melting point of about 220° C. to about 230° C.

In embodiments, the crystalline form of 2-{4-[(3S)-piperidin-3-yl]phenyl}-2H-indazole-7-carboxamide (niraparib) (1S,3R)-(−)-camphorate is characterised by a melting point of about 226° C.

In embodiments, the crystalline form of 2-{4-[(3S)-piperidin-3-yl]phenyl}-2H-indazole-7-carboxamide (niraparib) (1S,3R)-(−)-camphorate is characterised by a DSC thermogram in which the onset of melting (endothermic peak) is about 226° C. and/or wherein the peak minimum is about 230° C.

In embodiments, the crystalline form of 2-{4-[(3S)-piperidin-3-yl]phenyl}-2H-indazole-7-carboxamide (niraparib) (1S,3R)-(−)-camphorate is characterised by a DSC thermogram substantially as shown in FIG. 11.

In embodiments, the crystalline form of 2-{4-[(3S)-piperidin-3-yl]phenyl}-2H-indazole-7-carboxamide (niraparib) (1S,3R)-(−)-camphorate is characterised by an infra-red spectrum comprising peaks at about 3367 $cm^{-1}$, about 1693 $cm^{-1}$ and about 1648 $cm^{-1}$.

In embodiments, the crystalline form of 2-{4-[(3S)-piperidin-3-yl]phenyl}-2H-indazole-7-carboxamide (niraparib) (1S,3R)-(−)-camphorate is characterised by an infra-red spectrum substantially as shown in FIG. 8.

In embodiments, the crystalline form of 2-{4-[(3S)-piperidin-3-yl]phenyl}-2H-indazole-7-carboxamide (niraparib) (1S,3R)-(−)-camphorate is characterised by adsorbing less than about 1% by weight of water up to about 90% relative humidity at about 25° C.

In embodiments, the crystalline form of 2-{4-[(3S)-piperidin-3-yl]phenyl}-2H-indazole-7-carboxamide (niraparib) (1S,3R)-(−)-camphorate is characterised by the GVS thermogram substantially as shown in FIG. 12.

In aspects and embodiments, the invention provides 2-{4-[(3S)-piperidin-3-yl]phenyl}-2H-indazole-7-carboxamide (niraparib) mandelate.

In aspects and embodiments, the invention provides 2-{4-[(3S)-piperidin-3-yl]phenyl}-2H-indazole-7-carboxamide (niraparib) (R)-(−)-mandelate.

In aspects and embodiments, the invention provides a crystalline form of 2-{4-[(3S)-piperidin-3-yl]phenyl}-2H-indazole-7-carboxamide (niraparib) (R)-(−)-mandelate.

In aspects and embodiments, the invention provides a crystalline Form 1 of 2-{4-[(3S)-piperidin-3-yl]phenyl}-2H-indazole-7-carboxamide (niraparib) (R)-(−)-mandelate.

In embodiments, the crystalline form of 2-{4-[(3S)-piperidin-3-yl]phenyl}-2H-indazole-7-carboxamide (niraparib) (R)-(−)-mandelate is characterized by an X-ray powder diffraction (XRPD) pattern comprising at least three diffraction angles, when measured using Cu K radiation, selected from a group consisting of about 4.3, 8.4, 8.6, 8.7, 12.4, 13.7, 14.1, 16.1, 16.4, 17.4, 18.4, 18.5, 21.5, 25.1, 27.3, 27.6, 27.7, 28.0, and 28.7 degrees 2θ.

In embodiments, the crystalline form of 2-{4-[(3S)-piperidin-3-yl]phenyl}-2H-indazole-7-carboxamide (niraparib) (R)-(−)-mandelate is characterized by an X-ray powder diffraction (XRPD) pattern comprising at least three diffraction angles, when measured using Cu K radiation, selected from a group consisting of about 8.4, 8.6, 8.7, 13.7, 14.1, 16.4, 17.4, 18.4, 18.5, 21.5, 25.1, 27.3, 27.6, 27.7, 28.0, and 28.7 degrees 2θ.

In embodiments, the crystalline form of 2-{4-[(3S)-piperidin-3-yl]phenyl}-2H-indazole-7-carboxamide (niraparib) (R)-(−)-mandelate is characterized by an X-ray powder diffraction (XRPD) pattern comprising at least three diffraction angles, when measured using Cu K radiation, selected from a group consisting of about 8.6, 8.7, 13.7, 16.4, 17.4, 18.4, 18.5, 21.5, 25.1, 27.3, 27.6, 28.0, and 28.7 degrees 2θ.

In embodiments, the crystalline form of 2-{4-[(3S)-piperidin-3-yl]phenyl}-2H-indazole-7-carboxamide (niraparib) (R)-(−)-mandelate has an XRPD pattern comprising one or more diffraction angles at 18.5, 16.4, 17.4, 8.6 and/or 17.6±0.2° 2θ.

In embodiments, the crystalline form of 2-{4-[(3S)-piperidin-3-yl]phenyl}-2H-indazole-7-carboxamide (niraparib) (R)-(−)-mandelate has an XRPD pattern comprising at least two diffraction angles at 18.5, 16.4, 17.4, 8.6 and/or 17.6±0.2° 2θ.

In embodiments, the crystalline form of 2-{4-[(3S)-piperidin-3-yl]phenyl}-2H-indazole-7-carboxamide (niraparib) (R)-(−)-mandelate has an XRPD pattern comprising at least three diffraction angles at 18.5, 16.4, 17.4, 8.6 and/or 17.6±0.2° 2θ.

In embodiments, the crystalline form of 2-{4-[(3S)-piperidin-3-yl]phenyl}-2H-indazole-7-carboxamide (niraparib) (R)-(−)-mandelate has an XRPD pattern comprising at least four diffraction angles at 18.5, 16.4, 17.4, 8.6 and/or 17.6±0.2° 2θ.

In embodiments, the crystalline form of 2-{4-[(3S)-piperidin-3-yl]phenyl}-2H-indazole-7-carboxamide (niraparib) (R)-(−)-mandelate has an XRPD pattern comprising diffraction angles at 18.5, 16.4, 17.4, 8.6 and 17.6±0.2° 2θ.

In embodiments, the crystalline form of 2-{4-[(3S)-piperidin-3-yl]phenyl}-2H-indazole-7-carboxamide (niraparib) (R)-(−)-mandelate has an XRPD pattern comprising one or more diffraction angles at 8.7, 18.4, 25.1, 27.6 and/or 13.7±0.2° 2θ.

In embodiments, the crystalline form of 2-{4-[(3S)-piperidin-3-yl]phenyl}-2H-indazole-7-carboxamide (niraparib) (R)-(−)-mandelate has an XRPD pattern comprising two or more diffraction angles at 8.7, 18.4, 25.1, 27.6 and/or 13.7±0.2° 2θ.

In embodiments, the crystalline form of 2-{4-[(3S)-piperidin-3-yl]phenyl}-2H-indazole-7-carboxamide (niraparib) (R)-(−)-mandelate has an XRPD pattern comprising three or more diffraction angles at 8.7, 18.4, 25.1, 27.6 and/or 13.7±0.2° 2θ.

In embodiments, the crystalline form of 2-{4-[(3S)-piperidin-3-yl]phenyl}-2H-indazole-7-carboxamide (niraparib) (R)-(−)-mandelate has an XRPD pattern comprising four or more diffraction angles at 8.7, 18.4, 25.1, 27.6 and/or 13.7±0.2° 2θ.

In embodiments, the crystalline form of 2-{4-[(3S)-piperidin-3-yl]phenyl}-2H-indazole-7-carboxamide (niraparib) (R)-(−)-mandelate has an XRPD pattern comprising diffraction angles at 8.7, 18.4, 25.1, 27.6 and 13.7±0.2° 2θ.

In embodiments, the crystalline form of 2-{4-[(3S)-piperidin-3-yl]phenyl}-2H-indazole-7-carboxamide (niraparib) (R)-(−)-mandelate has an XRPD pattern comprising diffraction angles at 18.5, 16.4, 17.4, 8.6, 17.6, 8.7, 18.4, 25.1, 27.6 and 13.7±0.2° 2θ.

In embodiments, the crystalline form of 2-{4-[(3S)-piperidin-3-yl]phenyl}-2H-indazole-7-carboxamide (niraparib) (R)-(−)-mandelate has an XRPD pattern comprising one or more diffraction angles at 18.5, 16.4, 17.4, 8.6, 17.6, 8.7, 18.4, 25.1, 27.6, 13.7, 8.4, 28.7, 28.0, 4.3, 21.5, 27.3, 14.1, 27.7, 12.4 and/or 16.1±0.2° 2θ.

In embodiments, the crystalline form of 2-{4-[(3S)-piperidin-3-yl]phenyl}-2H-indazole-7-carboxamide (niraparib) (R)-(−)-mandelate has an XRPD pattern comprising diffraction angles with the 2θ values (±0.2° 2θ), and optionally also relative intensities, according to the following table:

| Pos. [°2θ] | Rel. Int. [%] |
|---|---|
| 4.3 | 22.3 |
| 8.4 | 27.0 |
| 8.6 | 57.9 |
| 8.7 | 48.3 |
| 12.4 | 17.4 |
| 13.7 | 31.9 |
| 14.1 | 19.9 |
| 16.1 | 17.0 |
| 16.4 | 99.2 |
| 17.4 | 75.9 |
| 17.6 | 52.5 |
| 18.4 | 44.4 |
| 18.5 | 100 |
| 21.5 | 22.2 |
| 25.1 | 39.0 |
| 27.3 | 20.3 |
| 27.6 | 35.9 |
| 27.7 | 19.0 |
| 28.0 | 22.5 |
| 28.7 | 24.8 |

In embodiments, the crystalline form of 2-{4-[(3S)-piperidin-3-yl]phenyl}-2H-indazole-7-carboxamide (niraparib) (R)-(−)-mandelate is characterised by an XRPD pattern substantially as shown in FIG. 15.

In embodiments, the crystalline form of 2-{4-[(3S)-piperidin-3-yl]phenyl}-2H-indazole-7-carboxamide (niraparib) (R)-(−)-mandelate is characterised by a melting point of about 190° C. to about 200° C.

In embodiments, the crystalline form of 2-{4-[(3S)-piperidin-3-yl]phenyl}-2H-indazole-7-carboxamide (niraparib) (R)-(−)-mandelate is characterised by a melting point of about 197° C.

In embodiments, the crystalline form of 2-{4-[(3S)-piperidin-3-yl]phenyl}-2H-indazole-7-carboxamide (niraparib) (R)-(−)-mandelate is characterised by a DSC thermogram in which the onset of melting (endothermic peak) is about 197° C. and/or wherein the peak minimum is about 201° C.

In embodiments, the crystalline form of 2-{4-[(3S)-piperidin-3-yl]phenyl}-2H-indazole-7-carboxamide (niraparib) (R)-(−)-mandelate is characterised by a DSC thermogram substantially as shown in FIG. 18.

In embodiments, the crystalline form of 2-{4-[(3S)-piperidin-3-yl]phenyl}-2H-indazole-7-carboxamide (niraparib) (R)-(−)-mandelate is characterised by an infra-red spectrum comprising peaks at about 3443 cm$^{-1}$, about 3340 cm$^{-1}$, about 1671 cm$^{-1}$ and about 1638 cm$^{-1}$.

In embodiments, the crystalline form of 2-{4-[(3S)-piperidin-3-yl]phenyl}-2H-indazole-7-carboxamide (niraparib) (R)-(−)-mandelate is characterised by an infra-red spectrum substantially as shown in FIG. 14.

In embodiments, the crystalline form of 2-{4-[(3S)-piperidin-3-yl]phenyl}-2H-indazole-7-carboxamide (niraparib) (R)-(−)-mandelate is characterised by a DVS thermogram substantially as shown in FIG. 19.

In aspects and embodiments, the invention provides 2-{4-[(3S)-piperidin-3-yl]phenyl}-2H-indazole-7-carboxamide (niraparib) camsylate.

In aspects and embodiments, the invention provides 2-{4-[(3S)-piperidin-3-yl]phenyl}-2H-indazole-7-carboxamide (niraparib) (1S)-(+)-camsylate.

In aspects and embodiments, the invention provides a crystalline form of 2-{4-[(3S)-piperidin-3-yl]phenyl}-2H-indazole-7-carboxamide (niraparib) (1S)-(+)-camsylate.

In aspects and embodiments, the invention provides a crystalline Form 1 of 2-{4-[(3S)-piperidin-3-yl]phenyl}-2H-indazole-7-carboxamide (niraparib) (1S)-(+)-camsylate.

In embodiments, a crystalline form of 2-{4-[(3S)-piperidin-3-yl]phenyl}-2H-indazole-7-carboxamide (niraparib) (1S)-(+)-camsylate is characterized by an X-ray powder diffraction (XRPD) pattern comprising at least three diffraction angles, when measured using Cu K radiation, selected from a group consisting of about 6.7, 9.5, 11.1, 13.5, 14.3, 16.0, 16.4, 16.7, 16.9, 17.6, 20.3, 22.8, 23.7, 24.3, 24.6, 25.0, 25.2, 25.8, and 26.8 degrees 2θ.

In embodiments, a crystalline form of 2-{4-[(3S)-piperidin-3-yl]phenyl}-2H-indazole-7-carboxamide (niraparib) (1S)-(+)-camsylate is characterized by an X-ray powder diffraction (XRPD) pattern comprising at least three diffraction angles, when measured using Cu K radiation, selected from a group consisting of about 11.1, 13.5, 16.0, 16.4, 16.7, 17.6, 20.3, 23.7, 24.3, 24.6, 25.0, 25.2, and 25.8 degrees 2θ.

In embodiments, a crystalline form of 2-{4-[(3S)-piperidin-3-yl]phenyl}-2H-indazole-7-carboxamide (niraparib) (1S)-(+)-camsylate is characterized by an X-ray powder diffraction (XRPD) pattern comprising at least three diffraction angles, when measured using Cu K radiation, selected from a group consisting of about 11.1, 13.5, 16.0, 16.4, 16.7, 17.6, 20.3, 23.7, 24.3, and 24.6 degrees 2θ.

In embodiments, the crystalline form of 2-{4-[(3S)-piperidin-3-yl]phenyl}-2H-indazole-7-carboxamide (niraparib) (1S)-(+)-camsylate has an XRPD pattern comprising one or more diffraction angles at 16.0, 13.5, 17.6, 24.3 and/or 24.6±0.2° 2θ.

In embodiments, the crystalline form of 2-{4-[(3S)-piperidin-3-yl]phenyl}-2H-indazole-7-carboxamide (niraparib) (1S)-(+)-camsylate has an XRPD pattern comprising at least two diffraction angles at 16.0, 13.5, 17.6, 24.3 and/or 24.6±0.2° 2θ.

In embodiments, the crystalline form of 2-{4-[(3S)-piperidin-3-yl]phenyl}-2H-indazole-7-carboxamide (niraparib) (1S)-(+)-camsylate has an XRPD pattern comprising at least three diffraction angles at 16.0, 13.5, 17.6, 24.3 and/or 24.6±0.2° 2θ.

In embodiments, the crystalline form of 2-{4-[(3S)-piperidin-3-yl]phenyl}-2H-indazole-7-carboxamide (niraparib) (1S)-(+)-camsylate has an XRPD pattern comprising at least four diffraction angles at 16.0, 13.5, 17.6, 24.3 and/or 24.6±0.2° 2θ.

In embodiments, the crystalline form of 2-{4-[(3S)-piperidin-3-yl]phenyl}-2H-indazole-7-carboxamide (niraparib) (1S)-(+)-camsylate has an XRPD pattern comprising diffraction angles at 16.0, 13.5, 17.6, 24.3 and 24.6±0.2° 2θ.

In embodiments, the crystalline form of 2-{4-[(3S)-piperidin-3-yl]phenyl}-2H-indazole-7-carboxamide (niraparib) (1S)-(+)-camsylate has an XRPD pattern comprising one or more diffraction angles at 11.1, 16.4, 23.7, 16.7 and/or 20.3±0.2° 2θ.

In embodiments, the crystalline form of 2-{4-[(3S)-piperidin-3-yl]phenyl}-2H-indazole-7-carboxamide (niraparib) (1S)-(+)-camsylate has an XRPD pattern comprising two or more XRPD diffraction angles at 11.1, 16.4, 23.7, 16.7 and/or 20.3±0.2° 2θ.

In embodiments, the crystalline form of 2-{4-[(3S)-piperidin-3-yl]phenyl}-2H-indazole-7-carboxamide (niraparib) (1S)-(+)-camsylate has an XRPD pattern comprising three or more diffraction angles at 11.1, 16.4, 23.7, 16.7 and/or 20.3±0.2° 2θ.

In embodiments, the crystalline form of 2-{4-[(3S)-piperidin-3-yl]phenyl}-2H-indazole-7-carboxamide (niraparib) (1S)-(+)-camsylate has an XRPD pattern comprising four or more diffraction angles at 11.1, 16.4, 23.7, 16.7 and/or 20.3±0.2° 2θ.

In embodiments, the crystalline form of 2-{4-[(3S)-piperidin-3-yl]phenyl}-2H-indazole-7-carboxamide (niraparib) (1S)-(+)-camsylate has an XRPD pattern comprising diffraction angles at 11.1, 16.4, 23.7, 16.7 and 20.3±0.2° 2θ.

In embodiments, the crystalline form of 2-{4-[(3S)-piperidin-3-yl]phenyl}-2H-indazole-7-carboxamide (niraparib) (1S)-(+)-camsylate has an XRPD pattern comprising diffraction angles at 16.0, 13.5, 17.6, 24.3, 24.6, 11.1, 16.4, 23.7, 16.7 and 20.3±0.2° 2θ.

In embodiments, the crystalline form of 2-{4-[(3S)-piperidin-3-yl]phenyl}-2H-indazole-7-carboxamide (niraparib) (1S)-(+)-camsylate has an XRPD pattern comprising one or more XRPD diffraction angles at 6.7, 16.4, 23.7 and/or 25.2±0.2° 2θ.

In embodiments, the crystalline form of 2-{4-[(3S)-piperidin-3-yl]phenyl}-2H-indazole-7-carboxamide (niraparib) (1S)-(+)-camsylate has an XRPD pattern comprising at least two diffraction angles at 6.7, 16.4, 23.7 and/or 25.2±0.2° 2θ.

In embodiments, the crystalline form of 2-{4-[(3S)-piperidin-3-yl]phenyl}-2H-indazole-7-carboxamide (niraparib) (1S)-(+)-camsylate has an XRPD pattern comprising at least three diffraction angles at 6.7, 16.4, 23.7 and/or 25.2±0.2° 2θ.

In embodiments, the crystalline form of 2-{4-[(3S)-piperidin-3-yl]phenyl}-2H-indazole-7-carboxamide (niraparib) (1S)-(+)-camsylate has an XRPD pattern comprising diffraction angles at 6.7, 16.4, 23.7 and 25.2±0.2° 2θ.

In embodiments, the crystalline form of 2-{4-[(3S)-piperidin-3-yl]phenyl}-2H-indazole-7-carboxamide (niraparib) (1S)-(+)-camsylate has an XRPD pattern comprising at least one diffraction angle at 16.0, 13.5, 17.6, 24.3, 24.6, 11.1, 16.4, 23.7, 16.7, 20.3, 6.7, 25.2, 25.0, 25.8, 26.8, 22.8, 9.5, 16.9, 14.3 and/or 7.7±0.2° 2θ.

In embodiments, the crystalline form of 2-{4-[(3S)-piperidin-3-yl]phenyl}-2H-indazole-7-carboxamide (niraparib) (1S)-(+)-camsylate has an XRPD pattern comprising diffraction angles with the 2θ values (±0.2° 2θ), and optionally also relative intensities, according to the following table:

| Pos. [°2θ] | Rel. Int. [%] |
|---|---|
| 6.7 | 13.8 |
| 7.7 | 8.9 |
| 9.5 | 10.4 |
| 11.1 | 22.2 |
| 13.5 | 58.6 |
| 14.3 | 9.1 |
| 16.0 | 100 |
| 16.4 | 20.4 |
| 16.7 | 19.1 |
| 16.9 | 9.8 |
| 17.6 | 55.4 |
| 20.3 | 14.5 |
| 22.8 | 11.6 |
| 23.7 | 19.6 |
| 24.3 | 47.4 |
| 24.6 | 45.9 |
| 25.0 | 12.9 |
| 25.2 | 13.4 |
| 25.8 | 12.0 |
| 26.8 | 11.6 |

In embodiments, the crystalline form of 2-{4-[(3S)-piperidin-3-yl]phenyl}-2H-indazole-7-carboxamide (niraparib) (1S)-(+)-camsylate is characterised by an XRPD pattern substantially as shown in FIG. 22.

In embodiments, the crystalline form of 2-{4-[(3S)-piperidin-3-yl]phenyl}-2H-indazole-7-carboxamide (niraparib) (1S)-(+)-camsylate is characterised by a melting point of about 235° C. to about 245° C.

In embodiments, the crystalline form of 2-{4-[(3S)-piperidin-3-yl]phenyl}-2H-indazole-7-carboxamide (niraparib) (1S)-(+)-camsylate is characterised by a melting point of about 239° C.

In embodiments, the crystalline form of 2-{4-[(3S)-piperidin-3-yl]phenyl}-2H-indazole-7-carboxamide (niraparib) (1S)-(+)-camsylate is characterised by a DSC thermogram in which the onset of melting (endothermic peak) is about 235° C. and/or wherein the peak minimum is about 246° C.

In embodiments, the crystalline form of 2-{4-[(3S)-piperidin-3-yl]phenyl}-2H-indazole-7-carboxamide (niraparib) (1S)-(+)-camsylate is characterised by a DSC thermogram substantially as shown in FIG. 24.

In embodiments, the crystalline form of 2-{4-[(3S)-piperidin-3-yl]phenyl}-2H-indazole-7-carboxamide (niraparib) (1S)-(+)-camsylate is characterised by an infra-red spectrum comprising peaks at about 3467 cm$^{-1}$, about 3306 cm$^{-1}$, about 1724 cm$^{-1}$, about 1660 cm$^{-1}$, and about 1611 cm$^{-1}$.

In embodiments, the crystalline form of 2-{4-[(3S)-piperidin-3-yl]phenyl}-2H-indazole-7-carboxamide (niraparib) (1S)-(+)-camsylate is characterised by an infra-red spectrum substantially as shown in FIG. 21.

In embodiments, the crystalline form of 2-{4-[(3S)-piperidin-3-yl]phenyl}-2H-indazole-7-carboxamide (niraparib) (1S)-(+)-camsylate is characterised by adsorbing less than about 2% by weight of water up to about 90% relative humidity at about 25° C.

In embodiments, the crystalline form of 2-{4-[(3S)-piperidin-3-yl]phenyl}-2H-indazole-7-carboxamide (niraparib) (1S)-(+)-camsylate is characterised by adsorbing about 1.3% by weight of water up to about 90% relative humidity at about 25° C.

In embodiments, the crystalline form of 2-{4-[(3S)-piperidin-3-yl]phenyl}-2H-indazole-7-carboxamide (niraparib) (1S)-(+)-camsylate is characterised by a GVS thermogram substantially as shown in FIG. 25.

In other aspects, the invention provides a pharmaceutical composition comprising the 2-{4-[(3S)-piperidin-3-yl]phenyl}-2H-indazole-7-carboxamide (niraparib)camphorate, 2-{4-[(3S)-piperidin-3-yl]phenyl}-2H-indazole-7-carboxamide (niraparib)mandelate or 2-{4-[(3S)-piperidin-3-yl]phenyl}-2H-indazole-7-carboxamide (niraparib)camsylate defined hereinbefore, and at least one pharmaceutically acceptable excipient. In embodiments, a pharmaceutical composition is adapted for oral administration.

In other aspects, the invention provides a pharmaceutical composition comprising a crystalline form of 2-{4-[(3S)-piperidin-3-yl]phenyl}-2H-indazole-7-carboxamide (niraparib)camphorate, 2-{4-[(3S)-piperidin-3-yl]phenyl}-2H-indazole-7-carboxamide (niraparib)mandelate or 2-{4-[(3S)-piperidin-3-yl]phenyl}-2H-indazole-7-carboxamide (niraparib)camsylate defined hereinbefore, and at least one pharmaceutically acceptable excipient. In embodiments, a pharmaceutical composition is adapted for oral administration.

In embodiments, a pharmaceutical composition comprises a crystalline form of 2-{4-[(3S)-piperidin-3-yl]phenyl}-2H-indazole-7-carboxamide (niraparib) (1R,3S)-(+)-camphorate, and at least one pharmaceutically acceptable excipient. In embodiments, a pharmaceutical composition is adapted for oral administration.

In embodiments, a pharmaceutical composition comprises a crystalline form of 2-{4-[(3S)-piperidin-3-yl]phenyl}-2H-indazole-7-carboxamide (niraparib) (1S,3R)-(−)-camphorate, and at least one pharmaceutically acceptable excipient. In embodiments, a pharmaceutical composition is adapted for oral administration.

In embodiments, a pharmaceutical composition comprises a crystalline form of 2-{4-[(3S)-piperidin-3-yl]phenyl}-2H-indazole-7-carboxamide (niraparib) (R)-(−)-mandelate, and at least one pharmaceutically acceptable excipient. In embodiments, a pharmaceutical composition is adapted for oral administration.

In embodiments, a pharmaceutical composition comprises a crystalline form of 2-{4-[(3S)-piperidin-3-yl]phenyl}-2H-indazole-7-carboxamide (niraparib) (1S)-(+)-camsylate, and at least one pharmaceutically acceptable excipient. In embodiments, a pharmaceutical composition is adapted for oral administration.

In other aspects, the invention provides a 2-{4-[(3S)-piperidin-3-yl]phenyl}-2H-indazole-7-carboxamide (niraparib) camphorate, 2-{4-[(3S)-piperidin-3-yl]phenyl}-2H-indazole-7-carboxamide (niraparib) mandelate, 2-{4-[(3S)-piperidin-3-yl]phenyl}-2H-indazole-7-carboxamide (niraparib) camsylate, or the pharmaceutical composition thereof and defined hereinbefore, for use in therapy. In embodiments, the invention provides a crystalline form of 2-{4-[(3S)-piperidin-3-yl]phenyl}-2H-indazole-7-carboxamide (niraparib) camphorate, 2-{4-[(3S)-piperidin-3-yl]phenyl}-2H-indazole-7-carboxamide (niraparib) mandelate, 2-{4-[(3S)-piperidin-3-yl]phenyl}-2H-indazole-7-carboxamide (niraparib) camsylate, or the pharmaceutical composition thereof and defined hereinbefore, for use in therapy.

In other aspects, the invention provides use of a 2-{4-[(3S)-piperidin-3-yl]phenyl}-2H-indazole-7-carboxamide (niraparib) camphorate, 2-{4-[(3S)-piperidin-3-yl]phenyl}-2H-indazole-7-carboxamide (niraparib) mandelate, 2-{4-[(3S)-piperidin-3-yl]phenyl}-2H-indazole-7-carboxamide (niraparib) camsylate, or the pharmaceutical composition thereof and defined hereinbefore, in the manufacture of a medicament. In embodiments, the invention provides use of a crystalline form of 2-{4-[(3S)-piperidin-3-yl]phenyl}-2H-indazole-7-carboxamide (niraparib) camphorate, 2-{4-[(3S)-piperidin-3-yl]phenyl}-2H-indazole-7-carboxamide (niraparib) mandelate, 2-{4-[(3S)-piperidin-3-yl]phenyl}-2H-indazole-7-carboxamide (niraparib) camsylate, or the pharmaceutical composition thereof and defined hereinbefore, in the manufacture of a medicament.

In other aspect, the invention provides a method of treating cancer, stroke, autoimmune diabetes, a neurological disease, an inflammatory disease, a metabolic disease or a cardiovascular disease in a human in need thereof, the method comprising administering to the human an effective amount of the 2-{4-[(3S)-piperidin-3-yl]phenyl}-2H-indazole-7-carboxamide (niraparib) camphorate, 2-{4-[(3S)-piperidin-3-yl]phenyl}-2H-indazole-7-carboxamide (niraparib) mandelate, or 2-{4-[(3S)-piperidin-3-yl]phenyl}-2H-indazole-7-carboxamide (niraparib) camsylate defined hereinbefore, or the pharmaceutical composition defined hereinbefore. In embodiments, a method comprises administering to the human an effective amount of a crystalline form of 2-{4-[(3S)-piperidin-3-yl]phenyl}-2H-indazole-7-carboxamide (niraparib) camphorate, 2-{4-[(3S)-piperidin-3-yl]phenyl}-2H-indazole-7-carboxamide (niraparib) mandelate, or 2-{4-[(3S)-piperidin-3-yl]phenyl}-2H-indazole-7-carboxamide (niraparib) camsylate defined hereinbefore, or the pharmaceutical composition defined hereinbefore.

In embodiments the method is a method of treating cancer.

In embodiments, the cancer is associated with BRCA1 and/or BRCA2 mutations.

In embodiments, said cancer is association with a mutation in ATM, ATR, BAP1, BARD1, BLM, BRIP1, MRE11A, NBN, PALB2, RAD51, RAD51B, RAD51C, RAD51D, RAD52, RAD54L, or XRCC2, or any combination thereof.

In embodiments, said cancer is epithelial ovarian cancer, fallopian tube cancer, or primary peritoneal cancer.

In other aspects, the invention provides the 2-{4-[(3S)-piperidin-3-yl]phenyl}-2H-indazole-7-carboxamide (niraparib) camphorate, 2-{4-[(3S)-piperidin-3-yl]phenyl}-2H-indazole-7-carboxamide (niraparib) mandelate, or 2-{4-[(3S)-piperidin-3-yl]phenyl}-2H-indazole-7-carboxamide (niraparib) camsylate thereof and defined hereinbefore, or the pharmaceutical composition defined hereinbefore, for use in a method as defined hereinbefore. In embodiments, a crystalline form of 2-{4-[(3S)-piperidin-3-yl]phenyl}-2H-indazole-7-carboxamide (niraparib) camphorate, 2-{4-[(3S)-piperidin-3-yl]phenyl}-2H-indazole-7-carboxamide (niraparib) mandelate, or 2-{4-[(3S)-piperidin-3-yl]phenyl}-2H-indazole-7-carboxamide (niraparib) camsylate thereof and defined hereinbefore, or the pharmaceutical composition defined hereinbefore, for use in a method as defined hereinbefore.

In other aspects, the invention provides use of the 2-{4-[(3S)-piperidin-3-yl]phenyl}-2H-indazole-7-carboxamide (niraparib) camphorate, 2-{4-[(3S)-piperidin-3-yl]phenyl}-2H-indazole-7-carboxamide (niraparib) mandelate, or 2-{4-[(3S)-piperidin-3-yl]phenyl}-2H-indazole-7-carboxamide (niraparib) camsylate defined hereinbefore, or the pharmaceutical composition described hereinbefore, in the manufacture of a medicament for use in a method as defined hereinbefore. In embodiments, the invention provides use of a crystalline form of 2-{4-[(3S)-piperidin-3-yl]phenyl}-2H-indazole-7-carboxamide (niraparib) camphorate, 2-{4-[(3S)-piperidin-3-yl]phenyl}-2H-indazole-7-carboxamide (niraparib) mandelate, or 2-{4-[(3S)-piperidin-3-yl]phenyl}-2H-indazole-7-carboxamide (niraparib) camsylate defined hereinbefore, or the pharmaceutical composition described hereinbefore, in the manufacture of a medicament for use in a method as defined hereinbefore.

DETAILED DESCRIPTION

Figure 1:
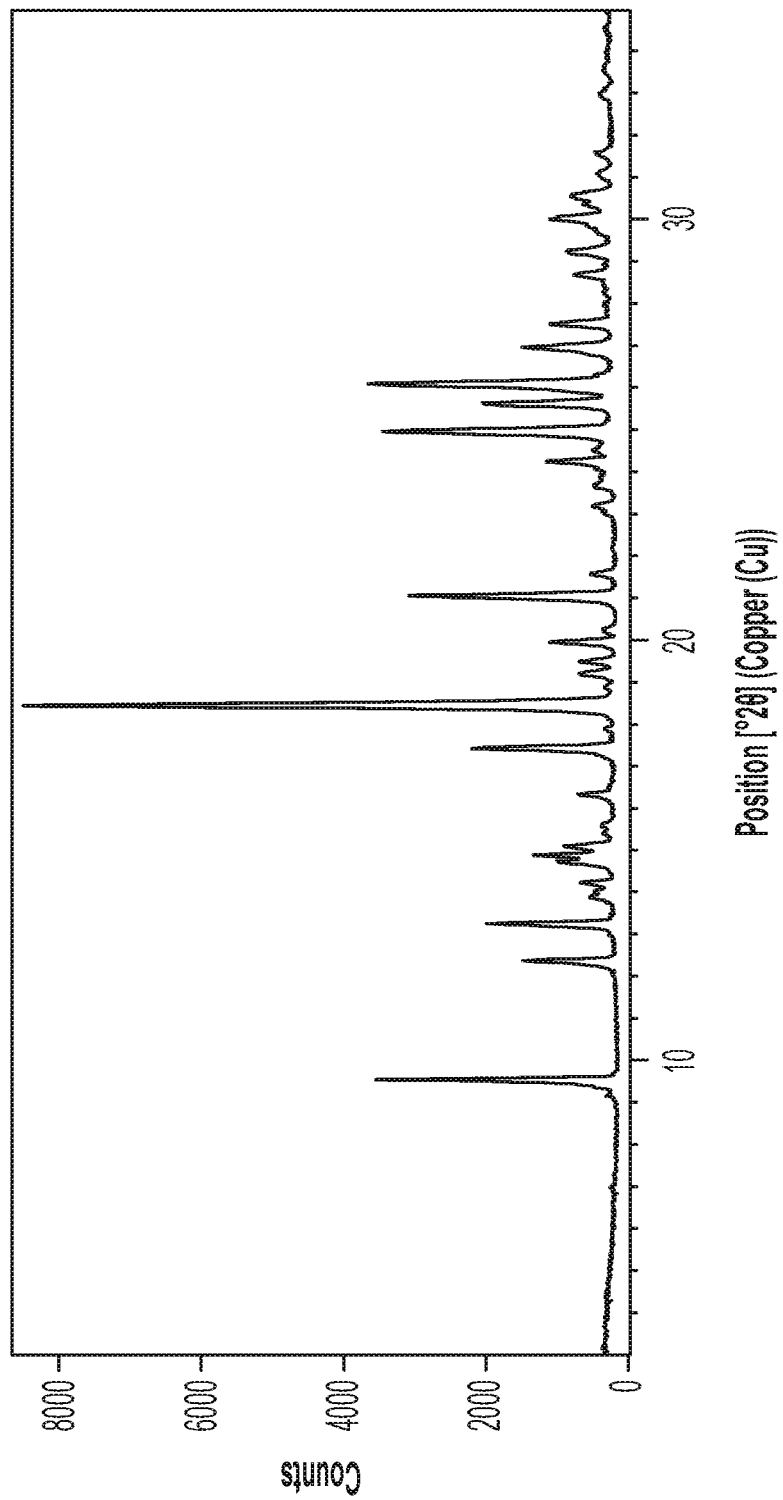
FIG. 1 shows an exemplary XRPD pattern for the 2-{4-[(3S)-piperidin-3-yl]phenyl}-2H-indazole-7-carboxamide (niraparib) tosylate monohydrate used in Example 10.

Although specific embodiments of the present disclosure will now be described with reference to the description and examples, it should be understood that such embodiments are by way of example only and merely illustrative of but a small number of the many possible specific embodiments which can represent applications of the principles of the present disclosure. Various changes and modifications will be obvious to those of skill in the art given the benefit of the present disclosure and are deemed to be within the spirit and scope of the present disclosure as further defined in the appended claims.

Definitions

Unless defined otherwise, all technical and scientific terms used herein have the same meanings as commonly understood by one of ordinary skill in the art to which this disclosure belongs. Although any methods and materials similar or equivalent to those described herein can be used in the practice or testing of the present invention, exemplary methods, devices, and materials are now described. All technical and patent publications cited herein are incorporated herein by reference in their entirety. Nothing herein is to be construed as an admission that the invention is not entitled to antedate such disclosure by virtue of prior invention.

The practice of the present disclosure will employ, unless otherwise indicated, conventional techniques of chemical synthesis, tissue culture, immunology, molecular biology, microbiology, cell biology and recombinant DNA, which are within the skill of the art (see e.g. Michael R. Green and Joseph Sambrook, Molecular Cloning; 4$^{th}$ ed., Cold Spring Harbor Laboratory Press 2012).

Numerical designations, e.g. pH, temperature, time, concentration, molecular weight, etc., including ranges, are approximations which are varied (+) or (−) by increments of 0.1 or 1.0, where appropriate. It is to be understood, although not always explicitly stated that all numerical designations are preceded by the term "about". It also is to be understood, although not always explicitly stated, that the reagents described herein are merely exemplary and that equivalents of such may be known in the art.

As used in the specification and claims, the singular forms "a", "an" and "the" include plural references unless the context clearly dictates otherwise. For example, the term "a cell" includes a plurality of cells, including mixtures thereof. Unless specifically stated or obvious from context, as used herein, the term "or" is understood to be inclusive. The term "including" is used herein to mean, and is used interchangeably with, the phrase "including but not limited to".

As used herein, and unless otherwise specified, the terms "about" and "approximately", when used in connection with doses, amounts, or weight percent of ingredients of a composition or a dosage form, mean a dose, amount, or weight percent that is recognized by those of ordinary skill in the art to provide a pharmacological effect equivalent to that obtained from the specified dose, amount, or weight percent. Specifically, the terms "about" and "approximately", when used in this context, contemplate a dose, amount, or weight percent within 15%, more specifically within 10%, more specifically within 5%, of the specified dose, amount, or weight percent. As used herein, and unless otherwise specified, the terms "about" and "approximately", when used in connection with a numeric value or range of values which is provided to characterize a particular solid form, e.g., a specific temperature or temperature range, such as, for example, that describing a melting, dehydration, desolvation or glass transition temperature; a mass change, such as, for example, a mass change as a function of temperature or humidity; a solvent or water content, in terms of, for example, mass or a percentage; or a peak position or diffraction angle, such as, for example, in analysis by IR or Raman spectroscopy or XRPD; indicate that the value or range of values may deviate to an extent deemed reasonable to one of ordinary skill in the art while still describing the particular solid form. Specifically, the terms "about" and "approximately", when used in this context, indicate that the numeric value or range of values may vary, in particular embodiments, within 20%, 10%, 9%, 8%, 7%, 6%, 5%, 4%, 3%, 2%, 1.5%, 1%, 0.5%, or 0.25% of the recited value or range of values. With respect to XRPD, values given are ±0.2 degrees 2θ if not expressly specified as such.

As used herein, the term "comprising" or "comprises" is intended to mean that the compositions and methods include the recited elements, but not excluding others. "Consisting essentially of" when used to define compositions and methods, shall mean excluding other elements of any essential significance to the combination for the stated purpose. Thus, a composition consisting essentially of the elements as defined herein would not exclude contaminants from the isolation and purification method and pharmaceutically acceptable carriers, such as phosphate buffered saline, preservatives and the like. "Consisting of" shall mean excluding more than trace elements of other ingredients and substantial method steps for administering the compositions of this disclosure or process steps to produce a composition or achieve an intended result. Embodiments defined by each of these transition terms are within the scope of this invention. Use of the term "comprising" herein is intended to encompass, and to disclose, the corresponding statements in which the term "comprising" is replaced by "consisting essentially of" or "consisting of".

The term "subject" is used to mean an animal, preferably a mammal, including a human or non-human. The terms "patient" and "subject" may be used interchangeably.

"Administering" is defined herein as a means of providing an agent or a composition containing the agent to a subject in a manner that results in the agent being inside the subject's body. Such an administration can be by any route including, without limitation, oral, transdermal (e.g. by the vagina, rectum, or oral mucosa), by injection (e.g. subcutaneous, intravenous, parenteral, intraperitoneal, or into the central nervous system), or by inhalation (e.g. oral or nasal). Pharmaceutical preparations are, of course, given by forms suitable for each administration route.

A "therapeutically effective amount" or "effective amount" is that amount of a pharmaceutical agent to achieve a pharmacological effect. The term "therapeutically effective amount" includes, for example, a prophylactically effective amount. An "effective amount" of niraparib is an amount needed to achieve a desired pharmacologic effect or therapeutic improvement without undue adverse side effects. The effective amount of a niraparib will be selected by those skilled in the art depending on the particular patient and the disease. It is understood that "an effective amount" or a "therapeutically effective amount" can vary from subject to subject, due to variation in metabolism of niraparib, age, weight, general condition of the subject, the condition being treated, the severity of the condition being treated, and the judgment of the prescribing physician. As used herein, amelioration or lessening of the symptoms of a particular disease, disorder or condition by administration of a particular compound or pharmaceutical composition refers to any decrease of severity, delay in onset, slowing of progression, or shortening of duration, whether permanent or temporary, lasting or transient that is attributed to or associated with administration of the compound or composition.

The terms "treat", "treating" or "treatment", as used herein, include alleviating, abating or ameliorating a disease or condition, for example cancer, symptoms, preventing additional symptoms, ameliorating or preventing the underlying metabolic causes of symptoms, inhibiting the disease or condition, e.g. arresting the development of the disease or condition, relieving the disease or condition, causing regression of the disease or condition, relieving a condition caused by the disease or condition, or stopping the symptoms of the disease or condition either prophylactically and/or therapeutically.

The term "suffering" as it relates to the term "treatment" refers to a patient or individual who has been diagnosed with or is predisposed to the disease. A patient may also be referred to being "at risk of suffering" from a disease because of a history of disease in their family lineage or because of the presence of genetic mutations associated with the disease. A patient at risk of a disease has not yet developed all or some of the characteristic pathologies of the disease.

As used herein, "weight percent", "wt %", "percent by weight", "% by weight", and variations thereof refer to the concentration of a substance as the weight of that substance divided by the total weight of the composition and multiplied by 100.

The term "amorphous", "amorphous form", and related terms used herein mean that the substance, component or product in question is not substantially crystalline as determined by X-ray diffraction. In certain embodiments, a sample comprising an amorphous form of a substance may be substantially free of other amorphous forms and/or crystal forms.

The term "crystalline" and related terms used herein, when used to describe a substance, component, product, or form, means that the substance, component or product is substantially crystalline as determined by X-ray diffraction (see e.g. Remington's Pharmaceutical Sciences, 22nd ed., Pharmaceutical Press, 2012; *The United States Pharmacopoeia*, 30th ed., 2011).

The term "crystal form", "crystalline form" and related terms herein refer to a crystalline solid form comprising a chemical compound, and may refer to a particular single-component or multiple-component crystal form, including, but not limited to, a polymorph, a solvate, a hydrate or other molecular complex, a salt, a solvate of a salt, a hydrate of a salt, or other molecular complex of a salt, or a polymorph thereof.

The terms "polymorphs", "polymorphic forms" and related terms herein refer to two or more crystal forms that comprise the same molecule, molecules or ions. Different polymorphs may have different physical properties such as, for example, melting temperatures, heats of fusion, solubilities, dissolution rates and/or vibrational spectra as a result of the arrangement or conformation of the molecules or ions in the crystal lattice. The differences in physical properties exhibited by polymorphs affect pharmaceutical parameters such as storage stability, compressibility and density (important in formulation and product manufacturing), and dissolution rate (an important factor in bioavailability). Differences in stability can result from changes in chemical reactivity (e.g. differential oxidation, such that a dosage form discolors more rapidly when comprised of one polymorph than when comprised of another polymorph) or mechanical changes (e.g. tablets crumble on storage as a kinetically favored polymorph converts to thermodynamically more stable polymorph) or both (e.g. tablets of one polymorph are more susceptible to breakdown at high humidity). As a result of solubility/dissolution differences, in the extreme case, some polymorphic transitions may result in lack of potency or, at the other extreme, toxicity, which may result in higher or lower incidence of unwanted side effects or a change in severity of an unwanted side effect. In addition, the physical properties of the crystal may be important in processing; for example, one polymorph might be more likely to form solvates or might be difficult to filter and wash free of impurities (e.g. particle shape and size distribution might be different between polymorphs).

Where a counterion (especially an anion within a salt) referred to herein has one or more stereoisomers, and no particular stereochemistry of said counterion is mentioned, then it is intended that the reference encompasses all stereoisomers of the counterion and mixtures thereof. Stereoisomers includes enantiomeric and diasteriomeric forms and mixtures thereof. For example, a reference herein to "mandelate" without a stereochemical designation is intended to refer to (R)-α-hydroxyphenylacetic acid, (S)-α-hydroxyphenylacetic acid and mixtures thereof, including racemic mixtures thereof.

Techniques for characterizing crystal forms and amorphous forms include, but are not limited to, thermal gravimetric analysis (TGA), melting point, differential scanning calorimetry (DSC), X-ray powder diffractometry (XRPD), single-crystal X-ray diffractometry, vibrational spectroscopy, e.g. infrared (IR) and Raman spectroscopy, solid-state and solution nuclear magnetic resonance (NMR) spectroscopy, optical microscopy (e.g. polarized light microscopy), hot stage optical microscopy, scanning electron microscopy (SEM), electron crystallography, dynamic vapor sorption (DVS), and quantitative analysis, particle size analysis (PSA), surface area analysis, solubility studies and dissolution studies. Exemplary experimental values described herein may be variable according to the standard measures of the field, such as the exemplary variation described herein.

Where a crystalline form is characterized by one or more XRPD diffraction angles, and unless otherwise indicated, it is to be understood that the XRPD pattern is obtained under standard conditions (e.g. as described herein) and that the 2θ values may be variable according to the standard measures in the field. For example, 2θ values recited herein may be variable by ±0.2°. Furthermore, where a crystalline form is characterized by one or more specified XRPD diffraction angles, those diffraction angles will typically represent diffraction angles having a relative intensity within the diffractogram of at least 1%, e.g. of at least 2%, 5% or 10% relative intensity.

The recitation of an embodiment for a variable or aspect herein includes that embodiment as any single embodiment or in combination with any other embodiments or portions thereof.

Compositions and methods provided herein may be combined with one or more of any of the other compositions and methods provided herein.

The following abbreviations are used herein:

° C. = Celsius
DMSO = dimethyl sulfoxide
DSC = differential scanning calorimetry
ESI = electrospray ionisation
FT-IR = Fourier Transform-Infrared (spectroscopy)
GVS = Gravimetric Vapour Sorption
h = hour
HPLC = high pressure liquid chromatography
Hz = hertz
2-MeTHF = 2-methyltetrahydrofuran
MHz = megahertz;
min = minute
MS = mass spectrometry
NMR = nuclear magnetic resonance
rt/RT = room temperature
SXRD = Single crystal X-ray diffraction
TBME = tert-butyl methyl ether
THF = tetrahydrofuran Salts The present invention relates to novel salt forms of the drug 2-{4-[(3S)-piperidin-3-yl]phenyl}-2H-indazole-7-carboxamide (niraparib) which have desirable properties for pharmaceutical formulation, such as e.g. improved aqueous solubility, low hygroscopicity and/or good stability.

Accordingly, the present invention provides a camphorate, mandelate or camsylate salt of 2-{4-[(3S)-piperidin-3-yl]phenyl}-2H-indazole-7-carboxamide (niraparib). In particular, the invention provides a camphorate, mandelate or camsylate salt of 2-{4-[(3S)-piperidin-3-yl]phenyl}-2H-indazole-7-carboxamide (niraparib) in a crystalline form, e.g. as described in detail hereinafter.

Exemplary crystalline forms of salts of 2-{4-[(3S)-piperidin-3-yl]phenyl}-2H-indazole-7-carboxamide (niraparib) are also described herein. Exemplary X-ray powder diffraction (XRPD) patterns are also described herein. In embodiments, an XRPD pattern is measured using Cu K radiation. In embodiments, an XRPD pattern is characterized by certain diffraction angles (peaks) as described herein.

Niraparib Camphorate

In one aspect, the invention provides a camphorate salt of 2-{4-[(3S)-piperidin-3-yl]phenyl}-2H-indazole-7-carboxamide (niraparib) ("niraparib camphorate"). In a preferred aspect, the invention provides crystalline niraparib camphorate.

The camphorate salt may be selected from (1R,3S)-(+)-camphorate, (1S,3R)-(+)-camphorate, (+/−)-camphorate, and mixtures thereof.

In one embodiment, the camphorate is (1R,3S)-(+)-camphorate (referred to as "(+)-camphorate" hereinafter). The (+)-camphorate salt comprises an ionised form of (1R,3S)-(+)-camphoric acid, which has the following structure:

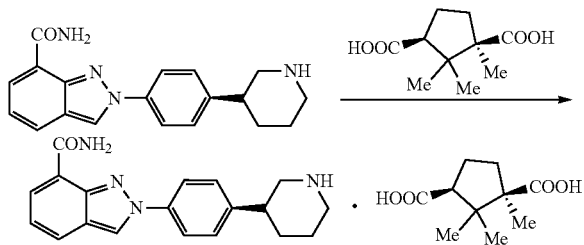

Viewed from this aspect, the invention provides 2-{4-[(3S)-piperidin-3-yl]phenyl}-2H-indazole-7-carboxamide (niraparib) (+)-camphorate, e.g. a crystalline form of 2-{4-[(3S)-piperidin-3-yl]phenyl}-2H-indazole-7-carboxamide (niraparib) (+)-camphorate. In embodiments, a crystalline form of 2-{4-[(3S)-piperidin-3-yl]phenyl}-2H-indazole-7-carboxamide (niraparib) (+)-camphorate comprises Form 1 2-{4-[(3S)-piperidin-3-yl]phenyl}-2H-indazole-7-carboxamide (niraparib) (+)-camphorate, e.g. as described herein.

In embodiments, a crystalline form (crystalline Form 1) of niraparib (+)-camphorate is characterised by one or more (e.g. one, two, three, four or five) XRPD diffraction angles at 2θ values of 16.2°, 17.5°, 20.0°, 13.4° and/or 15.2°. In other embodiments, a crystalline form of niraparib (+)-camphorate is characterised by at least two XRPD diffraction angles at 2θ values of 16.2°, 17.5°, 20.0°, 13.4° and/or 15.2°. In other embodiments, a crystalline form (crystalline Form 1) of niraparib (+)-camphorate is characterised by at least three XRPD diffraction angles at 2θ values of 16.2°, 17.5°, 20.0°, 13.4° and/or 15.2°. In other embodiments, a crystalline form (crystalline Form 1) of niraparib (+)-camphorate is characterised by at least four XRPD diffraction angles at 2θ values of 16.2°, 17.5°, 20.0°, 13.4° and/or 15.2°.

In embodiments, a crystalline form (crystalline Form 1) of niraparib (+)-camphorate is characterised by an XRPD diffraction angle at a 2θ value of 16.2°. In embodiments, a crystalline form (crystalline Form 1) of niraparib (+)-camphorate is characterised by an XRPD diffraction angle at a 2θ value of 17.5°. In embodiments, a crystalline form (crystalline Form 1) of niraparib (+)-camphorate is characterised by XRPD diffraction angles at 2θ values of 16.2° and 17.5°. In embodiments, a crystalline form (crystalline Form 1) of niraparib (+)-camphorate is characterised by XRPD diffraction angles at 2θ values of 16.2°, 17.5° and 20.0°. In embodiments, a crystalline form (crystalline Form 1) of niraparib (+)-camphorate is characterised by XRPD diffraction angles at 2θ values of 16.2°, 17.5°, 20.0° and 13.4°. In embodiments, a crystalline form (crystalline Form 1) of niraparib (+)-camphorate is characterised by XRPD diffraction angles at 2θ values of 16.2°, 17.5°, 20.0°, 13.4° and 15.2°.

In embodiments, a crystalline form (crystalline Form 1) of niraparib (+)-camphorate is characterised by one or more (e.g. one, two, three, four or five) XRPD diffraction angles at 2θ values of 20.4°, 21.6°, 24.0°, 11.7° and/or 18.0°. In other embodiments, a crystalline form (crystalline Form 1) of niraparib (+)-camphorate is characterised by at least two XRPD diffraction angles at 2θ values of 20.4°, 21.6°, 24.0°, 11.70 and/or 18.0°. In other embodiments, a crystalline form (crystalline Form 1) of niraparib (+)-camphorate is characterised by at least three XRPD diffraction angles at 2θ values of 20.4°, 21.6°, 24.0°, 11.70 and/or 18.0°. In other embodiments, a crystalline form (crystalline Form 1) of niraparib (+)-camphorate is characterised by at least four XRPD diffraction angles at 2θ values of 20.4°, 21.6°, 24.0°, 11.7° and/or 18.0°. In embodiments, a crystalline form (crystalline Form 1) of niraparib (+)-camphorate is characterised by XRPD diffraction angles at 2θ values of 20.4°, 21.6°, 24.0°, 11.7° and 18.0°.

In embodiments, a crystalline form (crystalline Form 1) of niraparib (+)-camphorate is characterised by one or more (e.g. six, seven, eight, nine or ten) XRPD diffraction angles at 2θ values of 16.2°, 17.5°, 20.0°, 13.4°, 15.2°, 20.4°, 21.6°, 24.0°, 11.7° and/or 18.0°. In other embodiments, a crystalline form (crystalline Form 1) of niraparib (+)-camphorate is characterised by at least six XRPD diffraction angles at 2θ values of 16.2°, 17.5°, 20.0°, 13.4°, 15.2°, 20.4°, 21.6°, 24.0°, 11.7° and/or 18.0°. In other embodiments, a crystalline form (crystalline Form 1) of niraparib (+)-camphorate is characterised by at least seven XRPD diffraction angles at 2θ values of 16.2°, 17.5°, 20.0°, 13.4°, 15.2°, 20.4°, 21.6°, 24.0°, 11.70 and/or 18.0°. In other embodiments, a crystalline form (crystalline Form 1) of niraparib (+)-camphorate is characterised by at least eight XRPD diffraction angles at 2θ values of 16.2°, 17.5°, 20.0°, 13.4°, 15.2°, 20.4°, 21.6°, 24.0°, 11.7° and/or 18.0°. In other embodiments, a crystalline form (crystalline Form 1) of niraparib (+)-camphorate is characterised by at least nine XRPD diffraction angles at 2θ values of 16.2°, 17.5°, 20.0°, 13.4°, 15.2°, 20.4°, 21.6°, 24.0°, 11.7° and/or 18.0°.

In embodiments, a crystalline form (crystalline Form 1) of niraparib (+)-camphorate is characterised by XRPD diffraction angles at 2θ values of 16.2°, 17.5°, 20.0°, 13.4°, 15.2° and 20.4°. In embodiments, a crystalline form (crystalline Form 1) of niraparib (+)-camphorate is characterised by XRPD diffraction angles at 2θ values of 16.2°, 17.5°, 20.0°, 13.4°, 15.2°, 20.4° and 21.6°. In embodiments, a crystalline form (crystalline Form 1) of niraparib (+)-camphorate is characterised by XRPD diffraction angles at 2θ values of 16.2°, 17.5°, 20.0°, 13.4°, 15.2°, 20.4°, 21.6° and 24.0°. In embodiments, a crystalline form (crystalline Form 1) of niraparib (+)-camphorate is characterised by XRPD diffraction angles at 2θ values of 16.2°, 17.5°, 20.0°, 13.4°, 15.2°, 20.4°, 21.6°, 24.0° and 11.7°. In embodiments, a crystalline form (crystalline Form 1) of niraparib (+)-camphorate is characterised by XRPD diffraction angles at 2θ values of 16.2°, 17.5°, 20.0°, 13.4°, 15.2°, 20.4°, 21.6°, 24.0°, 11.7° and 18.0°.

In embodiments, a crystalline form (crystalline Form 1) of niraparib (+)-camphorate is characterised by one or more (e.g. ten, eleven, twelve, thirteen, fourteen or fifteen) XRPD diffraction angles at 2θ values of 16.2°, 17.5°, 20.0°, 13.4°, 15.2°, 20.4°, 21.6°, 24.0°, 11.7°, 18.0°, 22.8°, 18.9°, 14.5°, 14.1° and 14.8°. In other embodiments, a crystalline form (crystalline Form 1) of niraparib (+)-camphorate is characterised by at least ten; at least eleven; at least twelve; at least thirteen; or at least fourteen XRPD diffraction angles at 2θ values of 16.2°, 17.5°, 20.0°, 13.4°, 15.2°, 20.4°, 21.6°, 24.0°, 11.7°, 18.0°, 22.8°, 18.9°, 14.5°, 14.1° and/or 14.8°. In other embodiments, a crystalline form (crystalline Form 1) of niraparib (+)-camphorate is characterised by XRPD diffraction angles at 2θ values of 16.2°, 17.5°, 20.0°, 13.4°, 15.2°, 20.4°, 21.6°, 24.0°, 11.7°, 18.0°, 22.8°, 18.9°, 14.5°, 14.1° and 14.8°.

In embodiments, a crystalline form (crystalline Form 1) of niraparib (+)-camphorate is characterised by one or more (e.g. fifteen, sixteen, seventeen, eighteen, nineteen or twenty) XRPD diffraction angles at 2θ values of 16.2°, 17.5°, 20.0°, 13.4°, 15.2°, 20.4°, 21.6°, 24.0°, 11.7°, 18.0°, 22.8°, 18.9°, 14.5°, 14.1°, 14.8°, 27.6°, 26.9°, 6.5°, 22.3° and/or 24.5°. In other embodiments, a crystalline form (crystalline Form 1) of niraparib (+)-camphorate is characterised by at least fifteen; at least sixteen; at least seventeen; at least eighteen; or at least nineteen XRPD diffraction angles at 2θ values of 16.2°, 17.5°, 20.0°, 13.4°, 15.2°, 20.4°, 21.6°, 24.0°, 11.7°, 18.0°, 22.8°, 18.9°, 14.5°, 14.1°, 14.8°, 27.6°, 26.9°, 6.5°, 22.3° and/or 24.5°. In other embodiments, a crystalline form (crystalline Form 1) of niraparib (+)-camphorate is characterised by XRPD diffraction angles at 2θ values of 16.2°, 17.5°, 20.0°, 13.4°, 15.2°, 20.4°, 21.6°, 24.0°, 11.7°, 18.0°, 22.8°, 18.9°, 14.5°, 14.1°, 14.8°, 27.6°, 26.9°, 6.5°, 22.3° and 24.5°.

In any of the above-mentioned embodiments, the XRPD pattern of a crystalline form (crystalline Form 1) of niraparib (+)-camphorate may contain one or more diffraction angles at 2θ values of 14.8°, 18.0°, 22.8° and 27.6°. In embodiments, the XRPD pattern of a crystalline form (crystalline Form 1) of niraparib (+)-camphorate contains at least two diffraction angles at 2θ values of 14.8°, 18.0°, 22.8° and/or 27.6°. In other embodiments, the XRPD pattern of a crystalline form (crystalline Form 1) of niraparib (+)-camphorate contains at least three diffraction angles at 2θ values of 14.8°, 18.0°, 22.8° and/or 27.6°.

In embodiments, the XRPD pattern of a crystalline form (crystalline Form 1) of niraparib (+)-camphorate salt contains diffraction angles at 2θ values of 18.0° and/or 22.8°. In other embodiments, the XRPD pattern of a crystalline form (crystalline Form 1) of niraparib (+)-camphorate salt contains diffraction angles at 2θ values of 14.8°, 18.0° and 22.8°. In other embodiments, the XRPD pattern of a crystalline form (crystalline Form 1) of niraparib (+)-camphorate salt contains diffraction angles at 2θ values of 18.0°, 22.8° and 27.6°. In other embodiments, the XRPD pattern of a crystalline form (crystalline Form 1) of niraparib (+)-camphorate salt contains diffraction angles at 2θ values of 14.8°, 18.0°, 22.8° and 27.6°.

In embodiments, a crystalline form (crystalline Form 1) of niraparib (+)-camphorate is characterised by XRPD diffraction angles having 2θ values (and, optionally, relative intensity values) substantially as recited in Table 1 of Example 4. In embodiments, the position of an XRPD diffraction angle is within ±0.2000° 2θ of the value specified in Table 1 and/or the d-spacing is within ±0.20000 Å or 0.10000 Å of the value specified in Table 1. In embodiments, the height and/or the area of the diffraction angle is within ±10% or ±5% of the value specified in Table 1. In embodiments, the relative intensity is within ±10% or ±5% of the value specified in Table 1

Figure 3:
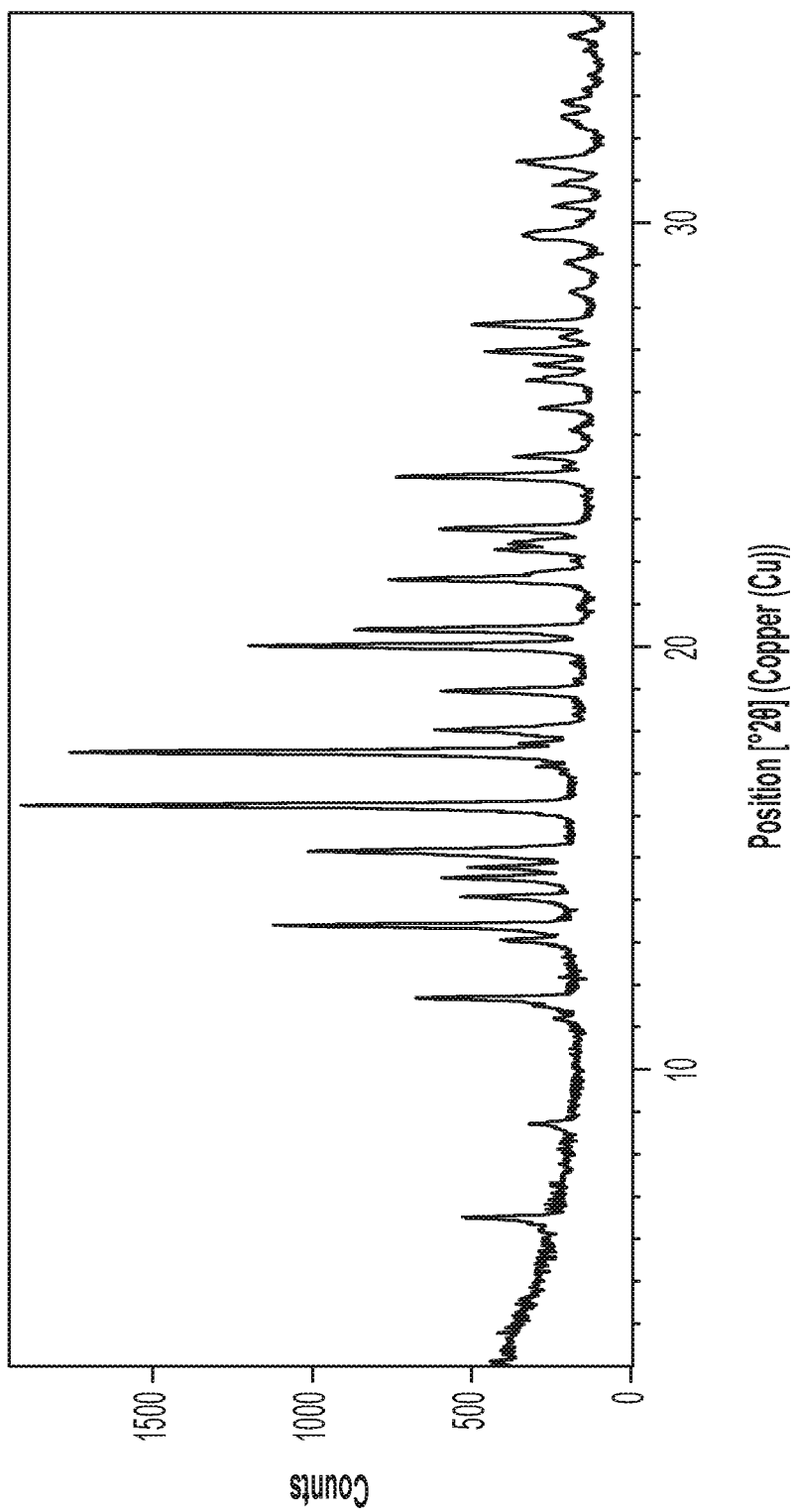
FIG. 3 shows an exemplary XRPD pattern for the crystalline Form 1 of the (1R,3S)-(+)-camphorate salt of 2-{4-[(3S)-piperidin-3-yl]phenyl}-2H-indazole-7-carboxamide (niraparib).
Figure 4:
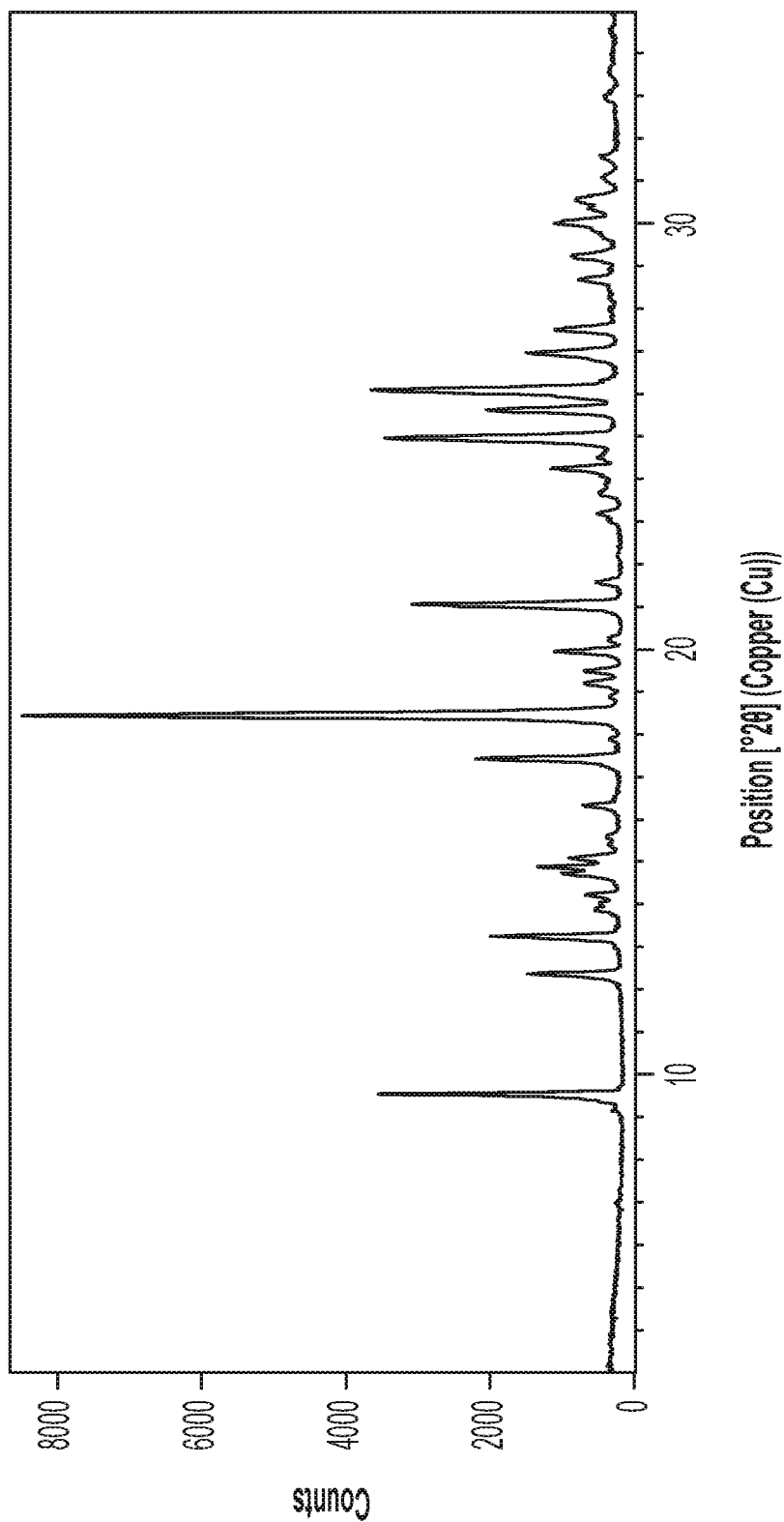
FIG. 4 shows an exemplary XRPD pattern for the crystalline Form 1 of the (1R,3S)-(+)-camphorate salt of 2-{4-[(3S)-piperidin-3-yl]phenyl}-2H-indazole-7-carboxamide (niraparib) after storage at 40° C. and 75% relative humidity for 24 h.

In embodiments, a crystalline form (crystalline Form 1) of niraparib (+)-camphorate is characterised by the XRPD pattern shown (or substantially as shown) in FIG. 3.

In embodiments, a crystalline form (crystalline Form 1) of niraparib (+)-camphorate is characterised by a melting point of about 260° C. to about 270° C. In embodiments, a crystalline form (crystalline Form 1) of niraparib (+)-camphorate is characterised by a melting point of about 264° C.

For example, a crystalline form (crystalline Form 1) of niraparib (+)-camphorate may be characterised by a DSC thermogram in which the onset of melting (endothermic peak) is about 264° C. and/or wherein the peak minimum is about 268° C. In embodiments, a crystalline form (crystalline Form 1) of niraparib (+)-camphorate may be characterised by having a DSC thermogram as shown (or substantially as shown) in FIG. 5.

In embodiments, a crystalline form (crystalline Form 1) of niraparib (+)-camphorate is characterised by having an infra-red spectrum which includes a peak at about 3359 cm$^{-1}$, a peak at about 1693 cm$^{-1}$ and a peak at about 1649 cm$^{-1}$ e.g. when measured using a FT-IR method as described herein. In embodiments, a crystalline form (crystalline Form 1) of niraparib (+)-camphorate is characterised by having an FT-IR spectrum as shown (or substantially as shown) in FIG. 2.

In embodiments, a crystalline form (crystalline Form 1) of niraparib (+)-camphorate is characterised by not being hygroscopic. Hygroscopicity may be determined, for example, by GVS (e.g. as described in the following Examples). Thus, in embodiments, a crystalline form (crystalline Form 1) of niraparib (+)-camphorate may be characterised by adsorbing less than 1% by weight of water up to 90% relative humidity (e.g. at 25° C.). In embodiments, a crystalline form (crystalline Form 1) of niraparib (+)-camphorate is characterised by adsorbing about 0.3% by weight of water up to 90% relative humidity (e.g. at 25° C.). In embodiments, a crystalline form (crystalline Form 1) of niraparib (+)-camphorate may be characterised by the GVS thermogram shown (or substantially as shown) in FIG. 6.

In embodiments, a crystalline form (crystalline Form 1) of niraparib (+)-camphorate may be characterised by being stable under conditions of elevated temperature and/or humidity.

In embodiments, substantially all (e.g. at least 90%, at least 95%, at least 99% or about 100%) of a crystalline form (crystalline Form 1) of niraparib (+)-camphorate retains the same form (e.g. when assessed by XRPD) when exposed to 90% relative humidity at room temperature (e.g. about 25° C.). In other embodiments, substantially all (e.g. at least 90%, at least 95%, at least 99% or about 100%) of a crystalline form (crystalline Form 1) of niraparib (+)-camphorate retains the same form (e.g. when assessed by XRPD) when exposed to 90% relative humidity at elevated temperature (e.g. about 30° C., 40° C., 50° C., 60° C. or 75° C.).

The crystalline form (crystalline Form 1) of niraparib (+)-camphorate may be further characterised by any combination of the characteristic stability, melting point, FT-IR spectrum, scanning differential calorimetry thermogram, gravimetric vapour sorption thermogram or XRPD diffraction angle values as described herein.

In embodiments, the molar ratio of niraparib to camphoric acid in the salt is about 1:1.

In another embodiment, the camphorate is (1S,3R)-(-)-camphorate (referred to as "(-)-camphorate" hereinafter). The (-)-camphorate salt comprises an ionised form of (1S,3R)-(-)-camphoric acid, which has the following structure:

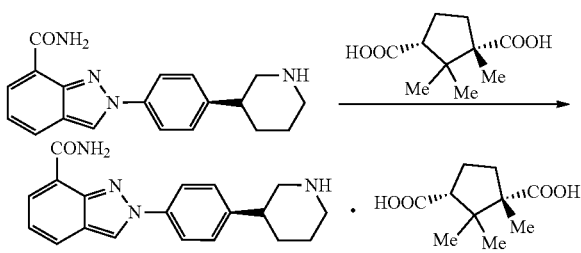

Viewed from this aspect, the invention provides 2-{4-[(3S)-piperidin-3-yl]phenyl}-2H-indazole-7-carboxamide (niraparib) (-)-camphorate, e.g. a crystalline form of niraparib (-)-camphorate. In embodiments, a crystalline form of 2-{4-[(3S)-piperidin-3-yl]phenyl}-2H-indazole-7-carboxamide (niraparib) (−)-camphorate comprises crystalline Form 1 of 2-{4-[(3S)-piperidin-3-yl]phenyl}-2H-indazole-7-carboxamide (niraparib) (−)-camphorate, e.g. as described herein.

In embodiments, a crystalline form (crystalline Form 1) niraparib (−)-camphorate is characterised by one or more (e.g. one, two, three, four or five) XRPD diffraction angles at 2θ values of 20.3°, 17.4°, 16.2°, 15.10 and 20.2°. In other embodiments, a crystalline form (crystalline Form 1) niraparib (−)-camphorate is characterised by at least two XRPD diffraction angles at 2θ values of 20.3°, 17.4°, 16.2°, 15.10 and/or 20.2°. In other embodiments, a crystalline form (crystalline Form 1) niraparib (−)-camphorate is characterised by at least three XRPD diffraction angles at 2θ values of 20.3°, 17.4°, 16.2°, 15.10 and/or 20.2°. In other embodiments, a crystalline form (crystalline Form 1) niraparib (−)-camphorate is characterised by at least four XRPD diffraction angles at 2θ values of 20.3°, 17.4°, 16.2°, 15.10 and/or 20.2°.

In embodiments, a crystalline form (crystalline Form 1) of niraparib (−)-camphorate is characterised by an XRPD diffraction angle at a 2θ value of 20.3°. In embodiments, a crystalline form (crystalline Form 1) of niraparib (−)-camphorate is characterised by XRPD diffraction angles at 2θ values of 20.3° and 17.4°. In embodiments, a crystalline form (crystalline Form 1) of niraparib (−)-camphorate is characterised by XRPD diffraction angles at 2θ values of 20.3°, 17.4° and 16.2°. In embodiments, a crystalline form (crystalline Form 1) of niraparib (−)-camphorate is characterised by XRPD diffraction angles at 2θ values of 20.3°, 17.4° and 15.1°. In embodiments, a crystalline form (crystalline Form 1) of niraparib (−)-camphorate is characterised by XRPD diffraction angles at 2θ values of 20.3°, 17.4°, 16.2° and 15.1°. In embodiments, a crystalline form of niraparib (−)-camphorate is characterised by XRPD diffraction angles at 2θ values of 20.3°, 17.4°, 16.2°, 15.1° and 20.2°.

In embodiments, a crystalline form (crystalline Form 1) of niraparib (−)-camphorate is characterised by one or more (e.g. one, two, three, four or five) XRPD diffraction angles at 2θ values of 24.4°, 19.9°, 11.6°, 22.3° and 22.2°. In other embodiments, 2θ a crystalline form (crystalline Form 1) of niraparib (−)-camphorate is characterised by at least two XRPD diffraction angles at 2θ values of 24.4°, 19.9°, 11.6°, 22.3° and/or 22.2°. In other embodiments, a crystalline form (crystalline Form 1) of niraparib (−)-camphorate is characterised by at least three XRPD diffraction angles at 2θ values of 24.4°, 19.9°, 11.6°, 22.3° and/or 22.2°. In other embodiments, a crystalline form (crystalline Form 1) of niraparib (−)-camphorate is characterised by at least four XRPD diffraction angles at 2θ values of 24.4°, 19.9°, 11.6°, 22.3° and/or 22.2°. In embodiments, a crystalline form of niraparib (−)-camphorate is characterised by XRPD diffraction angles at 2θ values of 24.4°, 19.9°, 11.6°, 22.3° and 22.2°.

In embodiments, a crystalline form (crystalline Form 1) of niraparib (−)-camphorate is characterised by one or more (e.g. six, seven, eight, nine or ten) XRPD diffraction angles at 2θ values of 20.3°, 17.4°, 16.2°, 15.1°, 20.2°, 24.4°, 19.9°, 11.6°, 22.3° and/or 22.2°. In other embodiments, a crystalline form of niraparib (−)-camphorate is characterised by at least six XRPD diffraction angles at 2θ values of 20.3°, 17.4°, 16.2°, 15.1°, 20.2°, 24.4°, 19.9°, 11.6°, 22.3° and/or 22.2°. In other embodiments, a crystalline form (crystalline Form 1) of niraparib (−)-camphorate is characterised by at least seven XRPD diffraction angles at 2θ values of 20.3°, 17.4°, 16.2°, 15.1°, 20.2°, 24.4°, 19.9°, 11.6°, 22.3° and/or 22.2°. In other embodiments, a crystalline form of niraparib (−)-camphorate is characterised by at least eight XRPD diffraction angles at 2θ values of 20.3°, 17.4°, 16.2°, 15.1°, 20.2°, 24.4°, 19.9°, 11.6°, 22.3° and/or 22.2°. In other embodiments, a crystalline form (crystalline Form 1) of niraparib (−)-camphorate is characterised by at least nine XRPD diffraction angles at 2θ values of 20.3°, 17.4°, 16.2°, 15.1°, 20.2°, 24.4°, 19.9°, 11.6°, 22.3° and/or 22.2°.

In embodiments, a crystalline form (crystalline Form 1) of niraparib (−)-camphorate is characterised by XRPD diffraction angles at 2θ values of 20.3°, 17.4°, 16.2°, 15.1°, 20.2° and 24.4°. In embodiments, a crystalline form (crystalline Form 1) of niraparib (−)-camphorate is characterised by XRPD diffraction angles at 2θ values of 20.3°, 17.4°, 16.2°, 15.1°, 20.2°, 24.4° and 19.9°. In embodiments, a crystalline form (crystalline Form 1) of niraparib (−)-camphorate is characterised by XRPD diffraction angles at 2θ values of 20.3°, 17.4°, 16.2°, 15.1°, 20.2°, 24.4°, 19.9° and 11.6°. In embodiments, a crystalline form (crystalline Form 1) of niraparib (−)-camphorate is characterised by XRPD diffraction angles at 2θ values of 20.3°, 17.4°, 16.2°, 15.1°, 20.2°, 24.4°, 19.9°, 11.6° and 22.3°. In embodiments, a crystalline form (crystalline Form 1) of niraparib (−)-camphorate is characterised by XRPD diffraction angles at 2θ values of 20.3°, 17.4°, 16.2°, 15.1°, 20.2°, 24.4°, 19.9°, 11.6°, 22.3° and 22.2°.

In embodiments, a crystalline form (crystalline Form 1) of niraparib (−)-camphorate is characterised by one or more (e.g. ten, eleven, twelve, thirteen, fourteen or fifteen) XRPD diffraction angles at 2θ values of 20.3°, 17.4°, 16.2°, 15.1°, 20.2°, 24.4°, 19.9°, 11.6°, 22.3°, 22.2°, 13.4°, 16.0°, 26.9°, 6.5° and 23.9°. In other embodiments, a crystalline form (crystalline Form 1) of niraparib (−)-camphorate is characterised by at least ten; at least eleven; at least twelve; at least thirteen; or at least fourteen XRPD diffraction angles at 2θ values of 20.3°, 17.4°, 16.2°, 15.1°, 20.2°, 24.4°, 19.9°, 11.6°, 22.3°, 22.2°, 13.4°, 16.0°, 26.9°, 6.5° and/or 23.9°. In other embodiments, a crystalline form (crystalline Form 1) of niraparib (−)-camphorate is characterised by XRPD diffraction angles at 2θ values of 20.3°, 17.4°, 16.2°, 15.1°, 20.2°, 24.4°, 19.9°, 11.6°, 22.3°, 22.2°, 13.4°, 16.0°, 26.9°, 6.5° and 23.9°.

In embodiments, a crystalline form (crystalline Form 1) of niraparib (−)-camphorate is characterised by one or more (e.g. fifteen, sixteen, seventeen, eighteen, nineteen or twenty) XRPD diffraction angles at 2θ values of 20.3°, 17.4°, 16.2°, 15.1°, 20.2°, 24.4°, 19.9°, 11.6°, 22.3°, 22.2°, 13.4°, 16.0°, 26.9°, 6.5°, 23.9°, 18.9°, 14.5°, 14.0°, 21.9° and 21.5°. In other embodiments, a crystalline form of niraparib (−)-camphorate is characterised by at least fifteen; at least sixteen; at least seventeen; at least eighteen; or at least nineteen XRPD diffraction angles at 2θ values of 20.3°, 17.4°, 16.2°, 15.1°, 20.2°, 24.4°, 19.9°, 11.6°, 22.3°, 22.2°, 13.4°, 16.0°, 26.9°, 6.5°, 23.9°, 18.9°, 14.5°, 14.0°, 21.9° and/or 21.5°. In other embodiments, a crystalline form (crystalline Form 1) of niraparib (−)-camphorate is characterised by XRPD diffraction angles at 2θ values of 20.3°, 17.4°, 16.2°, 15.1°, 20.2°, 24.4°, 19.9°, 11.6°, 22.3°, 22.2°, 13.4°, 16.0°, 26.9°, 6.5°, 23.9°, 18.9°, 14.5°, 14.0°, 21.9° and 21.5°.

In any of the above-mentioned embodiments, the XRPD pattern of a crystalline form (crystalline Form 1) of niraparib (−)-camphorate may contain diffraction angles at 2θ values of 16.0° and/or 21.9°. In embodiments, the XRPD pattern of a crystalline form (crystalline Form 1) of niraparib (−)-camphorate contains a diffraction angle at a 2θ value of 16.0°. In other embodiments, the XRPD pattern of a crystalline form (crystalline Form 1) of niraparib (−)-camphorate contains a diffraction angle at a 2θ value of 21.9°. In other embodiments, the XRPD pattern of a crystalline form (crystalline Form 1) of niraparib (−)-camphorate contains diffraction angles at 2θ values of 16.0° and 21.9°.

In embodiments, a crystalline form (crystalline Form 1) of niraparib (−)-camphorate is characterised by XRPD diffraction angles having 2θ values (and, optionally, relative intensity values) substantially as recited in Table 2 of Example 4. In embodiments, the position of an XRPD diffraction angle is within +0.2000° 2θ of the value specified in Table 2 and/or the d-spacing is within +0.20000 Å or 0.10000 Å of the value specified in Table 2. In embodiments, the height and/or the area of the diffraction angle is within ±10% or ±5% of the value specified in Table 2. In embodiments, the relative intensity is within ±10% or ±5% of the value specified in Table 2.

Figure 9:
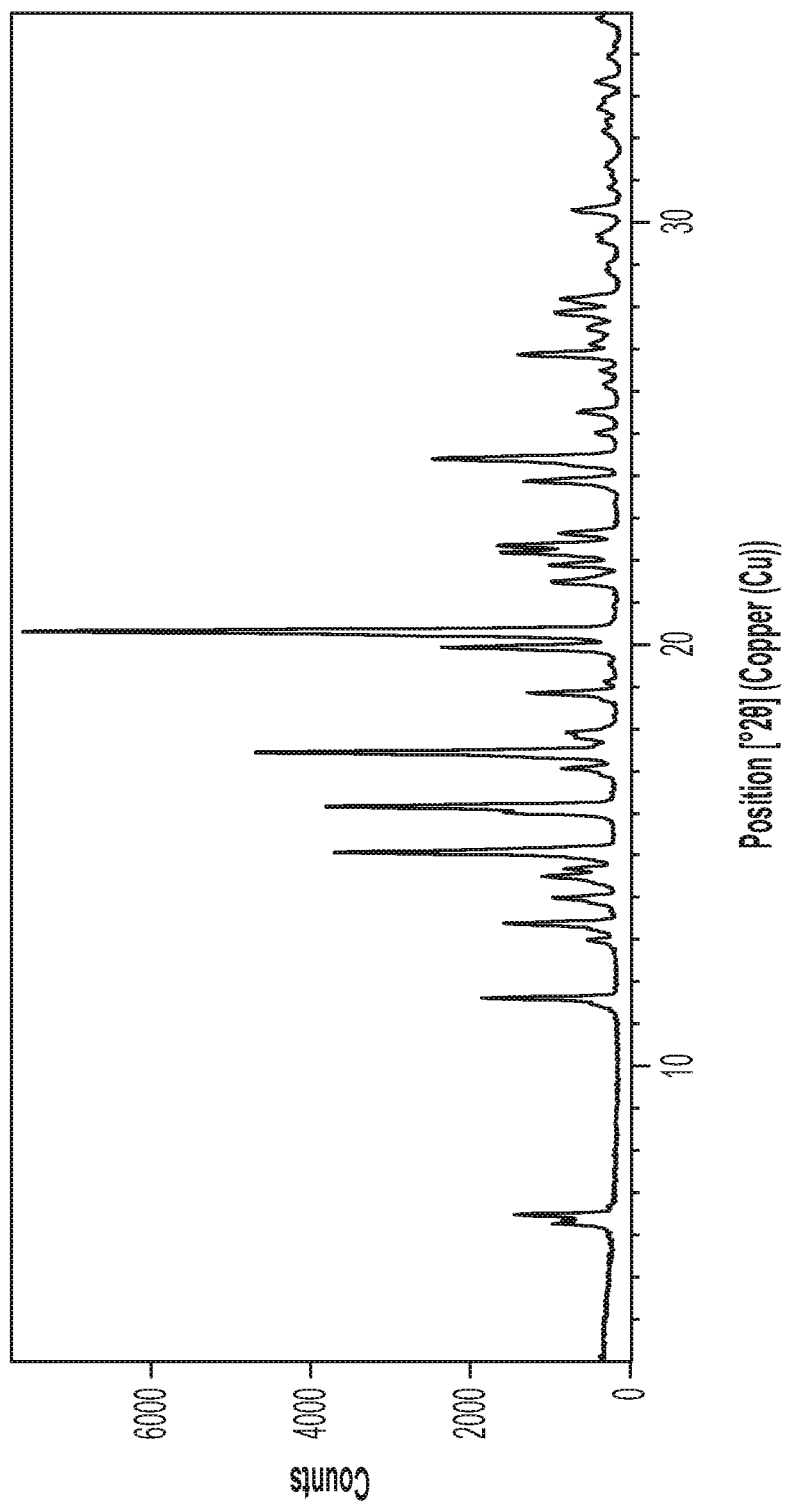
FIG. 9 shows an exemplary XRPD pattern for the crystalline Form 1 of the (1S,3R)-(−)-camphorate salt of 2-{4-[(3S)-piperidin-3-yl]phenyl}-2H-indazole-7-carboxamide (niraparib).
Figure 10:
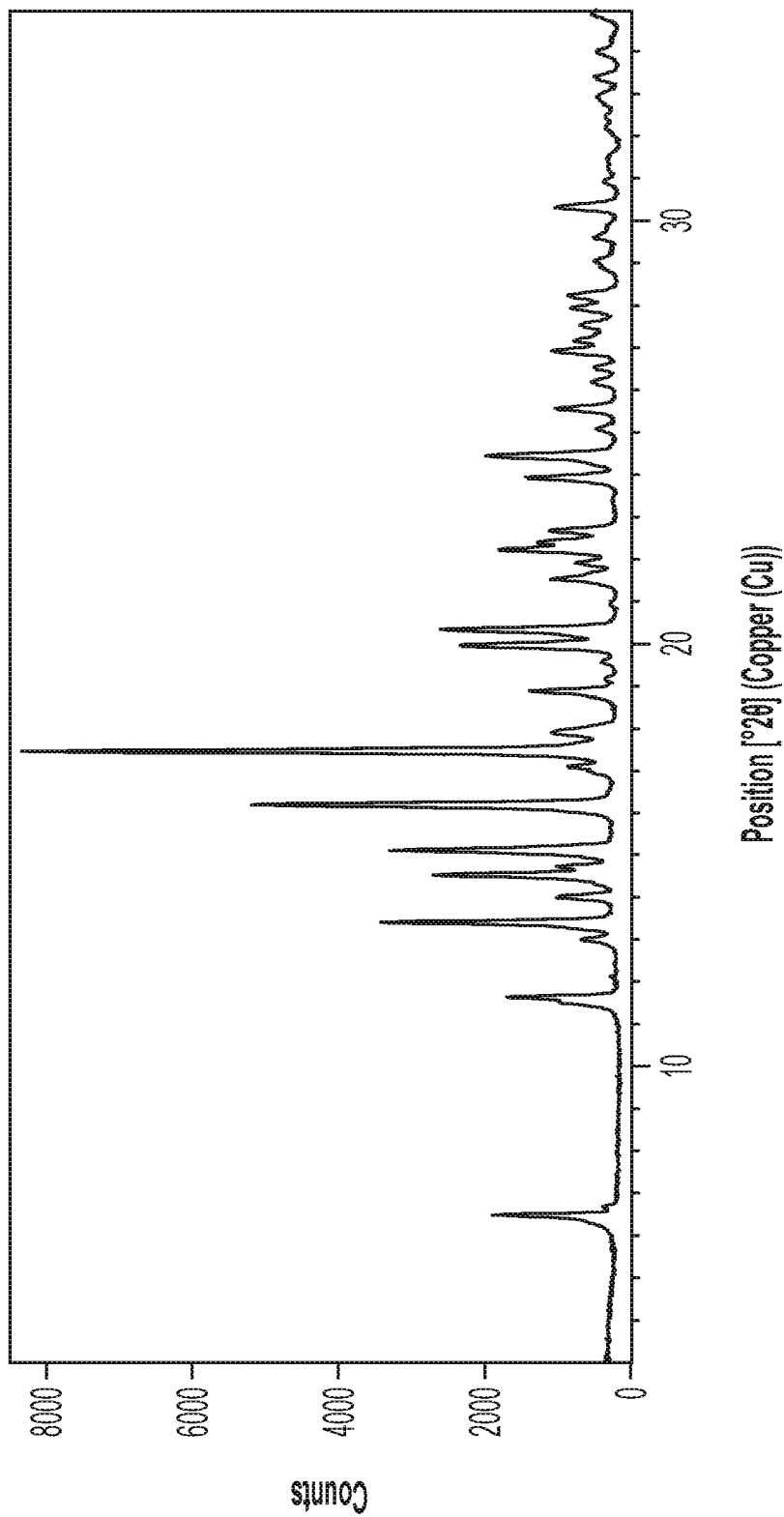
FIG. 10 shows an exemplary XRPD pattern for the crystalline Form 1 of the (1S,3R)-(−)-camphorate salt of 2-{4-[(3S)-piperidin-3-yl]phenyl}-2H-indazole-7-carboxamide (niraparib) after storage at 40° C. and 75% relative humidity for 24h.

In embodiments, a crystalline form (crystalline Form 1) of niraparib (−)-camphorate is characterised by the XRPD pattern shown (or substantially as shown) in FIG. 9.

In embodiments, a crystalline form (crystalline Form 1) of niraparib (−)-camphorate is characterised by a melting point of about 220° C. to about 230° C. In embodiments, a crystalline form (crystalline Form 1) of niraparib (−)-camphorate is characterised by a melting point of about 226° C.

For example, a crystalline form (crystalline Form 1) of niraparib (−)-camphorate may be characterised by a DSC thermogram in which the onset of melting (endothermic peak) is about 226° C. and/or wherein the peak minimum is about 230° C. In embodiments, a crystalline form (crystalline Form 1) of niraparib (−)-camphorate may be characterised by having a DSC thermogram as shown (or substantially as shown) in FIG. 11.

In embodiments, a crystalline form (crystalline Form 1) of niraparib (−)-camphorate is characterised by having an infra-red spectrum which includes a peak at about 3367 cm$^{-1}$, a peak at about 1693 cm$^{-1}$ and a peak at about 1648 cm$^{-1}$, e.g. when measured using a FT-IR method as described herein. In embodiments, a crystalline form (crystalline Form 1) of niraparib (−)-camphorate is characterised by having an FT-IR spectrum as shown (or substantially as shown) in FIG. 8.

In embodiments, a crystalline form (crystalline Form 1) of niraparib (−)-camphorate is characterised by not being hygroscopic. Hygroscopicity may be determined, for example, by GVS (e.g. as described in the following Examples). Thus, in embodiments, a crystalline form (crystalline Form 1) of niraparib (−)-camphorate may be characterised by adsorbing less than 1% by weight of water up to 90% relative humidity (e.g. at 25° C.). In embodiments, a crystalline form (crystalline Form 1) of niraparib (−)-camphorate is characterised by adsorbing about 0.2% by weight of water up to 90% relative humidity (e.g. at 25° C.). In embodiments, a crystalline form (crystalline Form 1) of niraparib (−)-camphorate may be characterised by the GVS thermogram shown (or substantially as shown) in FIG. 12.

In embodiments, a crystalline form (crystalline Form 1) of niraparib (−)-camphorate may be characterised by being stable under conditions of elevated temperature and/or humidity.

In embodiments, substantially all (e.g. at least 90%, at least 95%, at least 99% or about 100%) of a crystalline form (crystalline Form 1) of niraparib (−)-camphorate retains the same form (e.g. when assessed by XRPD) when exposed to 90% relative humidity at room temperature (e.g. about 25° C.). In other embodiments, substantially all (e.g. at least 90%, at least 95%, at least 99% or about 100%) of a crystalline form (crystalline Form 1) of niraparib (−)-camphorate retains the same form (e.g. when assessed by XRPD) when exposed to 90% relative humidity at elevated temperature (e.g. about 30° C., 40° C., 50° C., 60° C. or 75° C.).

A crystalline form (crystalline Form 1) of niraparib (−)-camphorate may be further characterised by any combination of the characteristic stability, melting point, FT-IR spectrum, scanning differential calorimetry thermogram, gravimetric vapour sorption thermogram or XRPD diffraction angle values as described herein.

In embodiments, the molar ratio of niraparib to camphoric acid in the salt is about 1:1.

Niraparib Mandelate

In another aspect, the invention provides a mandelate salt of 2-{4-[(3S)-piperidin-3-yl]phenyl}-2H-indazole-7-carboxamide (niraparib) ("niraparib mandelate"). A mandelate salt comprises an ionised form of mandelic acid, α-hydroxyphenylacetic acid. In a preferred aspect, the invention provides a crystalline form of 2-{4-[(3S)-piperidin-3-yl]phenyl}-2H-indazole-7-carboxamide (niraparib) mandelate.

The mandelate salt may be selected from (R)-(−)-mandelate, (S)-(+)-mandelate, (rac)-mandelate, and mixtures thereof.

In one embodiment, the mandelate is (R)-(−)-mandelate. The (R)-(−)-mandelate salt comprises an ionised form of (R)-(−)-mandelic acid, which has the following structure:

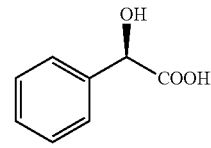 [SMILES: O=C(O)[C@H](O)c1ccccc1]

Viewed from this aspect, the invention provides 2-{4-[(3S)-piperidin-3-yl]phenyl}-2H-indazole-7-carboxamide (niraparib) (R)-(−)-mandelate, e.g. a crystalline form of 2-{4-[(3S)-piperidin-3-yl]phenyl}-2H-indazole-7-carboxamide (niraparib) (R)-(−)-mandelate. In embodiments, a crystalline form of 2-{4-[(3S)-piperidin-3-yl]phenyl}-2H-indazole-7-carboxamide (niraparib) (R)-(−)-mandelate comprises Form 1 2-{4-[(3S)-piperidin-3-yl]phenyl}-2H-indazole-7-carboxamide (niraparib) (R)-(−)-mandelate, e.g. as described herein.

In embodiments, a crystalline form (crystalline Form 1) of niraparib (R)-(−)-mandelate is characterised by one or more (e.g. one, two, three, four or five) XRPD diffraction angles at 2θ values of 18.5°, 16.4°, 17.4°, 8.6° and/or 17.6°. In other embodiments, a crystalline form (crystalline Form 1) of niraparib (R)-(−)-mandelate is characterised by at least two XRPD diffraction angles at 2θ values of 18.5°, 16.4°, 17.4°, 8.6° and/or 17.6°. In other embodiments, a crystalline form of niraparib (R)-(−)-mandelate is characterised by at least three XRPD diffraction angles at 2θ values of 18.5°, 16.4°, 17.4°, 8.6° and/or 17.6°. In other embodiments, a crystalline form (crystalline Form 1) of niraparib (R)-(−)-mandelate is characterised by at least four XRPD diffraction angles at 2θ values of 18.5°, 16.4°, 17.4°, 8.6° and/or 17.6°.

In embodiments, a crystalline form of niraparib (R)-(−)-mandelate is characterised by an XRPD diffraction angle at a 2θ value of 18.5°. In embodiments, a crystalline form (crystalline Form 1) of niraparib (R)-(−)-mandelate is characterised by an XRPD diffraction angle at a 2θ value of 16.4°. In embodiments, a crystalline form (crystalline Form 1) of niraparib (R)-(−)-mandelate is characterised by XRPD diffraction angles at 2θ values of 18.5° and 16.4°. In embodiments, a crystalline form (crystalline Form 1) of niraparib (R)-(−)-mandelate is characterised by XRPD diffraction angles at 2θ values of 18.5°, 16.4° and 17.4°. In embodiments, a crystalline form (crystalline Form 1) of niraparib (R)-(−)-mandelate is characterised by XRPD diffraction angles at 2θ values of 18.5°, 16.4°, 17.4° and 8.6°. In embodiments, a crystalline form (crystalline Form 1) of niraparib (R)-(−)-mandelate is characterised by XRPD diffraction angles at 2θ values of 18.5°, 16.4°, 17.4°, 8.6° and 17.6°.

In embodiments, a crystalline form (crystalline Form 1) of niraparib (R)-(−)-mandelate is characterised by one or more (e.g. one, two, three, four or five) XRPD diffraction angles at 2θ values of 8.7°, 18.4°, 25.10, 27.6° and/or 13.7°. In other embodiments, a crystalline form (crystalline Form 1) of niraparib (R)-(−)-mandelate is characterised by at least two XRPD diffraction angles at 2θ values of 8.7°, 18.4°, 25.10, 27.6° and/or 13.7°. In other embodiments, a crystalline form (crystalline Form 1) of niraparib (R)-(−)-mandelate is characterised by at least three XRPD diffraction angles at 2θ values of 8.7°, 18.4°, 25.1°, 27.6° and/or 13.7°. In other embodiments, a crystalline form (crystalline Form 1) of niraparib (R)-(−)-mandelate is characterised by at least four XRPD diffraction angles at 2θ values of 8.7°, 18.4°, 25.10, 27.6° and/or 13.7°. In embodiments, a crystalline form of niraparib (R)-(−)-mandelate is characterised by XRPD diffraction angles at 2θ values of 8.7°, 18.4°, 25.1°, 27.6° and 13.7°.

In embodiments, a crystalline form (crystalline Form 1) of niraparib (R)-(−)-mandelate is characterised by one or more (e.g. six, seven, eight, nine or ten) XRPD diffraction angles at 2θ values of 18.5°, 16.4°, 17.4°, 8.6°, 17.6°, 8.7°, 18.4°, 25.10, 27.6° and/or 13.7°. In other embodiments, a crystalline form (crystalline Form 1) of niraparib (R)-(−)-mandelate is characterised by at least six XRPD diffraction angles at 2θ values of 18.5°, 16.4°, 17.4°, 8.6°, 17.6°, 8.7°, 18.4°, 25.10, 27.6° and/or 13.7°. In other embodiments, a crystalline form (crystalline Form 1) of niraparib (R)-(−)-mandelate is characterised by at least seven XRPD diffraction angles at 2θ values of 18.5°, 16.4°, 17.4°, 8.6°, 17.6°, 8.7°, 18.4°, 25.10, 27.6° and/or 13.7°. In other embodiments, a crystalline form (crystalline Form 1) of niraparib (R)-(−)-mandelate is characterised by at least eight XRPD diffraction angles at 2θ values of 18.5°, 16.4°, 17.4°, 8.6°, 17.6°, 8.7°, 18.4°, 25.1°, 27.6° and/or 13.7°. In other embodiments, a crystalline form of niraparib (R)-(−)-mandelate is characterised by at least nine XRPD diffraction angles at 2θ values of 18.5°, 16.4°, 17.4°, 8.6°, 17.6°, 8.7°, 18.4°, 25.1°, 27.6° and/or 13.7°.

In embodiments, a crystalline form of niraparib (R)-(−)-mandelate is characterised by XRPD diffraction angles at 2θ values of 18.5°, 16.4°, 17.4°, 8.6°, 17.6° and 8.7°. In embodiments, a crystalline form of niraparib (R)-(−)-mandelate is characterised by XRPD diffraction angles at 2θ values of 18.5°, 16.4°, 17.4°, 8.6°, 17.6°, 8.7° and 18.4°. In embodiments, a crystalline form (crystalline Form 1) of niraparib (R)-(−)-mandelate is characterised by XRPD diffraction angles at 2° values of 18.5°, 16.4°, 17.4°, 8.6°, 17.6°, 8.7°, 18.4° and 25.1°. In embodiments, a crystalline form (crystalline Form 1) of niraparib (R)-(−)-mandelate is characterised by XRPD diffraction angles at 2θ values of 18.5°, 16.4°, 17.4°, 8.6°, 17.6°, 8.7°, 18.4°, 25.1° and 27.6°. In embodiments, a crystalline form (crystalline Form 1) of niraparib (R)-(−)-mandelate is characterised by XRPD diffraction angles at 2θ values of 18.5°, 16.4°, 17.4°, 8.6°, 17.6°, 8.7°, 18.4°, 25.1°, 27.6° and 13.7°.

In embodiments, a crystalline form (crystalline Form 1) of niraparib (R)-(−)-mandelate is characterised by one or more (e.g. ten, eleven, twelve, thirteen, fourteen or fifteen) XRPD diffraction angles at 2θ values of 18.5°, 16.4°, 17.4°, 8.6°, 17.6°, 8.7°, 18.4°, 25.1°, 27.6°, 13.7°, 8.4°, 28.7°, 28.0°, 4.3° and/or 21.5°. In other embodiments, a crystalline form (crystalline Form 1) of niraparib (R)-(−)-mandelate is characterised by at least ten; at least eleven; at least twelve; at least thirteen; or at least fourteen XRPD diffraction angles at 2θ values of 18.5°, 16.4°, 17.4°, 8.6°, 17.6°, 8.7°, 18.4°, 25.1°, 27.6°, 13.7°, 8.4°, 28.7°, 28.0°, 4.3° and/or 21.5°. In other embodiments, a crystalline form (crystalline Form 1) of niraparib (R)-(−)-mandelate is characterised by XRPD diffraction angles at 2θ values of 18.5°, 16.4°, 17.4°, 8.6°, 17.6°, 8.7°, 18.4°, 25.1°, 27.6°, 13.7°, 8.4°, 28.7°, 28.0°, 4.3° and 21.5°.

In embodiments, a crystalline form (crystalline Form 1) of niraparib (R)-(−)-mandelate is characterised by one or more (e.g. fifteen, sixteen, seventeen, eighteen, nineteen or twenty) XRPD diffraction angles at 2θ values of 18.5°, 16.4°, 17.4°, 8.6°, 17.6°, 8.7°, 18.4°, 25.1°, 27.6°, 13.7°, 8.4°, 28.7°, 28.0°, 4.3°, 21.5°, 27.3°, 14.1°, 27.7°, 12.4° and/or 16.1°. In other embodiments, a crystalline form (crystalline Form 1) of niraparib (R)-(−)-mandelate is characterised by at least fifteen; at least sixteen; at least seventeen; at least eighteen; or at least nineteen XRPD diffraction angles at 2θ values of 18.5°, 16.4°, 17.4°, 8.6°, 17.6°, 8.7°, 18.4°, 25.1°, 27.6°, 13.7°, 8.4°, 28.7°, 28.0°, 4.3°, 21.5°, 27.3°, 14.1°, 27.7°, 12.4° and/or 16.1°. In other embodiments, a crystalline form (crystalline Form 1) of niraparib (R)-(−)-mandelate is characterised by XRPD diffraction angles at 2θ values of 18.5°, 16.4°, 17.4°, 8.6°, 17.6°, 8.7°, 18.4°, 25.1°, 27.6°, 13.7°, 8.4°, 28.7°, 28.0°, 4.3°, 21.5°, 27.3°, 14.1°, 27.7°, 12.4° and 16.1°.

In embodiments, a crystalline form (crystalline Form 1) of niraparib (R)-(−)-mandelate is characterised by XRPD diffraction angles having 2θ values (and, optionally, relative intensity values) substantially as recited in Table 3 of Example 4. In embodiments, the position of an XRPD diffraction angle is within ±0.2000° 2θ of the value specified in Table 3 and/or the d-spacing is within ±0.20000 Å or ±0.10000 Å of the value specified in Table 3. In embodiments, the height and/or the area of the diffraction angle is within ±10% or ±5% of the value specified in Table 3. In embodiments, the relative intensity is within ±10% or ±5% of the value specified in Table 3.

Figure 15:
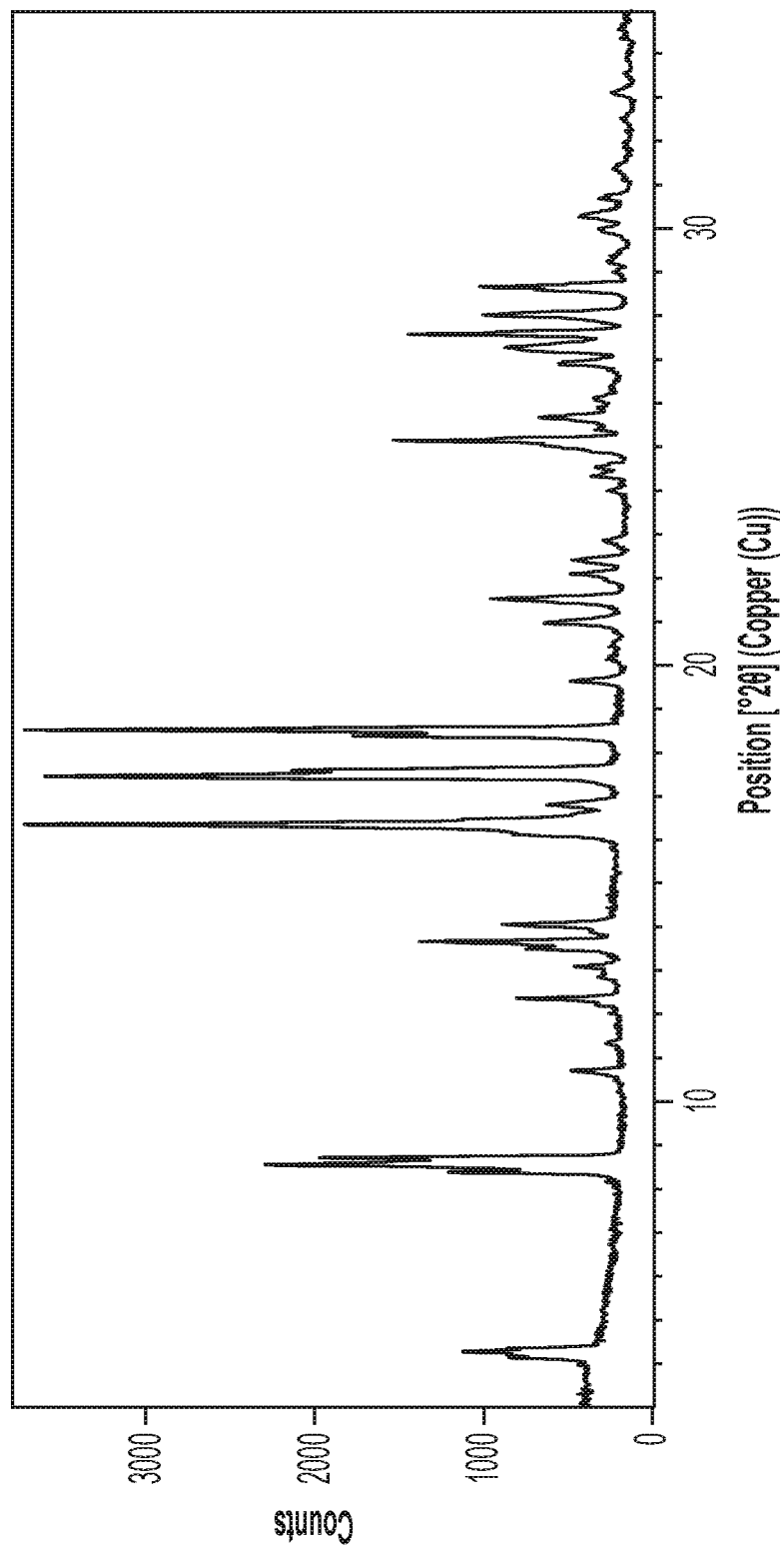
FIG. 15 shows an exemplary XRPD pattern for the crystalline Form 1 of the (R)-(−)-mandelate salt of 2-{4-[(3S)-piperidin-3-yl]phenyl}-2H-indazole-7-carboxamide (niraparib).
Figure 16:
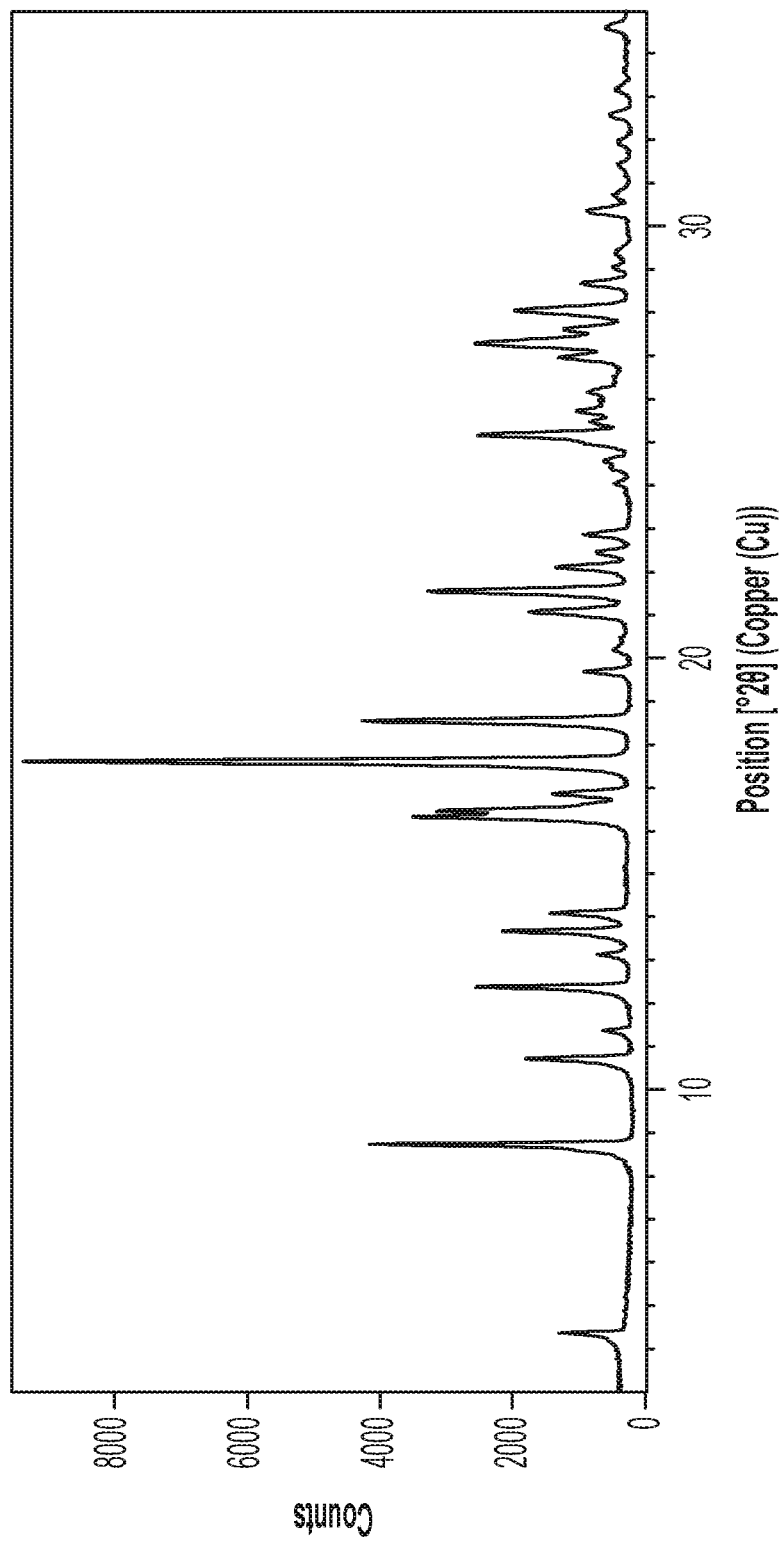
FIG. 16 shows an exemplary XRPD pattern for the crystalline Form 1 of the (R)-(−)-mandelate salt of 2-{4-[(3S)-piperidin-3-yl]phenyl}-2H-indazole-7-carboxamide (niraparib) after storage at 40° C. and 75% relative humidity for 24h.
Figure 17:
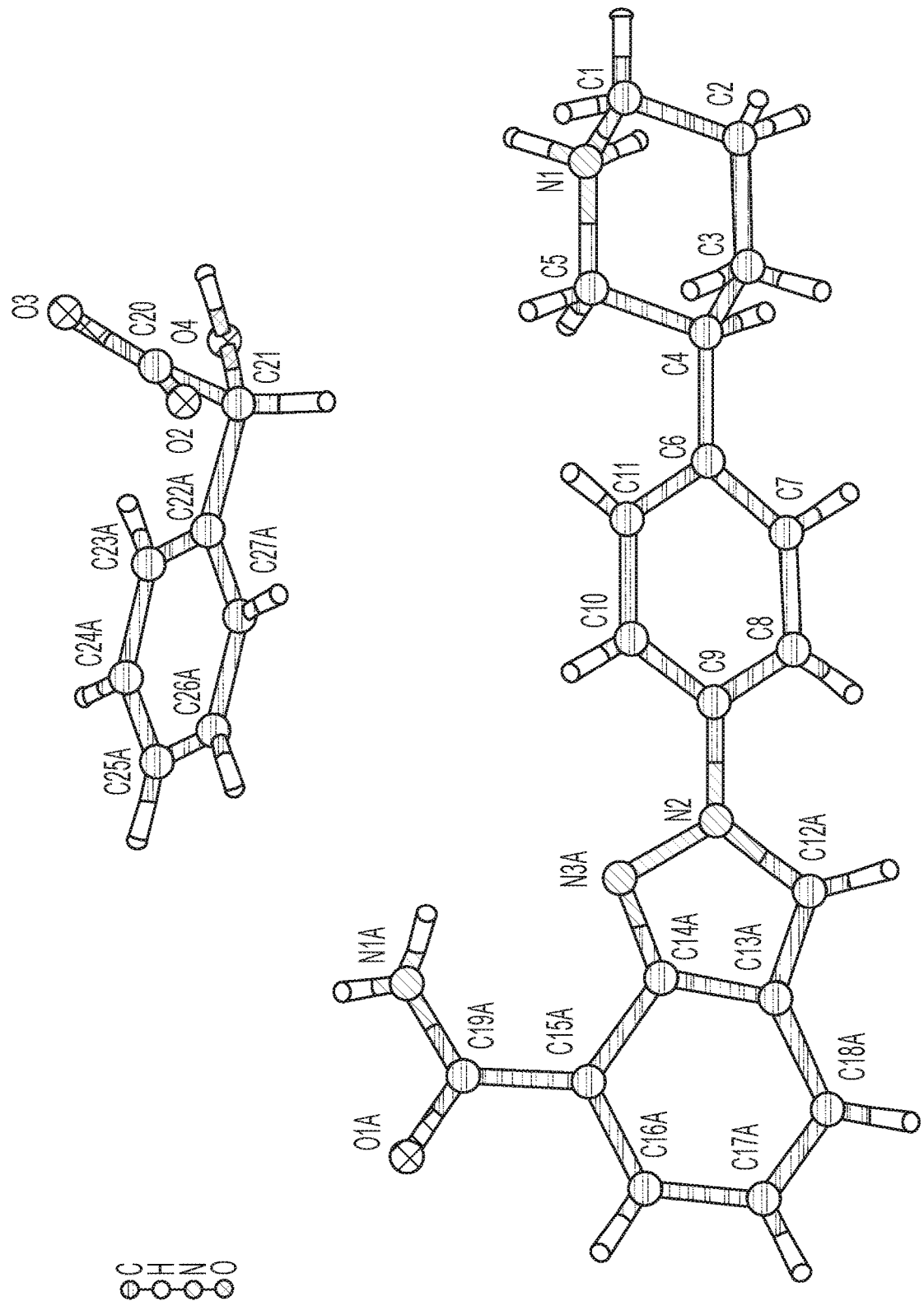
FIG. 17 shows the structure of the (R)-(−)-mandelate salt of 2-{4-[(3S)-piperidin-3-yl]phenyl}-2H-indazole-7-carboxamide (niraparib) as determined by single crystal X-ray crystallography.

In embodiments, a crystalline form (crystalline Form 1) of niraparib (R)-(−)-mandelate is characterised by the XRPD pattern shown (or substantially as shown) in FIG. 15.

In embodiments, a crystalline form (crystalline Form 1) of niraparib (R)-(−)-mandelate is characterised by a melting point of about 190° C. to about 200° C. In embodiments, a crystalline form (crystalline Form 1) of niraparib (R)-(−)-mandelate is characterised by a melting point of about 197° C.

In embodiments, a crystalline form (crystalline Form 1) of niraparib (R)-(−)-mandelate is characterised by a DSC thermogram in which the onset of melting (endothermic peak) is about 197° C. and/or wherein the peak minimum is about 201° C. In embodiments, a crystalline form (crystalline Form 1) of niraparib (R)-(−)-mandelate is characterised by having a DSC thermogram as shown (or substantially as shown) in FIG. 18.

In embodiments, a crystalline form (crystalline Form 1) of niraparib (R)-(−)-mandelate is characterised by having an infra-red spectrum which includes a peak at about 3443 cm$^{-1}$, a peak at about 3340 cm$^{-1}$, a peak at about 1671 cm$^{-1}$ and a peak at about 1638 cm$^{-1}$ e.g. when measured using a FT-IR method as described herein. In embodiments, a crystalline form (crystalline Form 1) of niraparib (R)-(−)-mandelate is characterised by having an FT-IR spectrum as shown (or substantially as shown) in FIG. 14.

In embodiments, a crystalline form (crystalline Form 1) of niraparib (R)-(−)-mandelate is characterised by not being hygroscopic. Hygroscopicity may be determined, for example, by GVS (e.g. as described in the following Examples). Thus, in embodiments, a crystalline form (crystalline Form 1) of niraparib (R)-(−)-mandelate may be characterised by adsorbing less than 1% by weight of water up to 90% relative humidity (e.g. at 25° C.). In embodiments, a crystalline form (crystalline Form 1) of niraparib (R)-(−)-mandelate is characterised by adsorbing about 0.5% by weight of water up to 90% relative humidity (e.g. at 25° C.). In embodiments, a crystalline form (crystalline Form 1) of niraparib (R)-(−)-mandelate is characterised by the DVS thermogram as shown (or substantially as shown) in FIG. 19.

In embodiments, a crystalline form (crystalline Form 1) of niraparib (R)-(−)-mandelate may be characterised by being stable under conditions of elevated temperature and/or humidity.

In embodiments, substantially all (e.g. at least 90%, at least 95%, at least 99% or about 100%) of a crystalline form (crystalline Form 1) of niraparib (R)-(−)-mandelate retains the same form (e.g. when assessed by XRPD) when exposed to 90% relative humidity at room temperature (e.g. about 25° C.). In other embodiments, substantially all (e.g. at least 90%, at least 95%, at least 99% or about 100%) of a crystalline form (crystalline Form 1) of niraparib (R)-(−)-mandelate retains the same form (e.g. when assessed by XRPD) when exposed to 90% relative humidity at elevated temperature (e.g. about 30° C., 40° C., 50° C., 60° C. or 75° C.).

Figure 18:
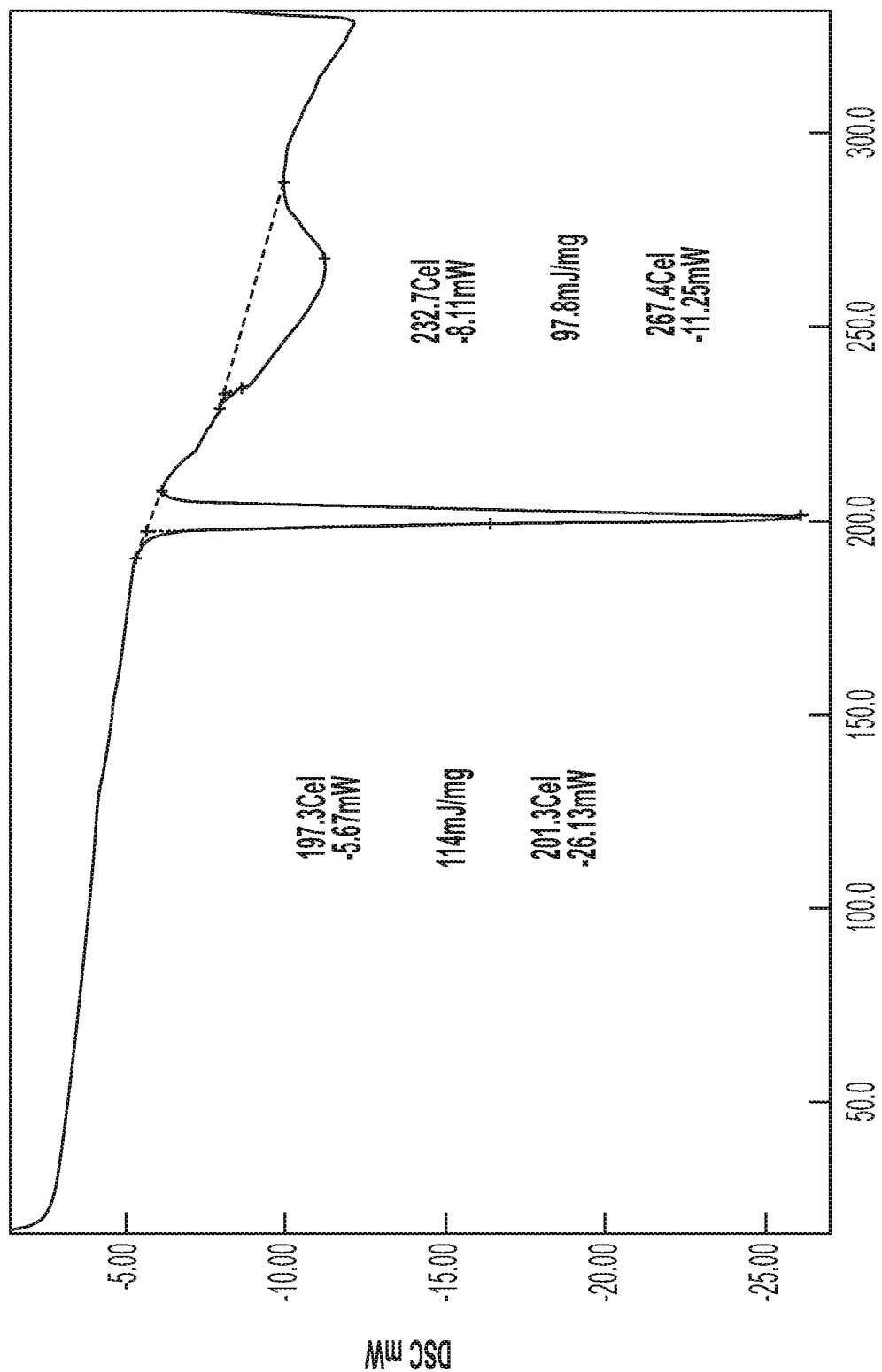
FIG. 18 shows an exemplary differential scanning calorimetry thermogram for the crystalline Form 1 of the (R)-(−)-mandelate salt of 2-{4-[(3S)-piperidin-3-yl]phenyl}-2H-indazole-7-carboxamide (niraparib).

In embodiments, a crystalline form (crystalline Form 1) of niraparib (R)-(−)-mandelate may be characterised by the structure shown (or substantially as shown) in FIG. 18.

A crystalline form (crystalline Form 1) of niraparib (R)-(−)-mandelate may be further characterised by any combination of the characteristic stability, melting point, FT-IR spectrum, scanning differential calorimetry thermogram, dynamic scanning vapour sorption thermogram, structure as determined by single crystal X-ray crystallography, or XRPD diffraction angle values as described herein.

Niraparib Camsylate

In another aspect, the invention provides a camsylate salt of 2-{4-[(3S)-piperidin-3-yl]phenyl}-2H-indazole-7-carboxamide (niraparib) ("niraparib camsylate"). A camsylate salt comprises an ionised form of 7,7-dimethyl-2-oxobicyclo[2.2.1]heptan-1-yl)methanesulfonic acid. In a preferred aspect, the invention provides crystalline 2-{4-[(3S)-piperidin-3-yl]phenyl}-2H-indazole-7-carboxamide (niraparib) camsylate.

The camsylate salt may be selected from (1S)-(+)-camsylate, (1R)-(−)-camsylate, (rac)-camsylate, and mixtures thereof.

In one embodiment, the camsylate is (1S)-(+)-camsylate. The (1S)-(+)-camsylate salt comprises an ionised form of (1S)-(+)-7,7-dimethyl-2-oxobicyclo[2.2.1]heptan-1-yl) methanesulfonic acid, which has the following structure:

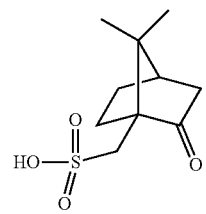

Viewed from this aspect, the invention provides 2-{4-[(3S)-piperidin-3-yl]phenyl}-2H-indazole-7-carboxamide (niraparib) (1S)-(+)-camsylate, e.g. a crystalline form of 2-{4-[(3S)-piperidin-3-yl]phenyl}-2H-indazole-7-carboxamide (niraparib) (1S)-(+)-camsylate. In embodiments, a crystalline form of 2-{4-[(3S)-piperidin-3-yl]phenyl}-2H-indazole-7-carboxamide (niraparib) (1S)-(+)-camsylate comprises Form 1 2-{4-[(3S)-piperidin-3-yl]phenyl}-2H-indazole-7-carboxamide (niraparib) (1S)-(+)-camsylate, e.g. as described herein.

In embodiments, a crystalline form (crystalline Form 1) of niraparib (1S)-(+)-camsylate is characterised by one or more (e.g. one, two, three, four or five) XRPD diffraction angles at 2θ values of 16.0°, 13.5°, 17.6°, 24.3° and/or 24.6°. In other embodiments, a crystalline form of niraparib (1S)-(+)-camsylate is characterised by at least two XRPD diffraction angles at 2θ values of 16.0°, 13.5°, 17.6°, 24.3° and/or 24.6°. In other embodiments, a crystalline form (crystalline Form 1) of niraparib (1S)-(+)-camsylate is characterised by at least three XRPD diffraction angles at 2θ values of 16.0°, 13.5°, 17.6°, 24.3° and/or 24.6°. In other embodiments, a crystalline form (crystalline Form 1) of niraparib (1S)-(+)-camsylate is characterised by at least four XRPD diffraction angles at 2θ values of 16.0°, 13.5°, 17.6°, 24.3° and/or 24.6°.

In embodiments, a crystalline form (crystalline Form 1) of niraparib (1S)-(+)-camsylate is characterised by an XRPD diffraction angle at a 2θ value of 16.0°. In embodiments, a crystalline form (crystalline Form 1) of niraparib (1S)-(+)-camsylate is characterised by XRPD diffraction angles at 2θ values of 16.0° and 13.5°. In embodiments, a crystalline form (crystalline Form 1) of niraparib (1S)-(+)-camsylate is characterised by XRPD diffraction angles at 2θ values of 16.0° and 17.6°. In embodiments, a crystalline form (crystalline Form 1) of niraparib (1S)-(+)-camsylate is characterised by XRPD diffraction angles at 2θ values of 16.0°, 13.5° and 17.6°. In embodiments, a crystalline form (crystalline Form 1) of niraparib (1S)-(+)-camsylate is characterised by XRPD diffraction angles at 2θ values of 16.0°, 13.5°, 17.6° and 24.3°. In embodiments, a crystalline form (crystalline Form 1) of niraparib (1S)-(+)-camsylate is characterised by XRPD diffraction angles at 2θ values of 16.0°, 13.5°, 17.6°, 24.3° and 24.6°.

In embodiments, a crystalline form (crystalline Form 1) of niraparib (1S)-(+)-camsylate is characterised by one or more (e.g. one, two, three, four or five) XRPD diffraction angles at 2θ values of 11.10, 16.4°, 23.7°, 16.7° and/or 20.3°. In other embodiments, a crystalline form (crystalline Form 1) of niraparib (1S)-(+)-camsylate is characterised by at least two XRPD diffraction angles at 2θ values of 11.10, 16.4°, 23.7°, 16.7° and/or 20.3°. In other embodiments, a crystalline form (crystalline Form 1) of niraparib (1S)-(+)-camsylate is characterised by at least three XRPD diffraction angles at 2θ values of 11.10, 16.4°, 23.7°, 16.7° and/or 20.3°. In other embodiments, a crystalline form (crystalline Form 1) of niraparib (1S)-(+)-camsylate is characterised by at least four XRPD diffraction angles at 2θ values of 11.10, 16.4°, 23.7°, 16.7° and/or 20.3°. In embodiments, a crystalline form (crystalline Form 1) of niraparib (1S)-(+)-camsylate is characterised by XRPD diffraction angles at 2θ values of 11.10, 16.4°, 23.7°, 16.7° and 20.3°.

In embodiments, a crystalline form (crystalline Form 1) of niraparib (1S)-(+)-camsylate is characterised by one or more (e.g. six, seven, eight, nine or ten) XRPD diffraction angles at 2θ values of 16.0°, 13.5°, 17.6°, 24.3°, 24.6°, 11.10, 16.4°, 23.7°, 16.7° and/or 20.3°. In other embodiments, a crystalline form of niraparib (1S)-(+)-camsylate is characterised by at least six XRPD diffraction angles at 2θ values of 16.0°, 13.5°, 17.6°, 24.3°, 24.6°, 11.1°, 16.4°, 23.7°, 16.7° and/or 20.3°. In other embodiments, a crystalline form (crystalline Form 1) of niraparib (1S)-(+)-camsylate is characterised by at least seven XRPD diffraction angles at 2θ values of 16.0°, 13.5°, 17.6°, 24.3°, 24.6°, 11.10, 16.4°, 23.7°, 16.7° and/or 20.3°. In other embodiments, a crystalline form (crystalline Form 1) of niraparib (1S)-(+)-camsylate is characterised by at least eight XRPD diffraction angles at 2θ values of 16.0°, 13.5°, 17.6°, 24.3°, 24.6°, 11.1°, 16.4°, 23.7°, 16.7° and/or 20.3°. In other embodiments, a crystalline form (crystalline Form 1) of niraparib (1S)-(+)-camsylate is characterised by at least nine XRPD diffraction angles at 2θ values of 16.0°, 13.5°, 17.6°, 24.3°, 24.6°, 11.10, 16.4°, 23.7°, 16.7° and/or 20.3°.

In embodiments, a crystalline form (crystalline Form 1) of niraparib (1S)-(+)-camsylate is characterised by XRPD diffraction angles at 2θ values of 16.0°, 13.5°, 17.6°, 24.3°, 24.6° and 11.1°. In embodiments, a crystalline form (crystalline Form 1) of niraparib (1S)-(+)-camsylate is characterised by XRPD diffraction angles at 2θ values of 16.0°, 13.5°, 17.6°, 24.3°, 24.6°, 11.1° and 16.4°. In embodiments, a crystalline form of niraparib (1S)-(+)-camsylate is characterised by XRPD diffraction angles at 2θ values of 16.0°, 13.5°, 17.6°, 24.3°, 24.6°, 11.1°, 16.4° and 23.7°. In embodiments, a crystalline form of niraparib (1S)-(+)-camsylate is characterised by XRPD diffraction angles at 2θ values of 16.0°, 13.5°, 17.6°, 24.3°, 24.6°, 11.1°, 16.4°, 23.7° and 16.7°. In embodiments, a crystalline form (crystalline Form 1) of niraparib (1S)-(+)-camsylate is characterised by XRPD diffraction angles at 2θ values of 16.0°, 13.5°, 17.6°, 24.3°, 24.6°, 11.1°, 16.4°, 23.7°, 16.7° and 20.3°.

In embodiments, a crystalline form (crystalline Form 1) of niraparib (1S)-(+)-camsylate is characterised by one or more (e.g. ten, eleven, twelve, thirteen, fourteen or fifteen) XRPD diffraction angles at 2θ values of 16.0°, 13.5°, 17.6°, 24.3°, 24.6°, 11.1°, 16.4°, 23.7°, 16.7°, 20.3°, 6.7°, 25.2°, 25.0°, 25.8° and/or 26.8°. In other embodiments, a crystalline form of niraparib (1S)-(+)-camsylate is characterised by at least ten; at least eleven; at least twelve; at least thirteen; or at least fourteen XRPD diffraction angles at 2θ values of 16.0°, 13.5°, 17.6°, 24.3°, 24.6°, 11.1°, 16.4°, 23.7°, 16.7°, 20.3°, 6.7°, 25.2°, 25.0°, 25.8° and/or 26.8°. In other embodiments, a crystalline form of niraparib (1S)-(+)-camsylate is characterised by XRPD diffraction angles at 2θ values of 16.0°, 13.5°, 17.6°, 24.3°, 24.6°, 11.1°, 16.4°, 23.7°, 16.7°, 20.3°, 6.7°, 25.2°, 25.0°, 25.8° and 26.8°.

In embodiments, a crystalline form (crystalline Form 1) of niraparib (1S)-(+)-camsylate is characterised by one or more (e.g. fifteen, sixteen, seventeen, eighteen, nineteen or twenty) XRPD diffraction angles at 2θ values of 16.0°, 13.5°, 17.6°, 24.3°, 24.6°, 11.1°, 16.4°, 23.7°, 16.7°, 20.3°, 6.7°, 25.2°, 25.0°, 25.8°, 26.8°, 22.8°, 9.5°, 16.9°, 14.3° and/or 7.7°. In other embodiments, a crystalline form (crystalline Form 1) of niraparib (1S)-(+)-camsylate is characterised by at least fifteen; at least sixteen; at least seventeen; at least eighteen; or at least nineteen XRPD diffraction angles at 2θ values of 16.0°, 13.5°, 17.6°, 24.3°, 24.6°, 11.1°, 16.4°, 23.7°, 16.7°, 20.3°, 6.7°, 25.2°, 25.0°, 25.8°, 26.8°, 22.8°, 9.5°, 16.9°, 14.3° and/or 7.7°. In other embodiments, a crystalline form (crystalline Form 1) of niraparib (1S)-(+)-camsylate is characterised by XRPD diffraction angles at 2θ values of 16.0°, 13.5°, 17.6°, 24.3°, 24.6°, 11.1°, 16.4°, 23.7°, 16.7°, 20.3°, 6.7°, 25.2°, 25.0°, 25.8°, 26.8°, 22.8°, 9.5°, 16.9°, 14.3° and 7.7°.

In any of the above-mentioned embodiments, the XRPD pattern of a crystalline form (crystalline Form 1) of niraparib (1S)-(+)-camsylate may contain one or more diffraction angles at 2θ values of 6.7°, 16.4°, 23.7° and/or 25.2°. In embodiments, the XRPD pattern of a crystalline form (crystalline Form 1) of niraparib (1S)-(+)-camsylate contains at least two diffraction angles at 2θ values of 6.7°, 16.4°, 23.7° and/or 25.2°. In other embodiments, the XRPD pattern of a crystalline form of niraparib (1S)-(+)-camsylate contains at least three diffraction angles at 2θ values of 6.7°, 16.4°, 23.7° and/or 25.2°.

In embodiments, the XRPD pattern of a crystalline form (crystalline Form 1) of niraparib (1S)-(+)-camsylate contains a diffraction angle at a 2θ value of 16.4°. In embodiments, the XRPD pattern of a crystalline form (crystalline Form 1) of niraparib (1S)-(+)-camsylate contains diffraction angles at 2θ values of 16.4° and 23.7°. In embodiments, the XRPD pattern of a crystalline form (crystalline Form 1) of niraparib (1S)-(+)-camsylate contains diffraction angles at 2θ values of 6.7°, 16.4° and 23.7°. In embodiments, the XRPD pattern of a crystalline form (crystalline Form 1) of niraparib (1S)-(+)-camsylate contains diffraction angles at 2θ values of 6.7°, 16.4°, 23.7° and 25.2°.

In embodiments, a crystalline form (crystalline Form 1) of niraparib (1S)-(+)-camsylate is characterised by XRPD diffraction angles having 2θ values (and, optionally, relative intensity values) as substantially recited in Table 4 of Example 4. In embodiments, the position of an XRPD diffraction angle is within ±0.2000° 2θ of the value specified in Table 4 and/or the d-spacing is within ±0.20000 Å or ±0.10000 Å of the value specified in Table 4. In embodiments, the height and/or the area of the diffraction angle is within ±10% or ±5% of the value specified in Table 4. In embodiments, the relative intensity is within ±10% or ±5% of the value specified in Table 4.

Figure 22:
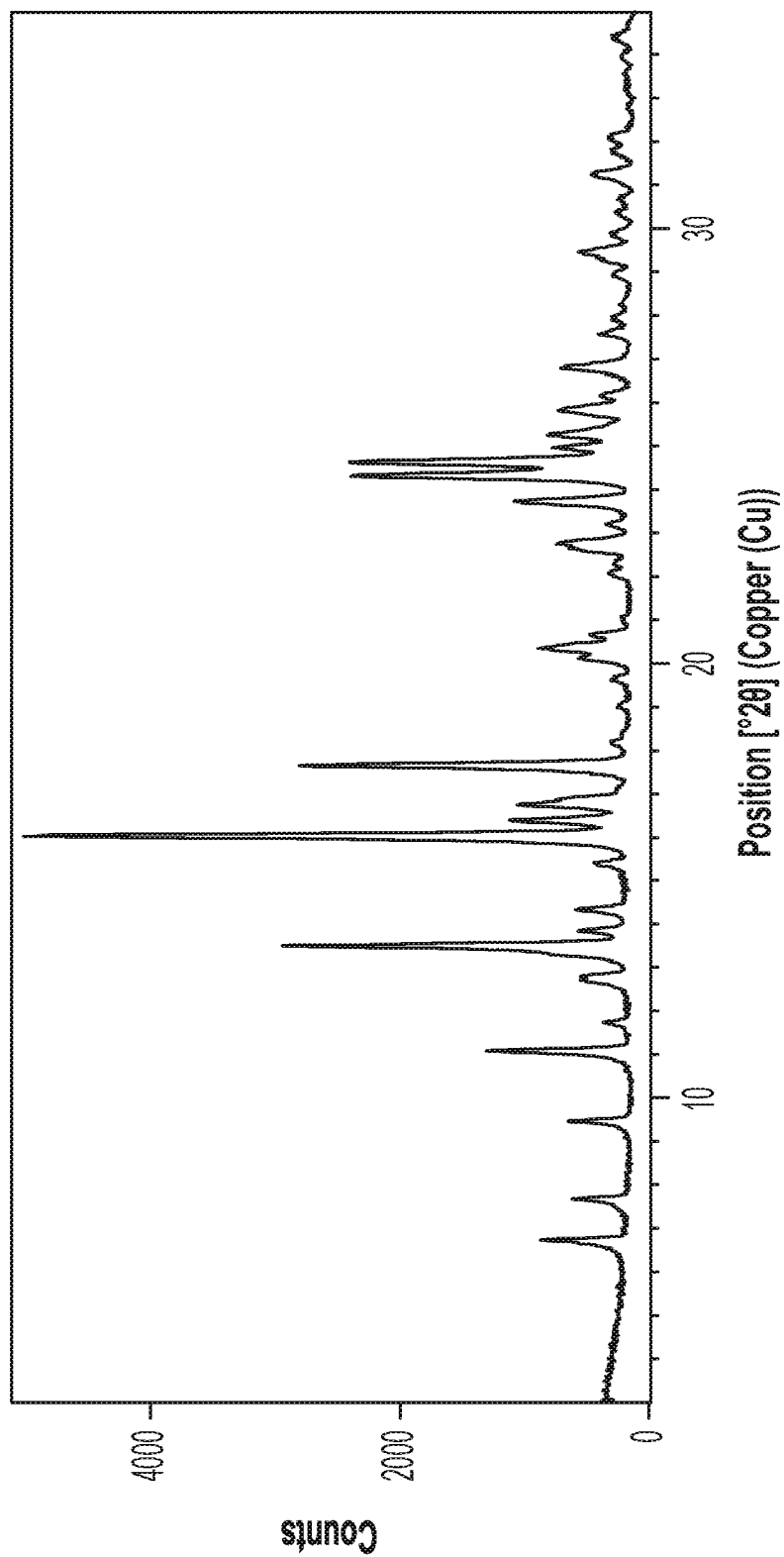
FIG. 22 shows an exemplary XRPD pattern for the crystalline Form 1 of the (1S)-(+)-camsylate salt of 2-{4-[(3S)-piperidin-3-yl]phenyl}-2H-indazole-7-carboxamide (niraparib).
Figure 23:
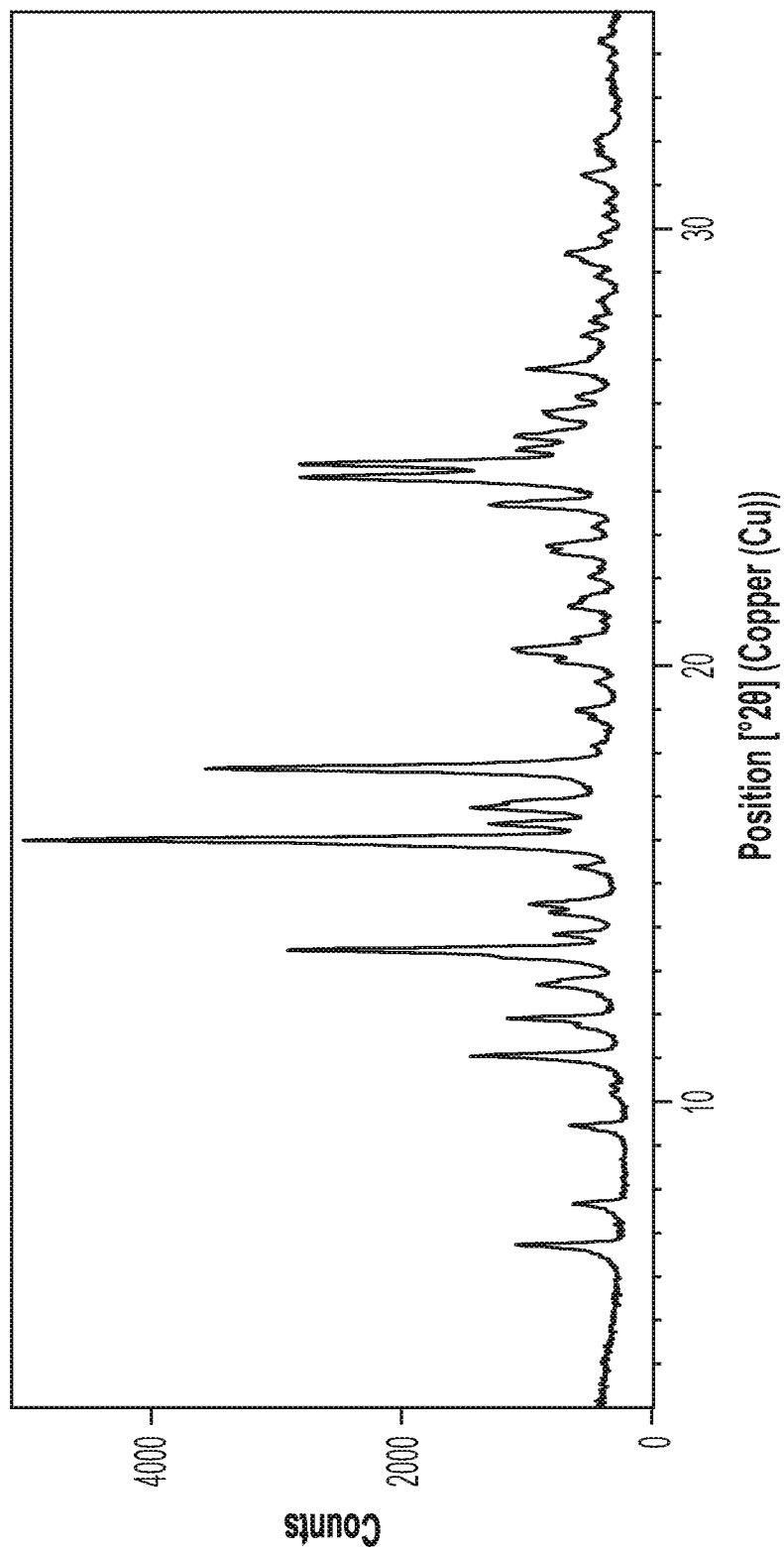
FIG. 23 shows an exemplary XRPD pattern for the crystalline Form 1 of the (1S)-(+)-camsylate salt of 2-{4-[(3S)-piperidin-3-yl]phenyl}-2H-indazole-7-carboxamide (niraparib) after storage at 40° C. and 75% relative humidity for 24h.

In embodiments, a crystalline form (crystalline Form 1) of niraparib (1S)-(+)-camsylate is characterised by the XRPD pattern shown (or substantially as shown) in FIG. 22.

In embodiments, a crystalline form (crystalline Form 1) of niraparib (1S)-(+)-camsylate is characterised by a melting point of about 235° C. to about 245° C. In embodiments, a crystalline form (crystalline Form 1) of niraparib (1S)-(+)-camsylate is characterised by a melting point of about 239° C.

In embodiments, a crystalline form (crystalline Form 1) of niraparib (1S)-(+)-camsylate is characterised by a DSC thermogram in which the onset of melting (endothermic peak) is about 235° C. and/or wherein the peak minimum is about 246° C. In embodiments, a crystalline form of niraparib (1S)-(+)-camsylate is characterised by having a DSC thermogram as shown (or substantially as shown) in FIG. 24.

In embodiments, a crystalline form (crystalline Form 1) of niraparib (1S)-(+)-camsylate is characterised by having an infra-red spectrum which includes a peak at about 3467 cm$^{-1}$, a peak at about 3306 cm$^{-1}$, a peak at about 1724 cm$^{-1}$, a peak at about 1660 cm$^{-1}$ and a peak at about 1611 cm$^{-1}$ e.g. when measured using a FT-IR method as described herein. In embodiments, a crystalline form (crystalline Form 1) of niraparib (1S)-(+)-camsylate is characterised by having an FT-IR spectrum as shown (or substantially as shown) in FIG. 21.

In embodiments, a crystalline form (crystalline Form 1) of niraparib (1S)-(+)-camsylate is characterised by being slightly hygroscopic. Hygroscopicity may be determined, for example, by GVS (e.g. as described in the following Examples). Thus, in embodiments, a crystalline form (crystalline Form 1) of niraparib (1S)-(+)-camsylate may be characterised by adsorbing less than 2% by weight of water up to 90% relative humidity (e.g. at 25° C.). In embodiments, a crystalline form (crystalline Form 1) of niraparib (1S)-(+)-camsylate is characterised by adsorbing about 1.3% by weight of water up to 90% relative humidity (e.g. at 25° C.). In embodiments, a crystalline form (crystalline Form 1) of niraparib (1S)-(+)-camsylate is characterised by the GVS thermogram as shown (or substantially as shown) in FIG. 25.

In embodiments, a crystalline form (crystalline Form 1) of niraparib (1S)-(+)-camsylate may be characterised by being stable under conditions of elevated temperature and/or humidity.

In embodiments, substantially all (e.g. at least 90%, at least 95%, at least 99% or about 100%) of a crystalline form (crystalline Form 1) of niraparib (1S)-(+)-camsylate retains the same form (e.g. when assessed by XRPD) when exposed to 90% relative humidity at room temperature (e.g. about 25° C.). In other embodiments, substantially all (e.g. at least 90%, at least 95%, at least 99% or about 100%) of a crystalline form (crystalline Form 1) of niraparib (1S)-(+)-camsylate retains the same form (e.g. when assessed by XRPD) when exposed to 90% relative humidity at elevated temperature (e.g. about 30° C., 40° C., 50° C., 60° C. or 75° C.).

A crystalline form (crystalline Form 1) of niraparib (1S)-(+)-camsylate may be further characterised by any combination of the characteristic stability, melting point, FT-IR spectrum, scanning differential calorimetry thermogram, gravimetric vapour sorption thermogram or XRPD diffraction angle values as described herein.

Solubility

The niraparib salts of the present invention have desirable properties for pharmaceutical formulation, including, in particular, desirable solubility properties. Viewed from this aspect, the invention provides 2-{4-[(3S)-piperidin-3-yl]phenyl}-2H-indazole-7-carboxamide (niraparib) camphorate, 2-{4-[(3S)-piperidin-3-yl]phenyl}-2H-indazole-7-carboxamide (niraparib) mandelate or 2-{4-[(3S)-piperidin-3-yl]phenyl}-2H-indazole-7-carboxamide (niraparib) camsylate (e.g. as described herein) having a solubility in an aqueous medium of at least 1 mg/mL.

By "aqueous medium" is meant a liquid medium which comprises water and, optionally, one or more ionic species to act as a buffer and/or pH modifying agent. Where another solvent, e.g. an organic solvent, is present in the medium, this preferably represents less than 50% by volume of the solution (e.g. less than 20%, less than 15%, less than 10%, less than 5% or less than 1% by volume of the solution). Exemplary aqueous media include water and the buffer solutions described in Example 10.

In embodiments, the 2-{4-[(3S)-piperidin-3-yl]phenyl}-2H-indazole-7-carboxamide (niraparib) salt has a solubility in an aqueous medium of at least 1 mg/mL, wherein the aqueous medium has a pH of between 1 and 7. In embodiments, the niraparib salt has a solubility in an aqueous medium of at least 1 mg/mL, wherein the aqueous medium has a pH of between 1 and 5, e.g. of between 1 and 3, of between 1 and 2, or of about 1. In other embodiments, the niraparib salt has a solubility in an aqueous medium of at least 1 mg/mL, wherein the aqueous medium has a pH of about 4.5 or of about 6.8. In embodiments, the aqueous medium has a pH of less than 7. In embodiments, the aqueous medium does not consist only of water.

In embodiments, the solubility of the niraparib salt is at least 1.2 mg/mL. In embodiments, the solubility of the niraparib salt is at least 1.5 mg/mL, e.g. at least 2.0, 2.5, 3.0, 3.5, 4.0, 4.5 or 5.0 mg/mL. In embodiments, the solubility of the niraparib salt is at least 7 mg/mL, e.g. at least 8, 9, 10, 11, 12, 13, 14, 15, 16, 17, 18, 19 or 20 mg/mL. In embodiments, the solubility of the niraparib salt is at least 25 mg/mL, e.g. at least 30, 35, 40, 45, 50, 60, 70, 80, 90 or 100 mg/mL. In embodiments, the solubility of the niraparib salt is at least 125 mg/mL, e.g. at least 150, 175 or 200 mg/mL.

In embodiments, the 2-{4-[(3S)-piperidin-3-yl]phenyl}-2H-indazole-7-carboxamide (niraparib) camphorate (e.g. as defined herein, such as the crystalline form 1 of niraparib (1R,3S)-(+)-camphorate) has a solubility of at least 1 mg/mL (e.g. about 1.2 mg/mL) in aqueous medium having a pH of about 6.8. In embodiments, the niraparib camphorate has a solubility of at least 10 mg/mL (e.g. at least 15 mg/mL, at least 20 mg/mL, or about 21 mg/mL) in aqueous medium having a pH of about 1.

In embodiments, the 2-{4-[(3S)-piperidin-3-yl]phenyl}-2H-indazole-7-carboxamide (niraparib) mandelate (e.g. as defined herein, such as the crystalline form 1 of niraparib (R)-(−)-mandelate) has a solubility of at least 5 mg/mL (e.g. about 7.8 mg/mL) in aqueous medium having a pH of about 6.8. In embodiments, the niraparib mandelate has a solubility of at least 10 mg/mL (e.g. at least 20 mg/mL, at least 30 mg/mL, at least 40 mg/mL, or about 45 mg/mL) in water. In embodiments, the niraparib mandelate has a solubility of at least 20 mg/mL (e.g. at least 30 mg/mL, at least 40 mg/mL, at least 50 mg/mL, or about 54 mg/mL) in aqueous medium having a pH of about 4.5. In embodiments, the niraparib mandelate has a solubility of at least 50 mg/mL (e.g. at least 75 mg/mL, at least 100 mg/mL, at least 125 mg/mL, at least 150 mg/mL or about 163 mg/mL) in aqueous medium having a pH of about 1.

In embodiments, the 2-{4-[(3S)-piperidin-3-yl]phenyl}-2H-indazole-7-carboxamide (niraparib) camsylate (e.g. as defined herein, such as the crystalline form 1 of niraparib (1S)-(+)-camsylate) has a solubility of at least 1 mg/mL (e.g. at least 1.5 mg/mL or about 1.7 mg/mL) in aqueous medium having a pH of about 6.8. In embodiments, the niraparib camsylate has a solubility of at least 2.5 mg/mL (e.g. at least 3.0 mg/mL, at least 4.0 mg/mL, at least 5.0 mg/mL, or about 5.9 mg/mL) in water. In embodiments, the niraparib camsylate has a solubility of at least 3.0 mg/mL (e.g. at least 4.0 mg/mL, at least 5.0 mg/mL, at least 6.0 mg/mL, or about 7.1 mg/mL) in aqueous medium having a pH of about 4.5. In embodiments, the niraparib camsylate has a solubility of at least 5.0 mg/mL (e.g. at least 7.5 mg/mL, at least 10.0 mg/mL, or about 11.5 mg/mL) in aqueous medium having a pH of about 1.

Methods for determining the solubility of a 2-{4-[(3S)-piperidin-3-yl]phenyl}-2H-indazole-7-carboxamide (niraparib) salt as defined herein would be apparent to the skilled person. In embodiments, the method for determining the solubility of a salt as defined herein is a method as set forth in Example 10.

Pharmaceutical Compositions

In another aspect, the invention provides a pharmaceutical composition comprising a camphorate, mandelate or camsylate salt of 2-{4-[(3S)-piperidin-3-yl]phenyl}-2H-indazole-7-carboxamide (niraparib) (e.g. a salt as described herein), and at least one pharmaceutically acceptable excipient.

In embodiments, the pharmaceutical composition comprises crystalline 2-{4-[(3S)-piperidin-3-yl]phenyl}-2H-indazole-7-carboxamide (niraparib) camphorate (e.g. crystalline 2-{4-[(3S)-piperidin-3-yl]phenyl}-2H-indazole-7-carboxamide (niraparib) (+)-camphorate or crystalline 2-{4-[(3S)-piperidin-3-yl]phenyl}-2H-indazole-7-carboxamide (niraparib) (−)-camphorate as described herein). In embodiments, the pharmaceutical composition comprises crystalline 2-{4-[(3S)-piperidin-3-yl]phenyl}-2H-indazole-7-carboxamide (niraparib) mandelate (e.g. crystalline 2-{4-[(3S)-piperidin-3-yl]phenyl}-2H-indazole-7-carboxamide (niraparib) (R)-(−)-mandelate as described herein). In embodiments, the pharmaceutical composition comprises crystalline 2-{4-[(3S)-piperidin-3-yl]phenyl}-2H-indazole-7-carboxamide (niraparib) camsylate (e.g. crystalline 2-{4-[(3S)-piperidin-3-yl]phenyl}-2H-indazole-7-carboxamide (niraparib) (1S)-(+)-camsylate as described herein).

In embodiments, the pharmaceutical composition comprises about 20-80 wt % of said niraparib salt, such as e.g. about 45-70 wt %, about 40-50 wt %, about 45-55 wt %, about 50-60 wt %, about 55-65 wt %, about 60-70 wt %, about 65-75 wt %, about 70-80 wt %, or about 40-60 wt % of said niraparib salt (where the wt % is based on the weight of niraparib freebase which is present in said salt as a percentage of the weight of the pharmaceutical composition).

The pharmaceutical composition comprises at least one pharmaceutically acceptable excipients. The pharmaceutically acceptable excipient can be any such excipient known in the art including those described in, for example, Remington's Pharmaceutical Sciences, Mack Publishing Co. (A. R. Gennaro edit. 1985). Pharmaceutical compositions of the compounds presently disclosed may be prepared by conventional means known in the art including, for example, mixing at least one presently disclosed compound with a pharmaceutically acceptable excipient.

Exemplary pharmaceutically acceptable excipients for the purposes of pharmaceutical compositions disclosed herein include, but are not limited to, binders, disintegrants, superdisintegrants, lubricants, diluents, fillers, flavors, glidants, sorbents, solubilizers, chelating agents, emulsifiers, thickening agents, dispersants, stabilizers, suspending agents, adsorbents, granulating agents, preservatives, buffers, coloring agents and sweeteners or combinations thereof. In embodiments, the pharmaceutically acceptable excipient comprises hydroxypropyl methylcellulose, e.g. low substituted hydroxypropyl cellulose. In embodiments, the pharmaceutically acceptable excipient comprises lactose, e.g. lactose monohydrate. In embodiments, the pharmaceutically acceptable excipient comprises magnesium stearate. In some embodiments, the pharmaceutically acceptable excipient is lactose monohydrate and magnesium stearate.

Various useful fillers or diluents include, but are not limited to, calcium carbonate (Barcroft™, MagGran™, Millicarb™, Pharma-Carb™, Precarb™, Sturcal™, Vivapres Ca™), calcium phosphate, dibasic anhydrous (Emcompress Anhydrous™, Fujicalin™), calcium phosphate, dibasic dihydrate (Calstar™, Di-Cafos™, Emcompress™), calcium phosphate tribasic (Tri-Cafos™, TRI-TAB™), calcium sulphate (Destab™, Drierite™, Snow White™, Cal-Tab™, Compactrol™, Sanacet™), cellulose powdered (Arbocel™, Elcema™, Sanacet™), silicified microcrystailine cellulose, cellulose acetate, compressible sugar (Di-Pac™), confectioner's sugar, dextrates (Candex™, Emdex™), dextrin (Avedex™, Caloreen™, Primogran W™), dextrose (Caridex™, Dextrofin™, Tab fine D-IOO™), fructose (Fructofin™, Krystar™), kaolin (Lion™, Sim 90™), lactitol (Finlac DC™, Finlac MCX™), lactose (Anhydrox™, CapsuLac™, Fast-Flo™, FlowLac™, GranuLac™, InhaLac™, Lactochem™, Lactohaie™, Lactopress™, Microfme™, Microtose™, Pharmatose™, Prisma Lac™, Respitose™, SacheLac™, SorboLac™, Super-Tab™, Tablettose™, Wyndale™, Zeparox™), lactose monohydrate, magnesium carbonate, magnesium oxide (MagGran MO™), maltodextrin (C*Dry MD™, Lycatab DSH™, Maldex™, Maitagran™, Maltrin™, Maltrin QD™, Paselli MD 10 PH™, Star-Dri™), maltose (Advantose 100™), mannitol (Mannogem™, Pearlitol™), microcrystalline cellulose (Avicel PH™, Celex™, Celphere™, Ceolus KG™, Emcocel™, Pharmacel™, Tabulose™, Vivapur™), polydextrose (Litesse™), simethicone (Dow Corning Q7-2243 LVA™, Cow Corning Q7-2587™, Sentry Simethicone™), sodium alginate (Keltone™, Protanal™), sodium chloride (Alberger™), sorbitol (Liponec 70-NC™, Liponic 76-NCv, Meritol™, Neosorb™, Sorbitol Instant™, Sorbogem™), starch (Flufiex W™, Instant Pure-Cote™, Melojei™, Meritena Paygel 55™, Perfectamyl D6PH™, Pure-Cote™, Pure-Dent™, Pure-Gel™, Pure-Set™, Purity 21™, Purity 826™, Tablet White™), pregelatinized starch, sucrose, trehalose and xylitol, or mixtures thereof. In embodiments, the filler comprises lactose monohydrate.

In embodiments, the composition comprises about 5-90% by weight of filler, e.g. the filler is present in an amount of about 10-80%, about 15-70%, about 20-60% or about 25-50% by weight. For example, the composition may comprise about 40%, 45%, 50%, 55%, 60%, 65%, 70%, 75% or 80% by weight of filler. In embodiments, the composition comprises from about 25 mg to about 1000 mg of filler, e.g. the filler is present in an amount of from about 50 mg to about 750 mg, from about 100 mg to about 600 mg, from about 150 mg to about 500 mg or from about 200 mg to about 450 mg. For example, the composition may comprise about 250, 275, 300, 325, 350, 375, 400, 425, 450, 475 or 500 mg of filler.

Various useful lubricants include, but are not limited to, calcium stearate (HyQual™), glycerine monostearate (Imwitor™ 191 and 900, Kessco GMS5™, 450 and 600, Myvaplex 600P™, Myvatex™, Rita GMS™, Stepan GMS™, Tegn™, Tegn™ 503 and 515, Tegin 4100™, Tegin M™, Unimate GMS™), glyceryl behenate (Compritol 888 ATO™), glyceryl palmitostearate (Precirol ATO 5™), hydrogenated castor oil (Castorwax MP 80™, Croduret™, Cutina HR™, Fancol™, Simulsol 1293™), hydrogenated vegetable oil 0 type I (Sterotex™, Dynasan P60™, Hydrocote™, Lipovol HS-K™, Sterotex HM™), magnesium lauryl sulphate, magnesium stearate, medium-chain triglycerides (Captex 300™, Labrafac CC™, Miglyol 810™, Neobee M5™, Nesatol™, Waglinol 3/9280™), poloxamer (Pluronic™, Synperonic™), polyethylene 5 glycol (Carbowax Sentry™, Lipo™, Lipoxol™, Lutrol E™, Pluriol E™), sodium benzoate (Antimol™), sodium chloride, sodium lauryl sulphate (Elfan 240™, Texapon Ki 2P™), sodium stearyl fumarate (Pruv™), stearic acid (Hystrene™, Industrene™, Kortacid 1895™, Pristerene™), talc (Altaic™, Luzenac™, Luzenac Pharma™, Magsil Osmanthus™, 0 Magsil Star™, Superiore™), sucrose stearate (Surfhope SE Pharma D-1803 F™) and zinc stearate (HyQual™) or mixtures thereof. Examples of suitable lubricants include, but are not limited to, magnesium stearate, calcium stearate, zinc stearate, stearic acid, talc, glyceryl behenate, polyethylene glycol, polyethylene oxide polymers, sodium lauryl sulfate, magnesium lauryl sulfate, sodium oleate, sodium stearyl fumarate, DL-leucine, colloidal silica. In embodiments, the lubricant comprises magnesium stearate.

In embodiments, the composition comprises about 0.1-5% by weight of lubricant, e.g. the lubricant is present in an amount of about 0.2-2%, about 0.3-1%, about 0.4-0.75% or about 0.5-0.7% by weight. For example, the composition may comprise about 0.3%, 0.4%, 0.5%, 0.6%, 0.7% or 0.8% by weight of lubricant. In embodiments, the composition comprises from about 0.01 mg to about 10 mg of lubricant, e.g. the lubricant is present in an amount of from about 0.01 mg to 0.05 mg, 0.05 mg to 0.1 mg, 0.1 mg to 0.2 mg, 0.2 mg to 0.25 mg, 0.25 mg to 0.5 mg, 0.5 mg to 0.75 mg, 0.7 mg to 0.95 mg, 0.9 mg to 1.15 mg, 1.1 mg to 1.35 mg, 1.3 mg to 1.5 mg, 1.5 mg to 1.75 mg, 1.75 to 1.95 mg, 1.9 mg to 2.15 mg, 2.1 mg to 2.35 mg, 2.3 mg to 2.55 mg, 2.5 mg to 2.75 mg, 2.7 mg to 3.0 mg, 2.9 mg to 3.15 mg, 3.1 mg to 3.35 mg, 3.3 mg to 3.5 mg, 3.5 mg to 3.75 mg, 3.7 mg to 4.0 mg, 4.0 mg to 4.5 mg, 4.5 mg to 5.0 mg, 5.0 mg to 5.5 mg, 5.5 mg to 6.0 mg, 6.0 mg to 6.5 mg, 6.5 mg to 7.0 mg, 7.0 mg to 7.5 mg, 7.5 mg to 8.0 mg, 8.0 mg to 8.5 mg, 8.5 mg to 9.0 mg, 9.0 mg to 9.5 mg, or 9.5 mg to 10.0 mg. For example, the composition may comprise about 0.01 mg, 0.05 mg, 0.1 mg, 0.2 mg, 0.25 mg, 0.5 mg, 0.7 mg, 0.9 mg, 1.1 mg, 1.3 mg, 1.5 mg, 1.7 mg, 1.9 mg, 2. mg, 2.3 mg, 2.5 mg, 2.75 mg, 3.0 mg, 3.1 mg, 3.3 mg, 3.5 mg, 3.7 mg, 4.0 mg, 4.5 mg, 5.0 mg, 5.5 mg, 6.0 mg, 6.5 mg, 7.0 mg, 7.5 mg, 8.0 mg, 8.5 mg, 9.0 mg, 9.5 mg or 10.0 mg by weight of lubricant.

Various useful disintegrants include, but are not limited to, alginic acid (Protacid™, Satialgine H8™), calcium phosphate, tribasic (TRI-TAB™) carboxymethylcellulose calcium (ECG 505™), carboxymethylcellulose sodium (Akucell™, Finnfix™, Nymcel Tylose CB™), colloidal silicon dioxide (Aerosil™ Cab-O-Sil™, Wacker HDK™), croscarmellose sodium (Ac-Di-Sol™, Pharmacel XL™, Primellose™, Solutab™, Vivasol™), crospovidone (Collison CL™, Collison CL-M™, Polyplasdone XL™), docusate sodium, guar gum (Meyprodor™, Meyprofm™, Meyproguar™), low substituted hydroxypropyl cellulose, magnesium aluminum silicate (Magnabite™, Neusilin™, Pharmsorb™, Veegum™), methylcellulose (Methocel™, Metolose™), microcrystalline cellulose (Avicel PH™, Ceoius KG™, Emcoel™, Ethispheres™, Fibrocel™, Pharmacel™, Vivapur™), povidone (Collison™, Plasdone™) sodium alginate (Kelcosol™, Ketone™, Protanal™), sodium starch glycolate, polacrilin potassium (Amberlite IRP88™), silicified microcrystalline cellulose (ProSotv™), starch (Aytex P™, Fluftex W™, Melojel™, Meritena™, Paygel 55™, Perfectamyl D6PH™, Pure-Bind™, Pure-Cote™, Pure-Dent™, Purity 21™, Purity 826™, Tablet White™) or pre-gelatinized starch (Lycatab PGS™, Merigel™, National 78-1551™, Pharma-Gel™, Prejel™, Sepistab ST 200™, Spress B820™ Starch 1500 G™, Tablitz™, Unipure LD™), or mixtures thereof. In embodiments, the composition comprises about 0 to about 10% by weight of disintegrant.

Various useful glidants include, but are not limited to, tribasic calcium phosphate (TRI-TAB™), calcium silicate, cellulose, powdered (Sanacel™, Solka-Floe™), colloidal silicon dioxide (Aerosil™, Cab-O-Sil M-5P™, Wacker HDK™), magnesium silicate, magnesium trisilicate, starch (Melojel™, Meritena™, Paygel 55™, Perfectamyl D6PH™, Pure-Bind™, Pure-Cote™, Pure-Dent™, Pure-Gel™, Pure-Set™, Purity 21™, Purity 826™, Tablet White™) and talc (Luzenac Pharma™, Magsil Osmanthus™, Magsil Star™ Superiore™), or mixtures thereof. In embodiments, the composition comprises about 0 to about 15% by weight of glidant.

Pharmaceutically acceptable surfactants include, but are limited to, both non-ionic and ionic surfactants suitable for use in pharmaceutical dosage forms. Ionic surfactants may include one or more of anionic, cationic or zwitterionic surfactants. Various useful surfactants include, but are not limited to, sodium lauryl sulfate, monooleate, monolaurate, monopalmitate, monostearate or another ester of olyoxyethylene sorbitane, sodium dioctylsulfosuccinate, lecithin, stearyic alcohol, cetostearylic alcohol, cholesterol, polyoxyethylene ricin oil, polyoxyethylene fatty acid glycerides, poloxamer, or any other commercially available co-processed surfactant like SEPITRAP® 80 or SEPITRAP® 4000 and mixtures thereof. In embodiments, the composition comprises about 0 to about 5% by weight of surfactant.

In embodiments, a solid pharmaceutical composition of the disclosure comprises a camphorate, mandelate or camsylate salt of niraparib (e.g. a salt as described herein), a diluent and a lubricant. In embodiments, the solid pharmaceutical composition comprises a camphorate, mandelate or camsylate salt of niraparib (e.g. a crystalline salt as described herein), lactose monohydrate and magnesium stearate.

In embodiments, a solid pharmaceutical composition of the disclosure comprises (by weight of the composition) about 20-60% of the 2-{4-[(3S)-piperidin-3-yl]phenyl}-2H-indazole-7-carboxamide (niraparib) salt, about 20-80% diluent and about 0.1-5% lubricant. In embodiments, the pharmaceutical composition comprises (by weight of the composition) about 40-60% of the niraparib salt, about 40-70% diluent (e.g. lactose monohydrate) and about 0.2-2% lubricant (e.g. magnesium stearate).

The pharmaceutical compositions can be formulated so as to provide slow, extended, or controlled release of the active ingredient therein using, for example, hydroxypropylmethyl cellulose in varying proportions to provide the desired release profile, other polymer matrices, liposomes and/or microspheres. The pharmaceutical compositions can also optionally contain opacifying agents and may be of a composition that releases the active ingredient(s) only, or preferentially, in a certain portion of the gastrointestinal tract, optionally, in a delayed manner, e.g. by using an enteric coating. Examples of embedding compositions include polymeric substances and waxes. The active ingredient can also be in micro-encapsulated form, if appropriate, with one or more pharmaceutically acceptable carriers, excipients, or diluents well known in the art (see, e.g. Remington's). The compounds presently disclosed may be formulated for sustained delivery according to methods well known to those of ordinary skill in the art. Examples of such formulations can be found in U.S. Pat. Nos. 3,119,742; 3,492,397; 3,538,214; 4,060,598; and 4,173,626.

Synthesis

The 2-{4-[(3S)-piperidin-3-yl]phenyl}-2H-indazole-7-carboxamide (niraparib) salts of the present disclosure may be prepared, for example, from niraparib freebase, e.g. by slurrying niraparib freebase in the presence of the appropriate acid.

The niraparib salts of the present disclosure may be prepared in crystalline form. Various techniques may be used to obtain the salts in crystalline forms. These techniques include preparation from a solvent system, e.g. by solvent evaporation, cooling, and/or the addition of one or more anti-solvents (e.g. TBME). These techniques may also include heating the salt, e.g. close to or past its melting point, and then cooling. Crystallization in solution may be performed either with or without seeding. Exemplary solvents for use in preparing the crystalline salts of niraparib which are disclosed herein include acetone, acetonitrile, ethanol, ethyl acetate, methanol, THF, and mixtures thereof. In some instances, crystalline salts of the present disclosure may be obtained by recrystallization from an organic solvent, such as methanol.

Methods for the preparation of the niraparib salts of the present disclosure, including crystalline salts, are illustrated in the following Examples.

Alternative methods for the preparation of the niraparib salts of the present disclosure, and crystalline forms thereof, would be apparent to the skilled person on the basis of their common general knowledge and the teaching of the present application. For example, the skilled person would appreciate that amorphous forms of the niraparib salts of the present disclosure may be obtained by e.g. spray drying a solution of the appropriate salt.

Medical Indications

The 2-{4-[(3S)-piperidin-3-yl]phenyl}-2H-indazole-7-carboxamide (niraparib) salts and pharmaceutical compositions described herein are useful in therapy, in particular in the therapeutic treatment of PARP-1 and PARP-2 mediated conditions in a subject. Methods for treating PARP-1 and PARP-2 mediated conditions are described in WO 2018/005818.

In certain embodiments, a niraparib salt described herein may provide improved therapeutic benefits as compared to administration of a different form of niraparib (e.g. a crystalline niraparib tosylate monohydrate). In embodiments, an improved therapeutic benefit may be a change (e.g. reduction) in the incidence and/or severity of an unwanted side-effect observed with a different form of niraparib. In embodiments, an unwanted side effect is thrombocytopenia, anemia, neutropenia, leukopenia, palpitations, nausea, constipation, vomiting, abdominal pain/distention, mucositis/stomatitis, diarrhea, dyspepsia, dry mouth, fatigue/asthenia, decreased appetite, urinary tract infection, AST/ALT elevation, myalgia, back pain, arthralgia, headache, dizziness, dysgeusia, insomnia, anxiety, nasopharyngitis, dyspnea, cough, rash, or hypertension. In embodiments, an unwanted side-effect is a hematological side-effect (e.g. thrombocytopenia, anemia, neutropenia, or leukopenia). In embodiments, an unwanted side-effect is a non-hematological side effect. In embodiments, an unwanted side-effect is a cardiovascular effect (e.g. palpitations). In embodiments, an unwanted side-effect is a gastrointestinal disorder (e.g. nausea, constipation, vomiting, abdominal pain/distention, mucositis/stomatitis, diarrhea, dyspepsia, or dry mouth). In embodiments, an unwanted side-effect is fatigue or asthenia. In embodiments, an unwanted side-effect is a metabolism or nutrition disorder (e.g. decreased appetite). In embodiments, an unwanted side-effect is an infection or infestation (e.g. urinary tract infection). In embodiments, an unwanted side-effect is elevation in AST/ALT. In embodiments, an unwanted side-effect is a musculoskeletal or connective tissue disorder (e.g. myalgia, back pain, or arthralgia). In embodiments, an unwanted side-effect is a nervous system disorder (headache, dizziness, or dysgeusia). In embodiments, an unwanted side-effect is a psychiatric disorder (e.g. insomnia or anxiety). In embodiments, an unwanted side-effect is a respiratory, thoracic, or mediastinal disorder (e.g. nasopharyngitis, dyspnea, or cough). In embodiments, an unwanted side-effect is a skin or subcutaneous tissue disorder (e.g. rash). In embodiments, an unwanted side-effect is a vascular disorder (e.g. hypertension).

In embodiments, an unwanted side-effect is myelodysplastic syndrome/acute myeloid leukemia. In embodiments, an unwanted side-effect is bone marrow suppression.

Subjects to be treated according to the methods described herein include vertebrates, such as mammals. In preferred embodiments the mammal is a human patient.

In one aspect, the present disclosure provides a camphorate, mandelate or camsylate salt of niraparib (e.g. a salt as described herein), for use in therapy. Also provided is the use of a camphorate, mandelate or camsylate salt of niraparib (e.g. a salt as described herein), in the manufacture of a medicament.

In another aspect, the present disclosure provides a method of treating cancer, stroke, autoimmune diabetes, a neurological disease, an inflammatory disease, a metabolic disease or a cardiovascular disease in a subject, the method comprising administering to the subject an effective amount of a camphorate, mandelate or camsylate salt of niraparib (e.g. a salt as described herein). Also provided is a camphorate, mandelate or camsylate salt of niraparib (e.g. a salt as described herein), for use in a method of treating cancer, stroke, autoimmune diabetes, a neurological disease, an inflammatory disease, a metabolic disease or a cardiovascular disease. Further provided is the use of a camphorate, mandelate or camsylate salt of niraparib (e.g. a salt as described herein), in the manufacture of a medicament for use in a method of treating cancer, stroke, autoimmune diabetes, a neurological disease, an inflammatory disease, a metabolic disease or a cardiovascular disease.

In a further aspect, the disclosure provides a method of treating a PARP-1 and/or PARP-2 mediated condition in a subject, the method administering to the subject an effective amount of a camphorate, mandelate or camsylate salt of niraparib (e.g. a salt as described herein). Also provided is a camphorate, mandelate or camsylate salt of niraparib (e.g. a salt as described herein), for use in a method of treating a PARP-1 and/or PARP-2 mediated condition. Further provided is the use of a camphorate, mandelate or camsylate salt of niraparib (e.g. a salt as described herein), in the manufacture of a medicament for use in a method of treating a PARP-1 and/or PARP-2 mediated condition.

Oncological Conditions (Cancers)

PARP inhibitors have shown activity as a monotherapy against tumors with existing DNA repair defects, such as BRCA1 and BRCA2, and as a combination therapy when administered together with anti-cancer agents that induce DNA damage. Despite several advances in treatment of ovarian cancer, most patients eventually relapse, and subsequent responses to additional treatment are often limited in duration. Women with germline BRCA1 or BRCA2 mutations have an increased risk for developing high grade serous ovarian cancer (HGSOC), and their tumors appear to be particularly sensitive to treatment with a PARP inhibitor. In addition, published scientific literature indicates that patients with platinum sensitive HGSOC who do not have germline BRCA1 or BRCA2 mutations may also experience clinical benefit from treatment with a PARP inhibitor. Since PARP inhibitors block DNA repair, in the context of cancer cells with the BRCA mutation, PARP inhibition results in synthetic lethality. For this reason, patients with germline mutations in a BRCA gene show marked clinical benefit following treatment with a PARP inhibitor.

In one embodiment, the condition to be treated is a cancer, especially a cancer which is associated with DNA repair defects, such as BRCA1 and/or BRCA2 mutations.

In embodiments, the cancer is a recurrent cancer.

In embodiments, a cancer is breast cancer, ovarian cancer, cervical cancer, epithelial ovarian cancer, fallopian tube cancer, primary peritoneal cancer, endometrial cancer, prostate cancer, testicular cancer, pancreatic cancer, esophageal cancer, head and neck cancer, gastric cancer, bladder cancer, lung cancer (e.g. adenocarcinoma, NSCLC and SCLC), bone cancer (e.g. osteosarcoma), colon cancer, rectal cancer, thyroid cancer, brain and central nervous system cancers, glioblastoma, neuroblastoma, neuroendocrine cancer, rhabdoid cancer, keratoacanthoma, epidermoid carcinoma, seminoma, melanoma, sarcoma (e.g. liposarcoma), bladder cancer, liver cancer (e.g. hepatocellular carcinoma), kidney cancer (e.g. renal cell carcinoma), myeloid disorders (e.g. AML, CML, myelodysplastic syndrome and promyelocytic leukemia), and lymphoid disorders (e.g. leukemia, multiple myeloma, mantle cell lymphoma, ALL, CLL, B-cell lymphoma, T-cell lymphoma, Hodgkin's lymphoma, non-Hodgkin's lymphoma, hairy cell lymphoma) may be treated with compounds and methods described herein.

The cancer may be selected from head and neck cancer, breast cancer (e.g. metastatic breast cancer), prostate cancer (e.g. metastatic prostate cancer), testicular cancer, ovarian cancer, endometrial cancer, colon cancer, rectal cancer, lung cancer (e.g. non-small cell lung cancer), bladder cancer, pancreatic cancer (e.g. metastatic pancreatic cancer), brain and central nervous system cancers (e.g. primary malignant brain tumour), neuroendocrine cancer, rhabdoid cancer, gynaecological cancer, peritoneal cancer, skin cancer, thyroid cancer, oesophageal cancer, cervical cancer, gastric cancer, liver cancer, stomach cancer, renal cell cancer, biliary tract cancer, hematologic cancer, bone cancer, and blood cancer.

In embodiments, the cancer is selected from colorectal carcinoma, large intestinal colon carcinoma, head and neck carcinoma, seminoma, sarcoma, lung carcinoma, lung adenocarcinoma, bladder carcinoma, Barret's adenocarcinoma, renal carcinoma, epidermoid carcinoma, and hepatocarcinoma. In embodiments, the cancer is selected from glioblastoma, astrocytoma, melanoma (e.g. metastatic melanoma), mesothelioma, myeloma, keratoacanthoma, neuroblastoma, histiocytic lymphoma, and lymphocytic leukaemia. In embodiments, the cancer is a solid tumour (e.g. a malignant solid tumour) which may be an advanced-stage solid tumour.

In embodiments, the cancer is a gynaecological cancer, e.g. selected from ovarian cancer, cancer of the fallopian tube(s), peritoneal cancer and breast cancer. In some embodiments, the gynaecological cancer is associated with HRD and/or BRCA1/2 mutation(s). In some embodiments, the gynaecological cancer is platinum sensitive. In other embodiments, the gynaecological cancer is not platinum sensitive. In embodiments, the gynaecological cancer previously responded (e.g. partially or fully) to platinum-based therapy but has since developed resistance to platinum-based therapy.

In embodiments, the cancer is ovarian cancer (e.g. epithelial ovarian cancer), cancer of the fallopian tube(s), or peritoneal cancer (e.g. primary peritoneal cancer). In other embodiments, the cancer is breast cancer.

In some embodiments, the methods of the invention treat subjects with ovarian cancer. In some embodiments, the methods of the invention treat subjects with epithelial ovarian cancer. In some embodiments, the methods of the invention treat subjects with fallopian tube cancer. In some embodiments, the methods of the invention treat subjects with primary peritoneal cancer. In some embodiments, the methods of the invention treat subjects with recurrent ovarian cancer. In some embodiments, the methods of the invention treat subjects with recurrent epithelial ovarian cancer. In some embodiments, the methods of the invention treat subjects with recurrent fallopian tube cancer. In some embodiments, the methods of the invention treat subjects with recurrent primary peritoneal cancer.

In some embodiments, the methods of the invention treat subjects with recurrent ovarian cancer following a complete or partial response to a chemotherapy, such as a platinum-based chemotherapy. In some embodiments, the methods of the invention treat subjects with recurrent epithelial ovarian cancer following a complete or partial response to a chemotherapy, such as a platinum-based chemotherapy. In some embodiments, the methods of the invention treat subjects with recurrent fallopian tube cancer following a complete or partial response to a chemotherapy, such as a platinum-based chemotherapy. In some embodiments, the methods of the invention treat subjects with recurrent primary peritoneal cancer following a complete or partial response to a chemotherapy, such as a platinum-based chemotherapy.

In some embodiments, the methods of the invention treat subjects with recurrent ovarian cancer, recurrent epithelial ovarian cancer, recurrent fallopian tube cancer and/or recurrent primary peritoneal cancer following a complete or partial response to a platinum-based chemotherapy, wherein the subjects begin the treatment no later than 8 weeks after their most recent platinum-containing regimen. For example, subjects can begin treatment with niraparib about 7 weeks after their most recent platinum-containing regimen. For example, subjects can begin treatment with niraparib about 6 weeks after their most recent platinum-containing regimen. For example, subjects can begin treatment with niraparib about 6 weeks after their most recent platinum-containing regimen. For example, subjects can begin treatment with niraparib about 5 weeks after their most recent platinum-containing regimen. For example, subjects can begin treatment with niraparib about 4 weeks after their most recent platinum-containing regimen. For example, subjects can begin treatment with niraparib about 3 weeks after their most recent platinum-containing regimen. For example, subjects can begin treatment with niraparib about 2 weeks after their most recent platinum-containing regimen. For example, subjects can begin treatment with niraparib about 1 week after their most recent platinum-containing regimen.

In embodiments, the method treats cancer in a subject exhibiting a positive HRD status. In some embodiments, the subject is further characterized by the absence of a mutation in BRCA1 and/or BRCA2. A positive HRD status may be determined by quantifying in a patient sample a number of Indicator Chromosomal Aberration regions. In some embodiments, a tumor sample from the subject has a positive HRD status.

In other embodiments, the method treats cancer in a subject exhibiting an absence of HRD, e.g. a subject having platinum-sensitive recurrent ovarian cancer. The absence of HRD may be characterized by a lack of chromosomal aberrations (a detectable variation in chromosomal DNA which may fall into at least one of three overlapping categories: loss of heterozygosity, allelic imbalance (e.g. telomeric allelic imbalance), or large scale transition).

In embodiments, a method described herein treats a cancer that is associated with deficiency in at least one gene involved in a DNA repair pathway. Various pathways exist for DNA repair, including base excision repair (BER), direct repair (DR), double stranded break (DSB) repair, homologous recombination repair (HRR), mismatch repair (MMR), nucleotide excision repair (NER), and non-homologous end joining (NHEJ) repair; disruptions in these pathways can lead to the development and/or growth of cancer. See, e.g. Kelley et al., *Future Oncol.*, 10(7):1215-1237, 2014.

Exemplary genes involved in DNA repair pathways are described in Table A.

TABLE A

DNA Repair Genes

| Gene Title | Gene Symbol |
| --- | --- |
| replication factor C (activator 1) 2, 40 kDa | RFC2 |
| X-ray repair complementing defective repair in Chinese hamster cells 6 (Ku autoantigen, 70 kDa) | XRCC6 |
| polymerase (DNA directed), delta 2, regulatory subunit 50 kDa | POLD2 |
| proliferating cell nuclear antigen | PCNA |
| replication protein A1, 70 kDa | RPA1 |
| replication protein A2, 32 kDa | RPA2 |
| excision repair cross-complementing rodent repair deficiency, complementation group 3 (xeroderma pigmentosum group B complementing) | ERCC3 |
| uracil-DNA glycosylase | UNG |
| excision repair cross-complementing rodent repair deficiency, complementation group 5 (xeroderma pigmentosum, complementation group G (Cockayne syndrome)) | ERCC5 |
| mutL homolog 1, colon cancer, nonpolyposis type 2 (*E. coli*) | MLH1 |
| ligase I, DNA, ATP-dependent | LIG1 |
| mutS homolog 6 (*E. coli*) | MSH6 |
| polymerase (DNA-directed), delta 4 | POLD4 |
| replication factor C (activator 1) 5, 36.5 kDa | RFC5 |
| damage-specific DNA binding protein 2, 48 kDa /// LIM homeobox 3 | DDB2 /// LHX3 |
| polymerase (DNA directed), delta 1, catalytic subunit 125 kDa | POLD1 |
| Fanconi anemia, complementation group G | FANCG |
| polymerase (DNA directed), beta | POLB |
| X-ray repair complementing defective repair in Chinese hamster cells 1 | XRCC1 |
| N-methylpurine-DNA glycosylase | MPG |
| excision repair cross-complementing rodent repair deficiency, complementation group 1 (includes overlapping antisense sequence) | ERCC1 |
| thymine-DNA glycosylase | TDG |
| Fanconi anemia, complementation group A /// Fanconi anemia, complementation group A | FANCA |
| replication factor C (activator 1) 4, 37 kDa | RFC4 |
| replication factor C (activator 1) 3, 38 kDa | RFC3 |
| APEX nuclease (apurinic/apyrimidinic endonuclease) 2 | APEX2 |
| RAD1 homolog (*S. pombe*) | RAD1 |
| breast cancer 1, early onset | BRCA1 |
| exonuclease 1 | EXO1 |
| flap structure-specific endonuclease 1 | FEN1 |
| mutL homolog 3 (*E. coli*) | MLH3 |
| O-6-methylguanine-DNA methyltransferase | MGMT |
| RAD51 homolog (RecA homolog, *E. coli*) (*S. cerevisiae*) | RAD51 |
| X-ray repair complementing defective repair in Chinese hamster cells 4 | XRCC4 |
| RecQ protein-like (DNA helicase Q1-like) | RECQL |
| excision repair cross-complementing rodent repair deficiency, complementation group 8 | ERCC8 |
| Fanconi anemia, complementation group C | FANCC |
| 8-oxoguanine DNA glycosylase | OGG1 |
| MRE11 meiotic recombination 11 homolog A (*S. cerevisiae*) | MRE11A |
| RAD52 homolog (*S. cerevisiae*) | RAD52 |
| Werner syndrome | WRN |
| xeroderma pigmentosum, complementation group A | XPA |
| Bloom syndrome | BLM |
| mutS homolog 3 (*E. coli*) | MSH3 |
| polymerase (DNA directed), epsilon 2 (p59 subunit) | POLE2 |
| RAD51 homolog C (*S. cerevisiae*) | RAD51C |
| ligase IV, DNA, ATP-dependent | LIG4 |
| excision repair cross-complementing rodent repair deficiency, complementation group 6 | ERCC6 |
| ligase III, DNA, ATP-dependent | LIG3 |
| RAD17 homolog (*S. pombe*) | RAD17 |
| X-ray repair complementing defective repair in Chinese hamster cells 2 | XRCC2 |
| mutY homolog (*E. coli*) | MUTYH |
| replication factor C (activator 1) 1, 145 kDa /// replication factor C (activator 1) 1, 145 kDa | RFC1 |
| breast cancer 2, early onset | BRCA2 |
| RAD50 homolog (*S. cerevisiae*) | RAD50 |

TABLE A-continued

DNA Repair Genes

| Gene Title | Gene Symbol |
| --- | --- |
| damage-specific DNA binding protein 1, 127 kDa | DDB1 |
| X-ray repair complementing defective repair in Chinese hamster cells 5 (double-strand-break rejoining; Ku autoantigen, 80 kDa) | XRCC5 |
| poly (ADP-ribose) polymerase family, member 1 | PARP1 |
| polymerase (DNA directed), epsilon 3 (p17 subunit) | POLE3 |
| xeroderma pigmentosum, complementation group C | XPC |
| mutS homolog 2, colon cancer, nonpolyposis type 1 (*E. coli*) | MSH2 |
| replication protein A3, 14 kDa | RPA3 |
| methyl-CpG binding domain protein 4 | MBD4 |
| nth endonuclease III-like 1 (*E. coli*) | NTHL1 |
| PMS2 postmeiotic segregation increased 2 (*S. cerevisiae*) /// PMS2-C terminal-like | PMS2 /// PMS2CL |
| uracil-DNA glycosylase 2 | UNG2 |
| APEX nuclease (multifunctional DNA repair enzyme) 1 | APEX1 |
| excision repair cross-complementing rodent repair deficiency, complementation group 4 | ERCC4 |
| RecQ protein-like 5 | RECQL5 |
| mutS homolog 5 (*E. coli*) | MSH5 |
| polymerase (DNA-directed), delta 3, accessory subunit | POLD3 |
| excision repair cross-complementing rodent repair deficiency, complementation group 2 (xeroderma pigmentosum D) | ERCC2 |
| RecQ protein-like 4 | RECQL4 |
| PMS1 postmeiotic segregation increased 1 (*S. cerevisiae*) | PMS1 |
| zinc finger protein 276 homolog (mouse) | ZFP276 |
| polymerase (DNA directed), epsilon | POLE |
| X-ray repair complementing defective repair in Chinese hamster cells 3 | XRCC3 |
| Nibrin | NBN |
| single-strand selective monofunctional uracil DNA glycosylase | SMUG1 |
| Fanconi anemia, complementation group F | FANCF |
| nei endonuclease VIII-like 1 (*E. coli*) | NEIL1 |
| Fanconi anemia, complementation group E | FANCE |
| Ataxia Telangiectasia Mutated | ATM |
| ATM and RAD3-related | ATR |
| BRCA1 associated protein-1 (ubiquitin carboxy-terminal hydrolase) gene | BAP1 |
| BRCA1 Associated RING Domain 1 (RING-Type E3 Ubiquitin Transferase) gene | BARD1 |
| BRCA1 Interacting Protein C-Terminal Helicase 1 gene | BRIP1 |
| Partner and localizer of BRCA2 gene | PALB2 |
| RAD51 Paralog B | RAD51B |
| RAD51 Paralog D | RAD51D |
| RAD54 Like | RAD54L |

In embodiments, method treats cancer in a subject exhibiting an absence of a germline mutation in BRCA1 and BRCA2. In some embodiments, the method treats cancer in a subject with a platinum-sensitive tumor exhibiting an absence of a germline mutation in BRCA1 and BRCA2.

In one aspect, the invention features a method of treating cancer comprising: identifying a cancer patient having deficiency in at least one gene listed in Table A.

In embodiments, a method described herein treats a cancer that is associated with deficiency in at least one gene involved in the homologous recombination repair (HRR) pathway. In embodiments, a deficiency is a non-BRCA deficiency. In embodiments, a deficiency is in two or more, three or more, four or more, five or more, six or more, seven or more, eight or more, nine or more, ten or more, eleven or more, twelve or more, thirteen or more, fourteen or more, fifteen or more, sixteen or more, seventeen or more, eighteen or more, nineteen or more, twenty or more, twenty-one or more, twenty-two or more, twenty-three or more, twenty-four or more, twenty-five or more, twenty-six or more, twenty-seven or more, twenty-eight or more, twenty-nine or more, or thirty or more genes selected from the group consisting of RFC2, XRCC6, POLD2, PCNA, RPA1, RPA2, ERCC3, UNG, ERCC5, MLH1, LIG1, MSH6, POLD4, RFC5, DDB2///LHX3, POLD1, FANCG, POLB, XRCC1, MPG, ERCC1, TDG, FANCA, RFC4, RFC3, APEX2, RAD1, EXO1, FEN1, MLH3, MGMT, RAD51, XRCC4, RECQL, ERCC8, FANCC, OGG1, MRE11A, RAD52, WRN, XPA, BLM, MSH3, POLE2, RAD51C, LIG4, ERCC6, LIG3, RAD17, XRCC2, MUTYH, RFC1, RAD50, DDB1, XRCC5, PARP1, POLE3, XPC, MSH2, RPA3, MBD4, NTHL1, PMS2///PMS2CL, UNG2, APEX1, ERCC4, RECQL5, MSH5, POLD3, ERCC2, RECQL4, PMS1, ZFP276, POLE, XRCC3, NBN, SMUG1, FANCF, NEIL1, FANCE, ATM, ATR, BAP1, BARD1, BRIP1, PALB2, RAD51B, RAD51D, and RAD54L.

In embodiments, cancer patients having HRR deficiencies due to at least one of the sixteen genes listed in Table B can benefit from methods described herein.

TABLE B

Non-BRCA1/2 HRR Pathway Genes
HRR Pathway Genes

ATM
ATR
BAP1
BARD1
BLM
BRIP1

TABLE B-continued

Non-BRCA1/2 HRR Pathway Genes
HRR Pathway Genes

MRE11A
NBN
PALB2
RAD51
RAD51B
RAD51C
RAD51D
RAD52
RAD54L
XRCC2

In embodiments, a deficiency in a gene involved in the HRR pathway is identified using a pre-specified gene panel. In embodiments, a pre-specified gene panel includes a gene listed in Table A or Table B, or any combinations thereof. In embodiments, a pre-specified gene panel comprises: at least one of ATM, ATR, BAP1, BARD1, BLM, BRIP1, MRE11A, NBN, PALB2, RAD51, RAD51B, RAD51C, RAD51D, RAD52, RAD54L, and XRCC2, and any combinations thereof, and at least one of BRCA1 and BRCA2. In embodiments, a pre-specified gene panel comprises: each of ATM, ATR, BAP1, BARD1, BLM, BRIP1, MRE11A, NBN, PALB2, RAD51, RAD51B, RAD51C, RAD51D, RAD52, RAD54L, and XRCC2; and at least one of BRCA1 and BRCA2. In embodiments, a pre-specified gene panel comprises ATM, ATR, BAP1, BARD1, BLM, BRIP1, MRE11A, NBN, PALB2, RAD51, RAD51B, RAD51C, RAD51D, RAD52, RAD54L, XRCC2, BRCA1, and BRCA2.

In embodiments, the method is a mono-therapy treatment. In other embodiments, the method is a combination therapy treatment.

In embodiments, the method is a combination therapy treatment in which the administration of a camphorate, mandelate or camsylate salt of niraparib (e.g. a salt as described herein) is combined with a second therapy which induces DNA damage. In embodiments, the second therapy comprises radiosensitization (the administration of ionizing radiation) and/or chemosensitization (the administration of one or more DNA damaging agents). The DNA damaging agents may, for example, be selected from DNA methylating agents (such as e.g. dacarbazine or temozolomide), topoisomerase I inhibitors (such as e.g. camptothecin, topotecan or irinotecan), and cytotoxic agents (such as e.g. platinum-based drugs like cisplatin or carboplatin). The administration of the niraparib salt may take place before, during and/or after treatment with the second therapy. A regimen for such a combination treatment could readily be determined by a clinician.

Non-Oncological Conditions

In embodiments, the methods of the disclosure are used to treat a condition in a subject selected from a neurological or neurodegenerative disease, an inflammatory disease, a metabolic disease, and a cardiovascular disease or condition. Examples of such diseases are described by Curtin et al. (*Mol Aspects Med.* (2013) 34(6):1217-1256).

In one embodiment, the method treats a subject who has suffered from, or is at risk of suffering from stroke. In another embodiment, the method treats a subject suffering from traumatic brain injury. In a further embodiment, the method treats a subject who suffers from, or is at risk of suffering from, autoimmune diabetes.

In embodiments, the neurodegenerative disease is Parkinson's disease. In embodiments, the inflammatory disease is asthma or multiple sclerosis. In embodiments, the cardiovascular disease or condition is myocardial infarction, circulatory shock, polytrauma, or acute respiratory distress syndrome.

Administration and Dosages

2-{4-[(3S)-piperidin-3-yl]phenyl}-2H-indazole-7-carboxamide (niraparib) salts as described herein can be formulated as a pharmaceutical composition for oral, buccal, parenteral (e.g. intravenous, intraperitoneal, intramuscular or subcutaneous), topical, rectal or intranasal administration or in a form suitable for administration by inhalation or insufflation. Such modes of administration and the methods for preparing appropriate pharmaceutical compositions are described, for example, in Gibaldi's Drug Delivery Systems in Pharmaceutical Care (1st ed., American Society of Health-System Pharmacists 2007).

In embodiments, an exemplary dosage regimen for niraparib is one or more 100 mg doses taken orally once daily (e.g. two doses equivalent to a total daily dose of 200 mg or three doses equivalent to a total daily dose of 300 mg). Patients may be encouraged to take their dose at approximately the same time each day. Bedtime administration may be a potential method for managing nausea.

In some embodiments, the methods of the invention treat subjects with a cancer with a dosage of 1 mg, 5 mg, 10 mg, 20 mg, 25 mg, 35 mg, 50 mg, 75 mg, 100 mg, 125 mg, 150 mg, 175 mg, 200 mg, 225 mg, 250 mg to 275 mg, 300 mg, 325 mg, 350 mg 375 mg, 400 mg, 425 mg, 450 mg, 475 mg, 500 mg, 550 mg, 600 mg, 650 mg, 700 mg, 750 mg, 800 mg, 850 mg, 900 mg, 950 mg, 1000 mg, 1050 mg, 1100 mg, 1150 mg, 1200 mg, 1250 mg, 1300 mg, 1350 mg, 1400 mg, 1450 mg, 1500 mg, 1550 mg, 1600 mg, 1650 mg, 1700 mg, 1750 mg, 1800 mg, 1850 mg, 1900 mg, 1950 mg, or 2000 mg of niraparib or pharmaceutically acceptable salt thereof once-daily, twice-daily, or thrice-daily. In some embodiments, the methods of the invention treat subjects with a cancer with a dosage of 150 mg to 175 mg, 170 mg to 195 mg, 190 mg to 215 mg, 210 mg to 235 mg, 230 mg to 255 mg, 250 mg to 275 mg, 270 to 295 mg, 290 mg to 315 mg, 310 mg to 335 mg, 330 mg to 355 mg, 350 mg to 375 mg, or 370 mg to 400 mg of niraparib or pharmaceutically acceptable salt thereof once-daily, twice-daily, or thrice-daily. In some embodiments, the methods of the invention treat subjects with a cancer with a dosage of 5 mg, 7.5 mg, 10 mg, 12.5 mg, 15 mg. 17.5 mg, 20 mg, 22.5 mg, 25 mg, 27.5 mg, 30 mg, 35 mg, 40 mg, 45 mg, 50 mg, 55 mg, 60 mg, 65 mg, 70 mg, 75 mg, 80 mg, 85 mg, 90 mg, 95 mg, or 100 mg of niraparib or pharmaceutically acceptable salt thereof once-daily, twice-daily, or thrice-daily.

In some embodiments, the methods of the invention treat subjects with a cancer with a dosage of from about 1 mg to 5 mg, 5 mg to 10 mg, 10 mg to 20 mg, 20 mg to 25 mg, 35 mg to 50 mg, 50 mg to 75 mg, 70 mg to 95 mg, 90 mg to 115 mg, 110 mg to 135 mg, 130 mg to 155 mg, 150 mg to 175 mg, 170 to 195 mg, 190 mg to 215 mg, 210 mg to 235 mg, 230 mg to 255 mg, 250 mg to 275 mg, 270 mg to 300 mg, 290 mg to 315 mg, 310 mg to 335 mg, 330 mg to 355 mg, 350 mg to 375 mg, 370 mg to 400 mg, 400 mg to 450 mg, 450 mg to 500 mg, 500 mg to 550 mg, 550 mg to 600 mg, 600 mg to 650 mg, 650 mg to 700 mg, 700 mg to 750 mg, 750 mg to 800 mg, 800 mg to 850 mg, 850 mg to 900 mg, 900 mg to 950 mg, 950 mg to 1000 mg, 1000 mg to 1050 mg, 1050 mg to 1100 mg, 1100 mg to 1150 mg, 1150 mg to 1200 mg, 1200 mg to about 1250 mg, 1250 mg to 1300 mg, 1300 mg to 1350 mg, 1350 mg to 1400 mg, 1400 mg to 1450 mg, 1450 mg to 1500 mg, 1500 mg to 1550 mg, 1550 mg to 1600 mg, 1600 mg to 1650 mg, 1650 mg to 1700 mg, 1700 mg to 1750 mg, 1750 mg to 1800 mg, 1800 mg to 1850 mg, 1850 mg to 1900 mg, 1900 mg to 1950 mg, or 1950 mg to 2000 mg of niraparib or pharmaceutically acceptable salt thereof once-daily, twice-daily, or thrice-daily. In some embodiments, the methods of the invention treat subjects with a cancer with a dosage of from about 5 mg to 7.5 mg, 7 mg to 9.5 mg, 9 mg to 11.5 mg, 11 mg to 13.5 mg, 13 mg to 15.5 mg, 15 mg to 17.5 mg, 17 to 19.5 mg, 19 mg to 21.5 mg, 21 mg to 23/5 mg, 23 mg to 25.5 mg, 25 mg to 27.5 mg, 27 mg to 30 mg, 30 mg to 35 mg, 35 mg to 40 mg, 40 mg to 45 mg, 45 mg to 50 mg, 50 mg to 55 mg, 55 mg to 60 mg, 60 to 65 mg, 65 mg to 70 mg, 70 mg to 75 mg, 75 mg to 80 mg, 80 mg to 85 mg, 85 mg to 90 mg, 90 mg to 95 mg, or 95 mg to 100 mg of niraparib or pharmaceutically acceptable salt thereof once-daily, twice-daily, or thrice-daily.

In a preferred embodiment, the niraparib salt is formulated for oral administration, e.g. in solid form.

In a preferred embodiment, the pharmaceutical composition is an oral composition, more preferably a solid oral dosage form, such as e.g. a tablet, capsule, powder, granule or sachet. The oral composition may be provided in the form of unit dosages, wherein one or more of the unit dosages, taken together, provide(s) an effective amount for administration to the subject.

In solid dosage forms for oral administration (e.g. capsules, tablets, pills, dragees, powders, granules and the like), the active ingredient is mixed with one or more pharmaceutically acceptable excipients as described herein. In the case of capsules, tablets, and pills, the pharmaceutical compositions can also comprise buffering agents. Solid compositions of a similar type can also be prepared using fillers in soft and hard-filled gelatine capsules, and excipients such as lactose or milk sugars, as well as high molecular weight polyethylene glycols and the like. By way of an example, where the pharmaceutical composition is a provided in the form of a capsule, the composition can comprise one or more components which are combined to create a powder blend that is used to fill the capsule. The powder blend may, for example, be filled into gelatin capsules, such as size 0 gelatin capsules. In such cases, the term "pharmaceutical composition" is generally to be understood as referring to the content of the capsule, i.e. the powder blend.

A tablet can be made by compression or moulding, optionally with one or more accessory ingredients. Compressed tablets can be prepared using binders (for example, gelatine or hydroxypropylmethyl cellulose), lubricants, inert diluents, preservatives, disintegrants (for example, sodium starch glycolate or cross-linked sodium carboxymethyl cellulose), surface-actives, and/or dispersing agents. Molded tablets can be made by molding in a suitable machine a mixture of the powdered active ingredient moistened with an inert liquid diluent. The tablets and other solid dosage forms, such as dragees, capsules, pills, and granules, can optionally be scored or prepared with coatings and shells, such as enteric coatings and other coatings well known in the art.

In embodiments, a solid dosage form for administering a therapeutically effective amount of niraparib to a subject comprises the niraparib salt in an amount of from about 1 mg to about 1000 mg (based on the weight of niraparib freebase equivalent within the salt). In embodiments, the solid dosage form comprises from about 25 mg to about 750 mg of the niraparib salt, e.g. from about 50 mg to about 500 mg, from about 60 mg to about 400 mg, or from about 75 mg to about 300 mg (based on the weight of niraparib freebase equivalent within the salt). In other embodiments, the solid dosage form comprises from about 50 to about 300 mg of the niraparib salt (based on the weight of niraparib freebase equivalent within the salt). In embodiments, the solid dosage form comprises about 50 mg, 75 mg, 100 mg, 125 mg, 150 mg, 175 mg, 200 mg, 225 mg, 250 mg, 275 mg, 300 mg, 325 mg or 350 mg of the niraparib salt (based on the weight of niraparib freebase equivalent within the salt). In embodiments, a solid dosage form for administering a therapeutically effective amount of niraparib to a subject comprises the niraparib salt in an amount of greater than about 100 mg (based on the weight of niraparib freebase equivalent within the salt). In embodiments, the solid dosage form comprises greater than about 120 mg, 140 mg, 160 mg, 180 mg, 200 mg, 220 mg, 240 mg, 260 mg or 280 mg of the niraparib salt (based on the weight of niraparib freebase equivalent within the salt).

In embodiments, the solid dosage form is presented as one, two or three unit dosages. In embodiments, the solid oral dosage form is administered one, two, or three times a day such as to provide a therapeutically effective amount of niraparib for use in a method as described herein. In a preferred embodiment, the solid dosage form is presented as a single unit dosage which is administered once daily, i.e. it provides a therapeutically effective daily amount of niraparib (such as e.g. an amount of a salt which corresponds to about 300 mg of niraparib freebase). In another preferred embodiment, the solid dosage form is presented as two unit dosages which are administered together or separately, i.e. they provide between them a therapeutically effective daily amount of niraparib (such as e.g. about 150 mg per unit dosage). In another preferred embodiment, the solid dosage form is presented as three unit dosages which are administered together or separately, i.e. they provide between them a therapeutically effective daily amount of niraparib (such as e.g. about 100 mg per unit dosage).

For buccal administration, the composition may take the form of tablets or lozenges formulated in a conventional manner.

In some embodiments, the pharmaceutical compositions are administered by non-oral means such as by topical application, transdermal application, injection, and the like. In related embodiments, the pharmaceutical compositions are administered parenterally by injection, infusion, or implantation (e.g. intravenous, intramuscular, intra-arterial, subcutaneous, and the like). In each case, it is preferred that the pharmaceutical composition is stored and/or used in a solid form, so as to take advantage of the properties of the niraparib salt.

The pharmaceutical compositions can be suitable for the preparation of injectable formulations for parenteral administration, including using conventional catheterisation techniques or infusion. Formulations for injection may be presented in unit dosage form, e.g. in ampules or in multi-dose containers, with an added preservative. The compositions may take such forms as suspensions or emulsions in oily or aqueous vehicles, and may contain a formulating agent such as a suspending, stabilising and/or dispersing agent recognised by those of skill in the art. Alternatively, the active ingredient may be in powder form for reconstitution with a suitable vehicle, e.g. sterile pyrogen-free water, before use.

The pharmaceutical compositions can be suitable for the preparation of sterile injectable formulations. Those formulations can be sterilised by, for example, filtration through a bacteria-retaining filter, or by incorporating sterilising agents in the form of sterile solid compositions which can be dissolved in sterile water, or some other sterile injectable medium immediately before use. To prepare such a composition, the active ingredient is dissolved or suspended in a parenterally acceptable liquid vehicle. Exemplary vehicles and solvents include, but are not limited to, water, water adjusted to a suitable pH by addition of an appropriate amount of hydrochloric acid, sodium hydroxide or a suitable buffer, 1,3-butanediol, Ringer's solution and isotonic sodium chloride solution. The pharmaceutical composition can also contain one or more preservatives, for example, methyl, ethyl or n-propyl p-hydroxybenzoate. To improve solubility, a dissolution enhancing or solubilising agent can be added or the solvent can contain 10-60% w/w of propylene glycol or the like.

The pharmaceutical compositions can contain one or more pharmaceutically acceptable sterile isotonic aqueous or nonaqueous solutions, dispersions, suspensions or emulsions, or sterile powders, which can be reconstituted into sterile injectable solutions or dispersions just prior to use. Such pharmaceutical compositions can contain antioxidants; buffers; bacteriostats; solutes, which render the formulation isotonic with the blood of the intended recipient; suspending agents; thickening agents; preservatives; and the like.

Examples of suitable aqueous and nonaqueous carriers, which can be employed in the pharmaceutical compositions of the invention include water, ethanol, polyols (such as glycerol, propylene glycol, polyethylene glycol, and the like), and suitable mixtures thereof, vegetable oils, such as olive oil, and injectable organic esters, such as ethyl oleate. Proper fluidity can be maintained, for example, by the use of coating materials, such as lecithin, by the maintenance of the required particle size in the case of dispersions, and by the use of surfactants. In some embodiments, in order to prolong the effect of an active ingredient, it is desirable to slow the absorption of the compound from subcutaneous or intramuscular injection. This can be accomplished by the use of a liquid suspension of crystalline material having poor water solubility. The rate of absorption of the active ingredient then depends upon its rate of dissolution which, in turn, can depend upon crystal size and crystalline form. Alternatively, delayed absorption of a parenterally-administered active ingredient is accomplished by dissolving or suspending the compound in an oil vehicle. In addition, prolonged absorption of the injectable pharmaceutical form can be brought about by the inclusion of agents that delay absorption such as aluminium monostearate and gelatine.

Controlled release parenteral compositions can be in form of aqueous suspensions, microspheres, microcapsules, magnetic microspheres, oil solutions, oil suspensions, emulsions, or the active ingredient can be incorporated in biocompatible carrier(s), liposomes, nanoparticles, implants or infusion devices. Materials for use in the preparation of microspheres and/or microcapsules include, but are not limited to, biodegradable/bioerodible polymers such as polyglactin, poly-(isobutyl cyanoacrylate), poly(2-hydroxyethyl-L-glutamine) and poly(lactic acid). Biocompatible carriers which can be used when formulating a controlled release parenteral formulation include carbohydrates such as dextrans, proteins such as albumin, lipoproteins or antibodies. Materials for use in implants can be non-biodegradable, e.g. polydimethylsiloxane, or biodegradable such as, e.g., poly(caprolactone), poly(lactic acid), poly(glycolic acid) or poly(ortho esters).

For topical administration, the niraparib salt may be formulated as an ointment or cream. The niraparib salt may also be formulated in rectal compositions such as suppositories or retention enemas, e.g. containing conventional suppository bases such as cocoa butter or other glycerides.

For intranasal administration or administration by inhalation, the niraparib salt may be conveniently delivered in the form of a solution or suspension from a pump spray container that is squeezed or pumped by the patient or as an aerosol spray presentation from a pressurised container or a nebulizer, with the use of a suitable propellant, e.g. dichlorodifluoromethane, trichlorofluoromethane, dichlorotetrafluoroethane, carbon dioxide or other suitable gas. In the case of a pressurised aerosol, the dosage unit may be determined by providing a valve to deliver a metered amount. The pressurised container or nebulizer may contain a solution or suspension. Capsules and cartridges (made, for example, from gelatine) for use in an inhaler or insufflator may be formulated containing a powder mix of the niraparib salt and a suitable powder base such as lactose or starch.

In other aspects, the invention provides a dosage form or pharmaceutical composition as described herein for use in therapy, e.g. for use in a method as defined herein.

In other aspects, the invention provides an article of manufacture (e.g. a kit) comprising multiple unit doses of a pharmaceutical composition as described herein in a sealed container with written instructions for use. In embodiments, the article of manufacture further comprises an induction seal, a desiccant, or a combination thereof.

Combination Therapies

Crystalline forms of 2-{4-[(3S)-piperidin-3-yl]phenyl}-2H-indazole-7-carboxamide (niraparib) salts described herein can be useful as monotherapy or in combination therapy with the administration of one or more additional therapeutic agents or lines of therapy.

For example, a crystalline form of a 2-{4-[(3S)-piperidin-3-yl]phenyl}-2H-indazole-7-carboxamide (niraparib) salt described herein can be administered in combination with surgery, a radiotherapy, a chemotherapy, an immunotherapy, an anti-angiogenic agent, or an anti-inflammatory agent.

Where a crystalline form of a 2-{4-[(3S)-piperidin-3-yl]phenyl}-2H-indazole-7-carboxamide (niraparib) salt is administered in combination with one or more different therapeutic agents (e.g. as described herein), administering of the crystalline form of a niraparib salt can occur sequentially with the administering of the one or more different therapeutic agents. For example, administration of the crystalline form of a niraparib salt occurs before administration of the one or more different therapeutic agents. In embodiments, administration of the crystalline form of a niraparib salt occurs after administration of the one or more different therapeutic agents. In other embodiments, administering of the crystalline form of a niraparib salt occurs simultaneously with the administering of the one or more different therapeutic agents.

In embodiments, a crystalline form of a niraparib salt described herein is administered in combination with one or more immune checkpoint inhibitors. In embodiments, a checkpoint inhibitor is an agent capable of inhibiting any of the following: PD-1 (e.g. inhibition via anti-PD-1, anti-PD-L1, or anti-PD-L2 therapies), CTLA-4, TIM-3, TIGIT, LAGs (e.g. LAG-3), CEACAM (e.g. CEACAM-1, -3 and/or -5), VISTA, BTLA, LAIR1, CD160, 2B4, CD80, CD86, B7-H3 (CD276), B7-H4 (VTCN1), HVEM (TNFRSF14 or CD270), KIR, A2aR, MHC class I, MHC class II, GALS, adenosine, TGFR (e.g. TGFR beta), B7-H1, B7-H4 (VTCN1), OX-40, CD137, CD40, IDO, or CSF-1R. In embodiments, a checkpoint inhibitor is a small molecule, a nucleic acid, a polypeptide (e.g. an antibody), a carbohydrate, a lipid, a metal, or a toxin. In embodiments, a checkpoint inhibitor is an antibody, an antibody conjugate, or an antigen-binding fragment thereof.

In embodiments, an immune checkpoint inhibitor is a PD-1 inhibitor. In embodiments, a PD-1 inhibitor is a small molecule, a nucleic acid, a polypeptide (e.g. an antibody, an antibody conjugate, or an antigen-binding fragment thereof), a carbohydrate, a lipid, a metal, or a toxin. In embodiments, a PD-1 inhibitor is a PD-1 binding agent (e.g. an antibody, an antibody conjugate, or an antigen-binding fragment thereof). In embodiments, a PD-1 binding agent is an antibody, an antibody conjugate, or an antigen-binding fragment thereof. In embodiments, a PD-1 binding agent is TSR-042, nivolumab, pembrolizumab, atezolizumab, durvalumab, avelumab, PDR-001, tislelizumab (BGB-A317), cemiplimab (REGN2810), LY-3300054, JNJ-63723283, MGA012, BI-754091, IBI-308, camrelizumab (HR-301210), BCD-100, JS-001, CX-072, BGB-A333, AMP-514 (MEDI-0680), AGEN-2034, CS1001, Sym-021, SHR-1316, PF-06801591, LZM009, KN-035, AB122, genolimzumab (CBT-501), FAZ-053, CK-301, AK 104, or GLS-010. In embodiments, a PD-1 inhibitor is a PD-L1 or PD-L2 binding agent such as durvalumab, atezolizumab, avelumab, BGB-A333, SHR-1316, FAZ-053, CK-301, or, PD-L1 millamolecule, or derivatives thereof. In embodiments, an anti-PD-1 agent is pembrolizumab. In embodiments, an anti-PD-1 agent is nivolumab. In some embodiments, a PD-1 antibody agent is as disclosed in International Patent Application Publication Nos. WO2014/179664, WO 2018/085468, or WO 2018/129559. In further embodiments, a PD-1 antibody agent is administered according to a method disclosed in International Patent Application Publication Nos. WO2014/179664, WO 2018/085468, or WO 2018/129559. In embodiments, an anti-PD-1 agent is TSR-042.

In embodiments, an immune checkpoint inhibitor is a TIM-3 inhibitor. In embodiments, a TIM-3 inhibitor is a small molecule, a nucleic acid, a polypeptide (e.g. an antibody, an antibody conjugate, or an antigen-binding fragment thereof), a carbohydrate, a lipid, a metal, or a toxin. In embodiments, a TIM-3 inhibitor is a TIM-3 binding agent (e.g. an antibody, an antibody conjugate, or an antigen-binding fragment thereof). In embodiments, a TIM-3 binding agent is an antibody, an antibody conjugate, or an antigen-binding fragment thereof. In some embodiments, a TIM-3 antibody agent is MBG453, LY3321367, Sym023, TSR-022, or a derivative thereof. In some embodiments, a TIM-3 antibody agent is as disclosed in International Patent Application Publication Nos. WO2016/161270, WO 2018/085469, or WO 2018/129553. In some embodiments, a TIM-3 antibody agent is administered as disclosed in International Patent Application Publication Nos. WO2016/161270, WO 2018/085469, or WO 2018/129553. In some embodiments, a TIM-3 antibody agent is TSR-022.

In embodiments, an immune checkpoint inhibitor is a LAG-3 inhibitor. In embodiments, an anti-LAG-3 agent is an antibody, an antibody conjugate, or an antigen-binding fragment thereof. In embodiments, an anti-LAG-3 agent is a small molecule, a nucleic acid, a polypeptide (e.g. an antibody), a carbohydrate, a lipid, a metal, or a toxin. In embodiments, an anti-LAG-3 agent is a small molecule. In embodiments, an anti-LAG-3 agent is a LAG-3 binding agent. In embodiments, an anti-LAG-3 agent is an antibody, an antibody conjugate, or an antigen-binding fragment thereof. In embodiments, an anti-LAG-3 agent is IMP321, relatlimab (BMS-986016), BI 754111, GSK2831781 (IMP-731), Novartis LAG525 (IMP701), REGN3767, MK-4280, MGD-013, GSK-2831781, FS-118, XmAb22841, INCAGN-2385, FS-18, ENUM-006, AVA-017, AM-0003, Avacta PD-L1/LAG-3 bispecific affamer, iOnctura anti-LAG-3 antibody, Arcus anti-LAG-3 antibody, or Sym022, or TSR-033. In some embodiments, a LAG-3 antibody agent is as disclosed in International Patent Application Publication WO2016/126858 or in in International Patent Application No. PCT/US18/30027. In some embodiments, a LAG-3 antibody agent is administered as disclosed in International Patent Application Publication WO2016/126858 or in in International Patent Application No. PCT/US18/30027. In embodiments, a LAG-3 antibody agent is TSR-033.

In embodiments, a niraparib tablet composition is administered in combination with a PD-1 inhibitor (e.g. TSR-042, pembrolizumab, or nivolumab). In embodiments, a niraparib tablet composition is administered in combination with a TIM-3 inhibitor (e.g. TSR-022). In embodiments, a niraparib tablet composition is administered in combination with a LAG-3 inhibitor (e.g. TSR-033). In embodiments, a niraparib tablet composition is administered in combination with a PD-1 inhibitor (e.g. TSR-042, pembrolizumab, or nivolumab) and a TIM-3 inhibitor (e.g. TSR-022). In embodiments, a niraparib tablet composition is administered in combination with a PD-1 inhibitor (e.g. TSR-042, pembrolizumab, or nivolumab) and a LAG-3 inhibitor (e.g. TSR-033). In embodiments, a niraparib tablet composition is administered in combination with a TIM-3 inhibitor (e.g. TSR-022) and a LAG-3 inhibitor (e.g. TSR-033). In embodiments, a niraparib tablet composition is administered in combination with a PD-1 inhibitor (e.g. TSR-042, pembrolizumab, or nivolumab), a TIM-3 inhibitor (e.g. TSR-022), and a LAG-3 inhibitor (e.g. TSR-033).

In embodiments, a niraparib tablet composition is administered in combination with one or more chemotherapy agents.

In embodiments, a niraparib tablet composition is administered in combination with a platinum-based chemotherapy agent (e.g. one or more of cisplatin, carboplatin, oxaliplatin, nedaplatin, triplatin tetranitrate, phenanthriplatin, picoplatin, and satraplatin).

In embodiments, a niraparib tablet composition is administered in combination with a chemotherapy agent that is aminoglutethimide, amsacrine, anastrozole, asparaginase, beg, bicalutamide, bleomycin, buserelin, busulfan, campothecin, capecitabine, carboplatin, carmustine, chlorambucil, cisplatin, cladribine, clodronate, colchicine, cyclophosphamide, cyproterone, cytarabine, dacarbazine, dactinomycin, daunorubicin, dienestrol, diethylstilbestrol, docetaxel, doxorubicin, epirubicin, estradiol, estramnustine, etoposide, exemestane, filgrastim, fludarabine, fludrocortisone, fluorouracil, fluoxymesterone, flutamide, gemcitabine, genistein, goserelin, hydroxyurea, idarubicin, ifosfamide, imatinib, interferon, irinotecan, ironotecan, letrozole, leucovorin, leuprolide, levamisole, lomustine, mechlorethamine, medroxyprogesterone, megestrol, melphalan, mercaptopurine, mesna, methotrexate, mitomycin, mitotane, mitoxantrone, nilutamide, nocodazole, octreotide, oxaliplatin, paclitaxel, pamidronate, pentostatin, plicamycin, porfimer, procarbazine, raltitrexed, rituximab, streptozocin, suramin, tamoxifen, temozolomide, teniposide, testosterone, thioguanine, thiotepa, titanocene dichloride, topotecan, trastuzumab, tretinoin, vinblastine, vincristine, vindesine, or vinorelbine.

In embodiments, a niraparib tablet composition is administered in combination with a second agent that is a regulatory T cell (Treg) inhibitory agent, a macrophage inhibitory agent, an antigen specific immune response enhancer agent, antigen specific immune response enhancer agent, anti-angiogenic agent, a chemotherapy agent or a combination thereof. In embodiments, a second agent is any second agent described in International Application No. PCT/US18/33437, herein incorporated by reference in its entirety.

In embodiments, a macrophage inhibitory agent is selected from the group consisting of a macrophage recruitment inhibitory agent (e.g. an anti-CCL2/CCR2 agent, an anti-IL6 agent, an anti-M-CSFR agent, and combinations thereof), an M2 macrophage antisurvival agent, an M1 macrophage enhancing agent, an M2 to M1 polarizing agent, a macrophage activity inhibitor agent and combinations thereof. In embodiments, a macrophage recruitment inhibitory agent is selected from the group consisting of trabectedin, RS102895, PF-04136309, CNT0888, MLN1202, siltuximab, JNJ-28312141, GW2580, IMC-CS4 (LY3022855), emactuzumab, AMG820, pexidartinib, linifanib, OSI-930, CEP-32496, PLX7846, BLZ945, ARRY-382, JNJ-40346527, MCS110, PLX3397, PLX6134, PD-0360324, FPA008, and combinations thereof. In embodiments, a M2 macrophage antisurvival agent is selected from the group consisting of an MMP inhibitor, clodronate, zoledronic acid, dichloromethylene bisphosphonate, trabectedin, dasatinib, retinoic acid, attenuated bacteria (e.g. *Shigella flexneri, Salmonella typhimurium, Listeria monocytogens, Chlamydia psittaci, Legionella pneumophila*), and combinations thereof. In embodiments, a M1 macrophage enhancing agent or the M2 to M1 polarizing agent is selected from the group consisting of an anti-CD40 agent, an anti-IL-10R agent, a CD47 antagonist (e.g. Hu5F9-G4, CC-90002, and CD47-Fc fusion protein TTI-621), PolyI:C, LPS, monophosphoryl A, imiquimod, R-848, CpG-ODN, IFN-α, IFN-β, IFN-γ, GM-CSF, IL-12, IL-2, IL-15, Tα1, ibrutinib, EF-022 and combinations thereof. In embodiments, macrophage activity inhibitory agent is selected from the group consisting of a STAT3 inhibitor, a STAT6 inhibitor, or an anti-tumor drug agent (e.g. a macrophage activity inhibitory agent is WP1066, sunitinib, sorafenib, STA-21, IS3 295, S3I-M2001, AS1517499, leflunomide, TMC-264, histidine-rich glycoprotein (HRG), copper chelate (CuNG), 5,6-dimethyl-xanthenone-4-acetic acid (MDXAA), vadimezan (ASA404), cisplatin, silibinin, proton pump inhibitor pantoprazole (PPZ), or CNI-1493, or combinations thereof). In embodiments, a macrophage inhibitor agent is an anti-IL-1α agent (e.g. xilonix).

In embodiments a regulatory T cell (Treg) inhibitory agent is selected from the group consisting of a Treg ablating agent, a Treg migration inhibitor agent, a Treg function inhibitor agent, and combinations thereof. In embodiments, a Treg ablating agent is selected from the group consisting of cyclophosphamide, paclitaxel, imatinib, sunitinib, sorafenib, dasatinib, temozolomide, daclizumab, denileukin diftitox, and combinations thereof. In embodiments, a Treg migration inhibitor agent is selected from the group consisting of AMD3100, mogamulizumab, casuarinin, fucoidan, and combinations thereof. In embodiments, a Treg function inhibitor agent is selected from the group consisting of an anti-CTLA4 agent (e.g. ipilimumab, tremelimumab), an anti-OX40 agent, an anti-GITR agent, an adenosine receptor antagonist (e.g. caffeine, theophylline, theobromine, and 8-phenylxanthines), P60, and combinations thereof.

In embodiments, an antigen specific immune response enhancer agent is selected from the group consisting of an anti-PD-1 agent, an anti-PD-L1 agent, a GITR (glucocorticoid-induced TNFR-related protein) stimulating agent, an anti-CTLA4 agent, an anti-TIM-3 agent, an anti-LAG-3 agent, an anti-IDO agent, an agent that enhances tumor antigen presentation (e.g. personalized cancer vaccine, autologous antigen presenting cell, autologous dendritic cells, artificial antigen presenting cell), a chemokine signaling agent, an anti-VEGF agent, a cytokine signal stimulating agent, and combinations thereof.

In embodiments, a GITR stimulating agent is selected from the group consisting of DTA-1, mGITRL, pGITRL, and combinations thereof. In embodiments, an anti-CTLA4 agent is selected from the group consisting of ipilimumab, tremelimumab, and combinations thereof. In embodiments, a chemokine signaling agent is selected from the group consisting of CXCL16, a CXCR6 chemokine receptor (CD186) agonist, and combinations thereof. In embodiments, an anti-VEGF agent is selected from the group consisting of bevacizumab, pazopanib, sunitinib, sorafenib, axitinib, ponatinib, regorafenib, cabozantinib, vandetanib, ramucirumab, lenvatinib, ziv-aflibercept, and combinations thereof. In embodiments, a cytokine signal stimulating agent is an interleukin or an interferon. In embodiments, an interleukin is selected from the group consisting of IL-2, IL-1, IL-7, IL-15, IL-12, IL-18 and combinations thereof. In embodiments, an interferon is IFN alpha.

In embodiments, an antigen specific immune response enhancer agent is selected from the group consisting of a flavonoid (e.g. flavonoid glycoside), lidocaine, lamotrigine, sulfamethoxazole, phenytoin, carbamazepine, sulfamethoxazole, phenytoin, allopurinol, paracetamol, mepivacaine, p-phenylenediamine, ciprofloxacin and moxifloxacin.

In embodiments, an anti-angiogenic agent is TNP-470, platelet factor 4, thrombospondin-1, tissue inhibitors of metalloproteases (TIMP1 and TIMP2), prolactin, angiostatin, endostatin, bFGF soluble receptor, transforming growth factor beta, interferon alpha, soluble KDR and FLT-1 receptors, placental proliferin-related protein, and combinations thereof. In embodiments, an anti-angiogenic agent reduces the production of a pro-angiogenic factor, inhibits an interaction between a pro-angiogenic factor and a pro-angiogenic receptor, inhibits a function of a pro-angiogenic factor, inhibits a function of a pro-angiogenic factor receptor, reduces of blood flow by disruption of blood vessels, inhibits vessel sprouting, or any combinations thereof. In embodiments, an anti-angiogenic agent is a small organic or inorganic molecule; a saccharine; an oligosaccharide; a polysaccharide; a carbohydrate; a peptide; a protein; a peptide analog; a peptide derivative; a lipid; an antibody; an antibody fragment, a peptidomimetic; a nucleic acid; a nucleic acid analog; a nucleic acid derivative; an extract made from biological materials; a naturally occurring or synthetic composition; a metal; a toxin; or any combination thereof. In embodiments, an anti-angiogenic agent is selected from the group consisting of bevacizumab, itraconazole, carboxyamidotriazole, TNP-470, fumagillin, CM101, IL-12, platelet factor-4, suramin, SU5416, thrombospondin, angiostatic steroids, heparin, cartilage-derived angiogenesis inhibitory factor, matrix metalloproteinase inhibitor, angiostatin, endostatin, 2-methoxyestradiol, tecogalan, tetrathiomolybdate, thrombospondin, thalidomide, prolactin, αVβ3 inhibitor, lenalidomide, linomide, ramucirumab, tasquinimod, ranibizumab, sorafenib, sunitinib, pazopanib, everolimus, tissue inhibitors of metalloproteases (TIMP1 and TIMP2), bFGF soluble receptor, transforming growth factor beta, interferon alpha, soluble KDR and FLT-1 receptors, placental proliferin-related protein, pazopanib, sunitinib, sorafenib, axitinib, ponatinib, cabozantinib, regorafenib, vandetanib, lenvatinib, semaxanib, SU6668, vatalanib, tivozanib, cediranib, protamine, heparin, steroids, ascorbic acid ethers, sulfated polysaccharide DS 4152, fumagillin, AGM 12470, neovastat, RO4929097, MRK-003, MK-0752, PF03084014, MED10639, curcumin, 3,3'-diindolylmethane (DIM), resveratrol, 3,5-bis(2,4-difluorobenzylidene)-4-piperidone (DiFiD) and epigallocatechin-3-gallate (EGCG), honokiol, OMP-21M18, navicixizumab (OMP-305B83), $Flt_{2-11}$, CBO-P11, Je-11, V1, and any combination thereof.

In some embodiments, an anti-angiogenic agent inhibits a DLL4/Notch signaling pathway.

In some embodiments, the angiogenesis inhibitor inhibiting the DLL4/Notch signaling pathway is a gamma-secretase inhibitor (GSI), a siRNA, or a monoclonal antibody against a Notch receptor or ligand. In some embodiments, an anti-angiogenic agent is selected from the group consisting of RO4929097, MRK-003, MK-0752, PF03084014, MED10639, curcumin, 3,3'-diindolylmethane (DIM), resveratrol, 3,5-bis(2,4-difluorobenzylidene)-4-piperidone (DiFiD) and epigallocatechin-3-gallate (EGCG), honokiol, and any combination thereof.

In some embodiments, an anti-angiogenic agent inhibits a vascular endothelial growth factor (VEGF)/vascular endothelial growth factor receptor (VEGFR) pathway. In some embodiments, an anti-angiogenic agent is selected from the group consisting of Akt Inhibitor, calcineurin autoinhibitory peptide, ET-18-OCH3, Go 6983, NG-Nitro-L-arginine methyl ester, p21-activated kinase Inhibitor, cPLA2α inhibitor, PI-103, PP2, SB 203580, U0126, VEGFR tyrosine kinase inhibitor V, VEGFR2 kinase inhibitor VI, VEGFR2 kinase inhibitor III, ZM 336372, and any combination thereof.

In some embodiments, an anti-angiogenic agent inhibits a VEGF family protein and/or a VEGFR family protein. In some embodiments, the VEGF family protein comprises VEGF-A, VEGF-B, VEGF-C, VEGF-D, P1GF (placental growth factor), VEGF-E (Orf-VEGF), *Trimeresurus flavoviridis* svVEGF, or any combination thereof. In some embodiments, an anti-angiogenic agent is bevacizumab, ranibizumab, OPT-302, ziv-aflibercept, or any combinations thereof. In some embodiments, an anti-angiogenic agent is Flt2-11, CBO-P11, Je-11, V1, or any combination thereof. In some embodiments, an anti-angiogenic agent is pazopanib, sunitinib, sorafenib, axitinib, ponatinib, cabozantinib, regorafenib, vandetanib, lenvatinib, semaxanib, SU6668, vatalanib, tivozanib, cediranib, or any combination thereof.

Having been generally described herein, the follow non-limiting examples are provided to further illustrate this invention.

EXEMPLARY ASPECTS AND EMBODIMENTS OF THE INVENTION

Exemplary aspects and embodiments of the invention are described herein and include items 1-125.

Item 1. A 2-{4-[(3S)-piperidin-3-yl]phenyl}-2H-indazole-7-carboxamide (niraparib) salt selected from niraparib camphorate, niraparib mandelate and niraparib camsylate.

Item 2. 2-{4-[(3S)-piperidin-3-yl]phenyl}-2H-indazole-7-carboxamide (niraparib) camphorate.

Item 3. 2-{4-[(3S)-piperidin-3-yl]phenyl}-2H-indazole-7-carboxamide (niraparib) (1R,3S)-(+)-camphorate.

Item 4. Crystalline 2-{4-[(3S)-piperidin-3-yl]phenyl}-2H-indazole-7-carboxamide (niraparib) (1R,3S)-(+)-camphorate.

Item 5. A crystalline Form 1 of 2-{4-[(3S)-piperidin-3-yl]phenyl}-2H-indazole-7-carboxamide (niraparib) (1R,3S)-(+)-camphorate.

Item 6. The crystalline Form 1 of niraparib (1R,3S)-(+)-camphorate according to item 5, having an X-ray powder diffraction (XRPD) pattern comprising one or more XRPD peaks at 16.2, 17.5, 20.0, 13.4 and/or 15.2±0.2° 2θ.

Item 7. The crystalline Form 1 of niraparib (1R,3S)-(+)-camphorate according to item 5 or item 6, having an XRPD pattern comprising at least two peaks at 16.2, 17.5, 20.0, 13.4 and/or 15.2±0.2° 2θ.

Item 8. The crystalline Form 1 of niraparib (1R,3S)-(+)-camphorate according to any one of items 5-7, having an XRPD pattern comprising at least three peaks at 16.2, 17.5, 20.0, 13.4 and/or 15.2±0.2° 2θ.

Item 9. The crystalline Form 1 of niraparib (1R,3S)-(+)-camphorate according to any one of items 5-8, having an XRPD pattern comprising at least four peaks at 16.2, 17.5, 20.0 13.4 and/or 15.2±0.2° 2θ.

Item 10. The crystalline Form 1 of niraparib (1R,3S)-(+)-camphorate according to any one of items 5-9, having an XRPD pattern comprising peaks at 16.2, 17.5, 20.0, 13.4 and 15.2±0.2° 2θ.

Item 11. The crystalline Form 1 of niraparib (1R,3S)-(+)-camphorate according to any one of items 5-10, having an XRPD pattern comprising one or more XRPD peaks at 20.4, 21.6, 24.0, 11.7 and/or 18.0±0.2° 2θ.

Item 12. The crystalline Form 1 of niraparib (1R,3S)-(+)-camphorate according to any one of items 5-11, having an XRPD pattern comprising two or more peaks at 20.4, 21.6, 24.0, 11.7 and/or 18.0±0.2° 2θ.

Item 13. The crystalline Form 1 of niraparib (1R,3S)-(+)-camphorate according to any one of items 5-12, having an XRPD pattern comprising three or more peaks at 20.4, 21.6, 24.0, 11.7 and/or 18.0±0.2° 2θ.

Item 14. The crystalline Form 1 of niraparib (1R,3S)-(+)-camphorate according to any one of items 5-13, having an XRPD pattern comprising four or more peaks at 20.4, 21.6, 24.0, 11.7 and/or 18.0±0.2° 2θ.

Item 15. The crystalline Form 1 of niraparib (1R,3S)-(+)-camphorate according to any one of items 5-14, having an XRPD pattern comprising peaks at 20.4, 21.6, 24.0, 11.7 and 18.0±0.2° 2θ.

Item 16. The crystalline Form 1 of niraparib (1R,3S)-(+)-camphorate according to any one of items 5-15, having an XRPD pattern comprising peaks at 16.2, 17.5, 20.0, 13.4, 15.2, 20.4, 21.6, 24.0, 11.7 and 18.0±0.2° 2θ.

Item 17. The crystalline Form 1 of niraparib (1R,3S)-(+)-camphorate according to any one of items 5-16, having an XRPD pattern comprising at least one peak at 14.8, 18.0, 22.8 and/or 27.6±0.2° 2θ.

Item 18. The crystalline Form 1 of niraparib (1R,3S)-(+)-camphorate according to any one of items 5-17, having an XRPD pattern comprising at least two peaks at 14.8, 18.0, 22.8 and/or 27.6±0.2° 2θ.

Item 19. The crystalline Form 1 of niraparib (1R,3S)-(+)-camphorate according to any one of items 5-18, having an XRPD pattern comprising at least three peaks at 14.8, 18.0, 22.8 and/or 27.6±0.2° 2θ.

Item 20. The crystalline Form 1 of niraparib (1R,3S)-(+)-camphorate according to any one of items 5-19, having an XRPD pattern comprising peaks at 14.8, 18.0, 22.8 and 27.6±0.2° 2θ.

Item 21. The crystalline Form 1 of niraparib (1R,3S)-(+)-camphorate according to any one of items 5-20, having an XRPD pattern comprising one or more peaks at 16.2, 17.5, 20.0, 13.4, 15.2, 20.4, 21.6, 24.0, 11.7, 18.0, 22.8, 18.9, 14.5, 14.1, 14.8, 27.6, 26.9, 6.5, 22.3 and/or 24.5±0.2° 2θ.

Item 22. The crystalline Form 1 of niraparib (1R,3S)-(+)-camphorate according to any one of items 5 to 21, having an XRPD pattern comprising peaks with the 2θ values (±0.2° 2θ), and optionally also relative intensities, according to the following table:

| Pos. [°2θ] | Rel. Int. [%] |
|---|---|
| 6.5 | 15.9 |
| 11.7 | 28.9 |
| 13.4 | 51.5 |
| 14.1 | 21.1 |
| 14.5 | 23.1 |
| 14.8 | 20.6 |
| 15.2 | 48.6 |
| 16.2 | 100 |
| 17.5 | 91.3 |
| 18.0 | 26.6 |
| 18.9 | 25.4 |
| 20.0 | 59.9 |
| 20.4 | 41.2 |
| 21.6 | 35.0 |
| 22.3 | 15.8 |
| 22.8 | 26.0 |
| 24.0 | 30.3 |
| 24.5 | 13.6 |
| 26.9 | 17.4 |
| 27.6 | 17.9 |

Item 23. The crystalline Form 1 of niraparib (1R,3S)-(+)-camphorate according to any one of items 5-22 characterised by an XRPD pattern substantially as shown in FIG. 3.

Item 24. The crystalline Form 1 of niraparib (1R,3S)-(+)-camphorate according to any one of items 5-23 characterised by a melting point of about 260° C. to about 270° C.

Item 25. The crystalline Form 1 of niraparib (1R,3S)-(+)-camphorate according to any one of items 5-24 characterised by a melting point of about 264° C.

Item 26. The crystalline Form 1 of niraparib (1R,3S)-(+)-camphorate according to any one of items 5-25 characterised by a DSC thermogram in which the onset of melting (endothermic peak) is about 264° C. and/or wherein the peak minimum is about 268° C.

Figure 5:
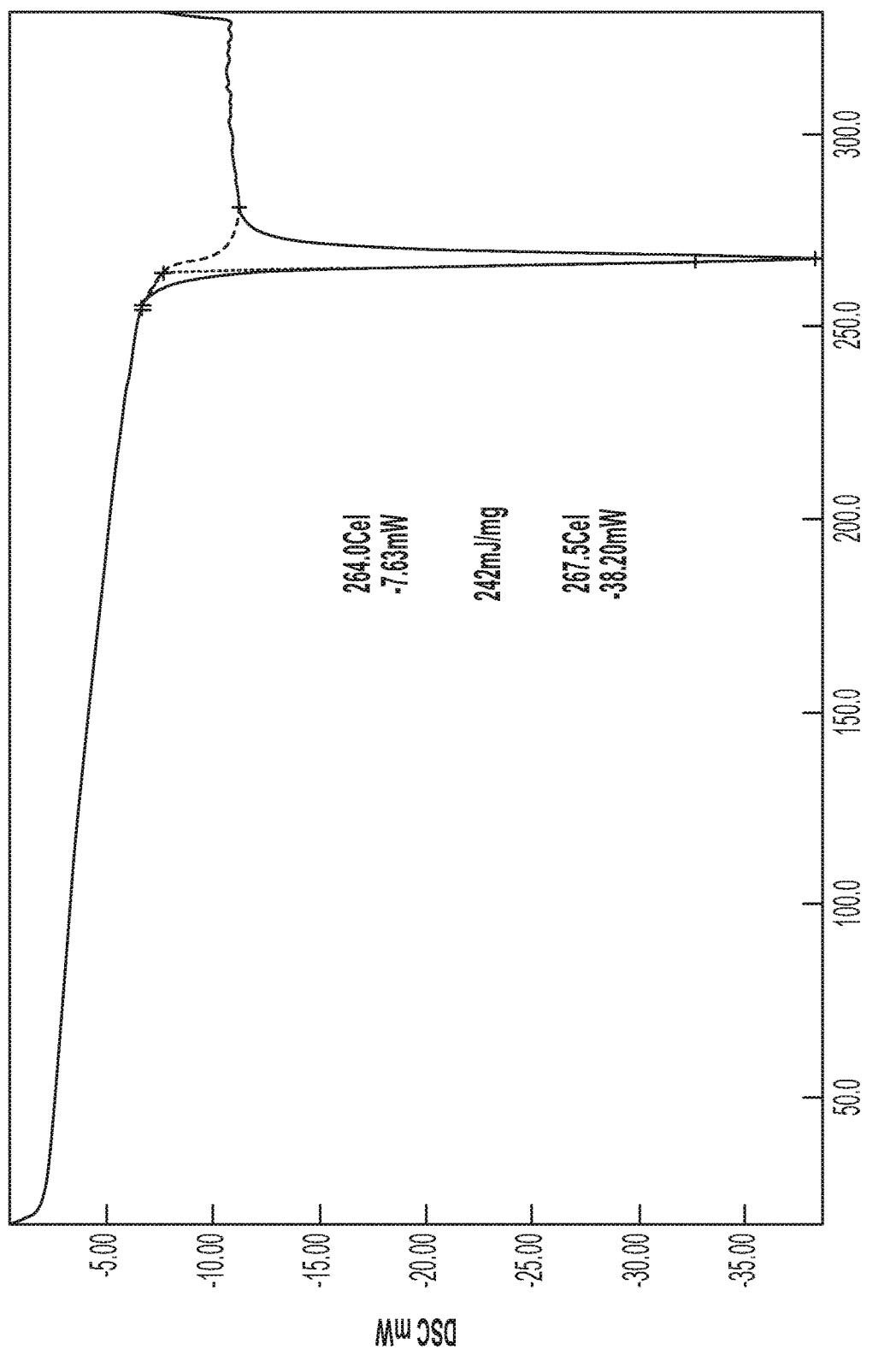
FIG. 5 shows an exemplary differential scanning calorimetry thermogram for the crystalline Form 1 of the (1R,3S)-(+)-camphorate salt of 2-{4-[(3S)-piperidin-3-yl]phenyl}-2H-indazole-7-carboxamide (niraparib).

Item 27. The crystalline Form 1 of niraparib (1R,3S)-(+)-camphorate according to any one of items 5-26 characterised by a DSC thermogram substantially as shown in FIG. 5.

Item 28. The crystalline Form 1 of niraparib (1R,3S)-(+)-camphorate according to any one of items 5-27 characterised by an infra-red spectrum comprising peaks at about 3359 cm$^{-1}$, about 1693 cm$^{-1}$ and about 1649 cm$^{-1}$.

Figure 2:
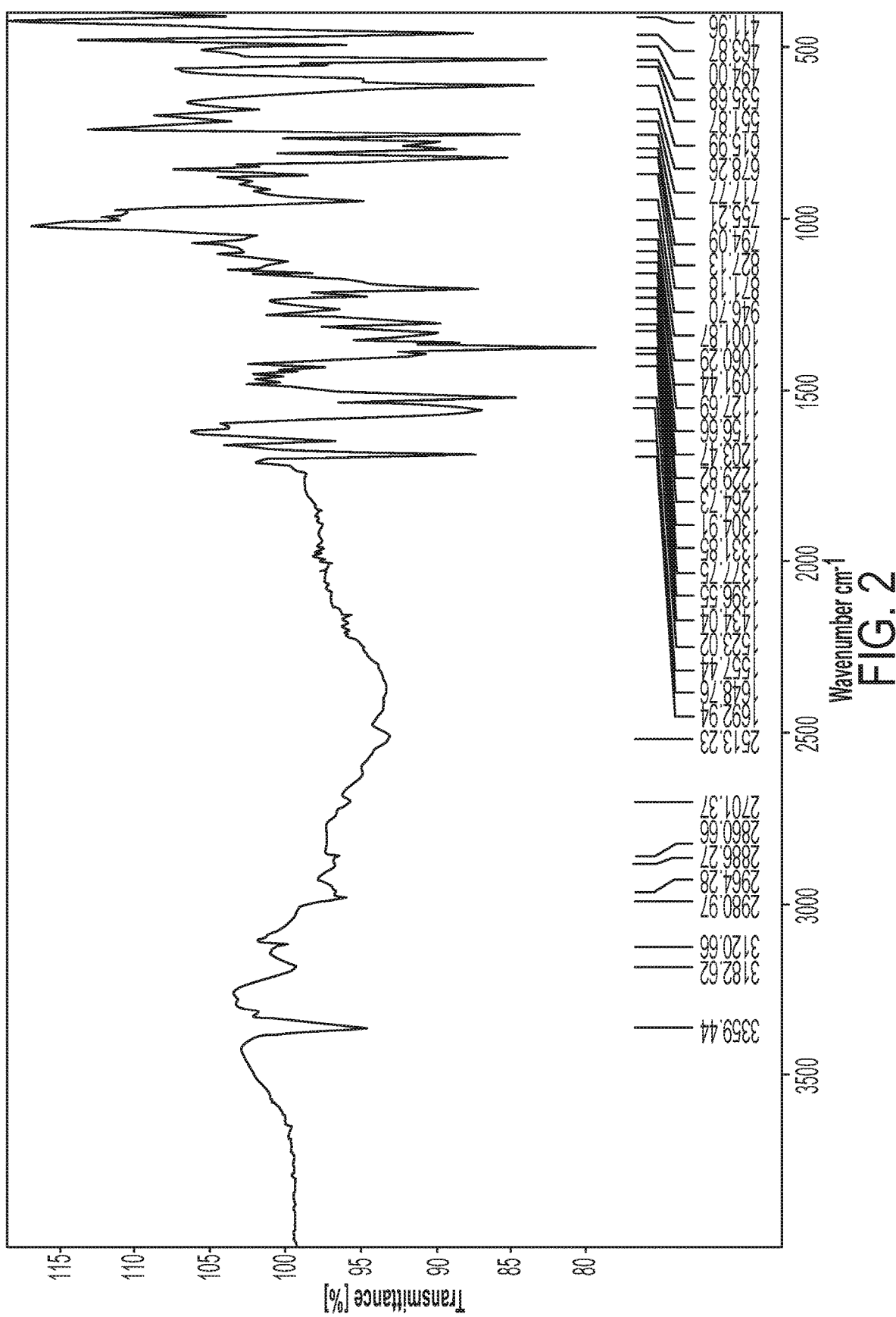
FIG. 2 shows an exemplary FT-IR spectrum for the crystalline Form 1 of the (1R,3S)-(+)-camphorate salt of 2-{4-[(3S)-piperidin-3-yl]phenyl}-2H-indazole-7-carboxamide (niraparib).

Item 29. The crystalline Form 1 of niraparib (1R,3S)-(+)-camphorate according to any one of items 5-28 characterised by an infra-red spectrum substantially as shown in FIG. 2.

Item 30. The crystalline Form 1 of niraparib (1R,3S)-(+)-camphorate according to any one of items 5-29 characterised by adsorbing no more than about 0.3% by weight of water up to about 90% relative humidity at about 25° C.

Figure 6:
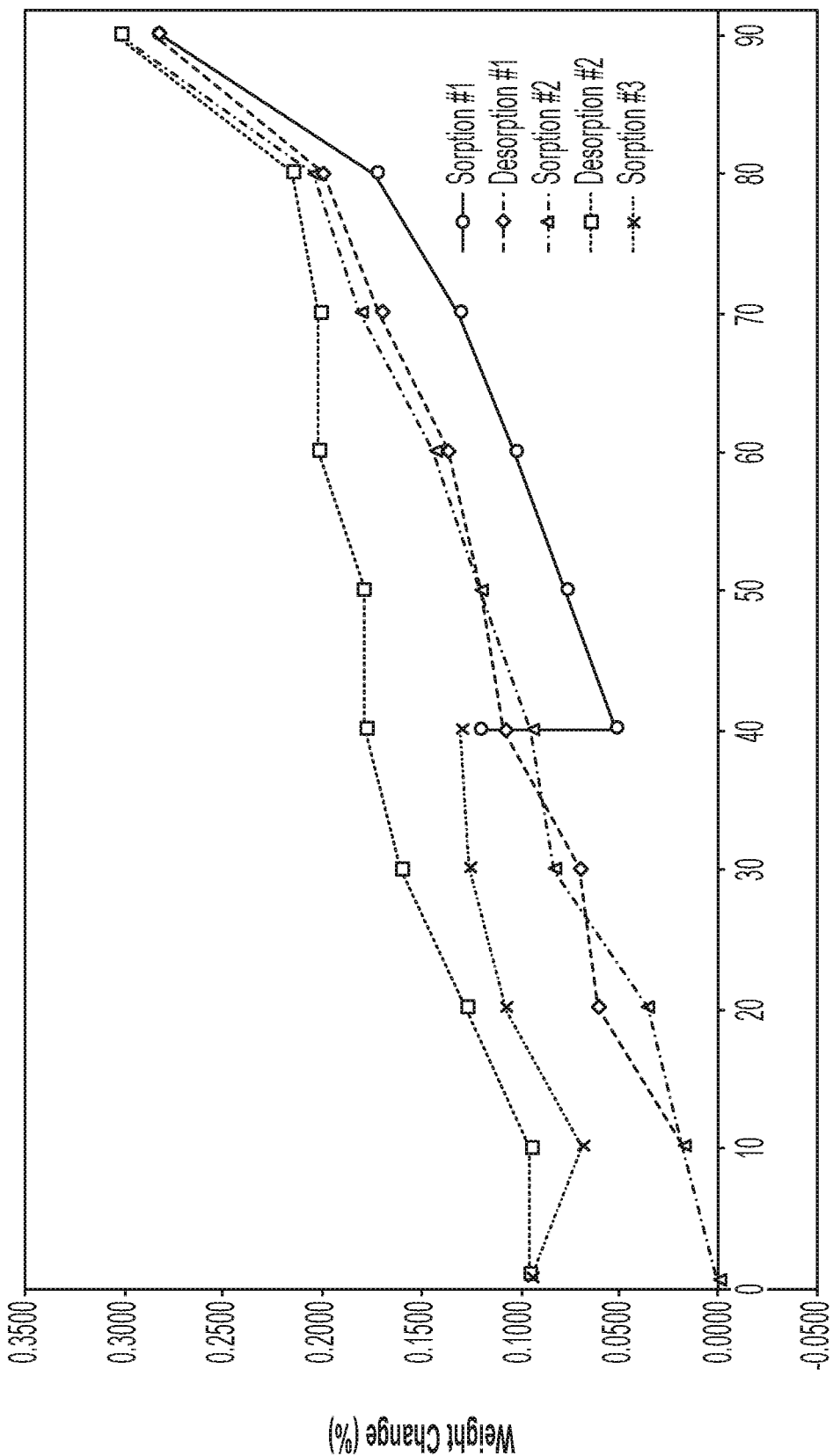
FIG. 6 shows an exemplary scanning gravimetric vapour sorption thermogram for the crystalline Form 1 of the (1R,3S)-(+)-camphorate salt of 2-{4-[(3S)-piperidin-3-yl]phenyl}-2H-indazole-7-carboxamide (niraparib).
Figure 7:
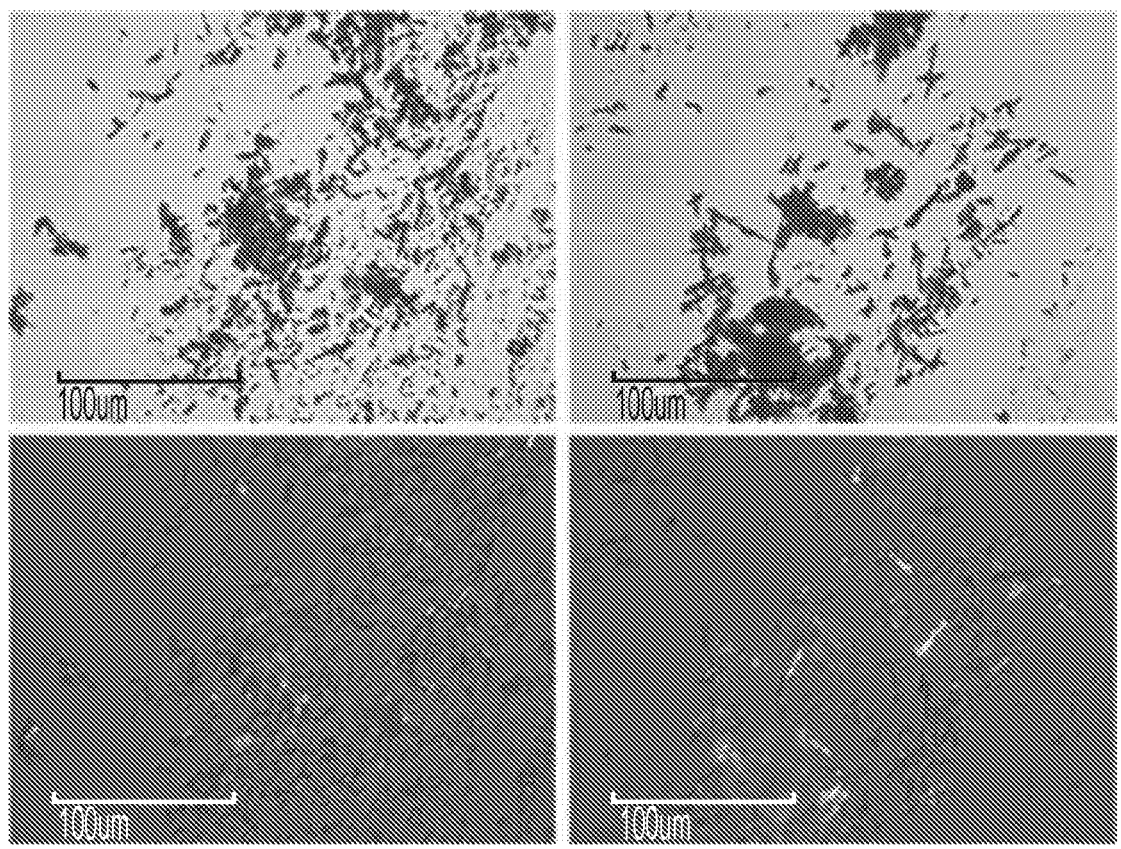
FIG. 7 shows visible light microscopic images of the crystalline Form 1 of the (1R,3S)-(+)-camphorate salt of 2-{4-[(3S)-piperidin-3-yl]phenyl}-2H-indazole-7-carboxamide (niraparib) (top: non-polarised; bottom: polarised).

Item 31. The crystalline Form 1 of niraparib (1R,3S)-(+)-camphorate according to any one of items 5-30 characterised by a GVS thermogram substantially as shown in FIG. 6.

Item 32. 2-{4-[(3S)-piperidin-3-yl]phenyl}-2H-indazole-7-carboxamide (niraparib) (1S,3R)-(−)-camphorate.

Item 33. Crystalline 2-{4-[(3S)-piperidin-3-yl]phenyl}-2H-indazole-7-carboxamide (niraparib) (1S,3R)-(−)-camphorate.

Item 34. A crystalline Form 1 of 2-{4-[(3S)-piperidin-3-yl]phenyl}-2H-indazole-7-carboxamide (niraparib) (1S,3R)-(−)-camphorate.

Item 35. The crystalline Form 1 of niraparib (1S,3R)-(−)-camphorate according to item 34, having an XRPD pattern comprising one or more peaks at 20.3, 17.4, 16.2, 15.1 and/or 20.2±0.2° 2θ.

Item 36. The crystalline Form 1 of niraparib (1S,3R)-(−)-camphorate according to item 34 or item 35, having an XRPD pattern comprising at least two peaks at 20.3, 17.4, 16.2, 15.1 and/or 20.2±0.2° 2θ.

Item 37. The crystalline Form 1 of niraparib (1S,3R)-(−)-camphorate according to any one of items 34-36, having an XRPD pattern comprising at least three peaks at 20.3, 17.4, 16.2, 15.1 and/or 20.2±0.2° 2θ.

Item 38. The crystalline Form 1 of niraparib (1S,3R)-(−)-camphorate according to any one of items 34-37, having an XRPD pattern comprising at least four peaks at 20.3, 17.4, 16.2, 15.1 and/or 20.2±0.2° 2θ.

Item 39. The crystalline Form 1 of niraparib (1S,3R)-(−)-camphorate according to any one of items 34-38, having an XRPD pattern comprising peaks at 20.3, 17.4, 16.2, 15.1 and 20.2±0.2° 2θ.

Item 40. The crystalline Form 1 of niraparib (1S,3R)-(−)-camphorate according to any one of items 34-39, having an XRPD pattern comprising one or more peaks at 24.4, 19.9, 11.6, 22.3 and/or 22.2±0.2° 2θ.

Item 41. The crystalline Form 1 of niraparib (1S,3R)-(−)-camphorate according to any one of items 34-40, having an XRPD pattern comprising at least two peaks at 24.4, 19.9, 11.6, 22.3 and/or 22.2±0.2° 2θ.

Item 42. The crystalline Form 1 of niraparib (1S,3R)-(−)-camphorate according to any one of items 34-41, having an XRPD pattern comprising at least three peaks at 24.4, 19.9, 11.6, 22.3 and/or 22.2±0.2° 2θ.

Item 43. The crystalline Form 1 of niraparib (1S,3R)-(−)-camphorate according to any one of items 34-42, having an XRPD pattern comprising at least four peaks at 24.4, 19.9, 11.6, 22.3 and/or 22.2±0.2° 2θ.

Item 44. The crystalline Form 1 of niraparib (1S,3R)-(−)-camphorate according to any one of items 34-43, having an XRPD pattern comprising peaks at 24.4, 19.9, 11.6, 22.3 and 22.2±0.2° 2θ.

Item 45. The crystalline Form 1 of niraparib (1S,3R)-(−)-camphorate according to any one of items 34-44, having an XRPD pattern comprising peaks at 20.3, 17.4, 16.2, 15.1, 20.2, 24.4, 19.9, 11.6, 22.3 and 22.2±0.2° 2θ.

Item 46. The crystalline Form 1 of niraparib (1S,3R)-(−)-camphorate according to any one of items 34-45, having an XRPD pattern comprising a peak at 16.0±0.2° 2θ.

Item 47. The crystalline Form 1 of niraparib (1S,3R)-(−)-camphorate according to any one of items 34-46, having an XRPD pattern comprising a peak at 21.9±0.2° 2θ.

Item 48. The crystalline Form 1 of niraparib (1S,3R)-(−)-camphorate according to any one of items 34-47, having an XRPD pattern comprising peaks at 16.0 and 21.9±0.2° 2θ.

Item 49. The crystalline Form 1 of niraparib (1S,3R)-(−)-camphorate according to any one of items 34-48, having an XRPD pattern comprising at least one peak at 20.3, 17.4, 16.2, 15.1, 20.2, 24.4, 19.9, 11.6, 22.3, 22.2, 13.4, 16.0, 26.9, 6.5, 23.9, 18.9, 14.5, 14.0, 21.9 and/or 21.5±0.2° 2θ.

Item 50. The crystalline Form 1 of niraparib (1S,3R)-(−)-camphorate according to any one of items 34-49, having an XRPD pattern comprising peaks with the 2θ values (±0.2° 2θ), and optionally also relative intensities, according to the following table:

| Pos. [°2θ] | Rel. Int. [%] |
|---|---|
| 6.5 | 16.7 |
| 11.6 | 22.6 |
| 13.4 | 19.2 |
| 14.0 | 11.2 |
| 14.5 | 12.8 |
| 15.1 | 48.2 |
| 16.0 | 17.4 |
| 16.2 | 48.7 |
| 17.4 | 61.0 |
| 18.9 | 15.3 |
| 19.9 | 29.8 |
| 20.2 | 34.9 |
| 20.3 | 100 |
| 21.5 | 10.9 |
| 21.9 | 11.0 |
| 22.2 | 19.8 |
| 22.3 | 20.3 |
| 23.9 | 15.9 |
| 24.4 | 31.3 |
| 26.9 | 17.0 |

Item 51. The crystalline Form 1 of niraparib (1S,3R)-(−)-camphorate according to any one of items 34-50, characterised by an XRPD pattern substantially as shown in FIG. 9.

Item 52. The crystalline Form 1 of niraparib (1S,3R)-(−)-camphorate according to any one of items 34-51, characterised by a melting point of about 220° C. to about 230° C.

Item 53. The crystalline Form 1 of niraparib (1S,3R)-(−)-camphorate according to any one of items 34-52, characterised by a melting point of about 226° C.

Item 54. The crystalline Form 1 of niraparib (1S,3R)-(−)-camphorate according to any one of items 34-53, characterised by a DSC thermogram in which the onset of melting (endothermic peak) is about 226° C. and/or wherein the peak minimum is about 230° C.

Figure 11:
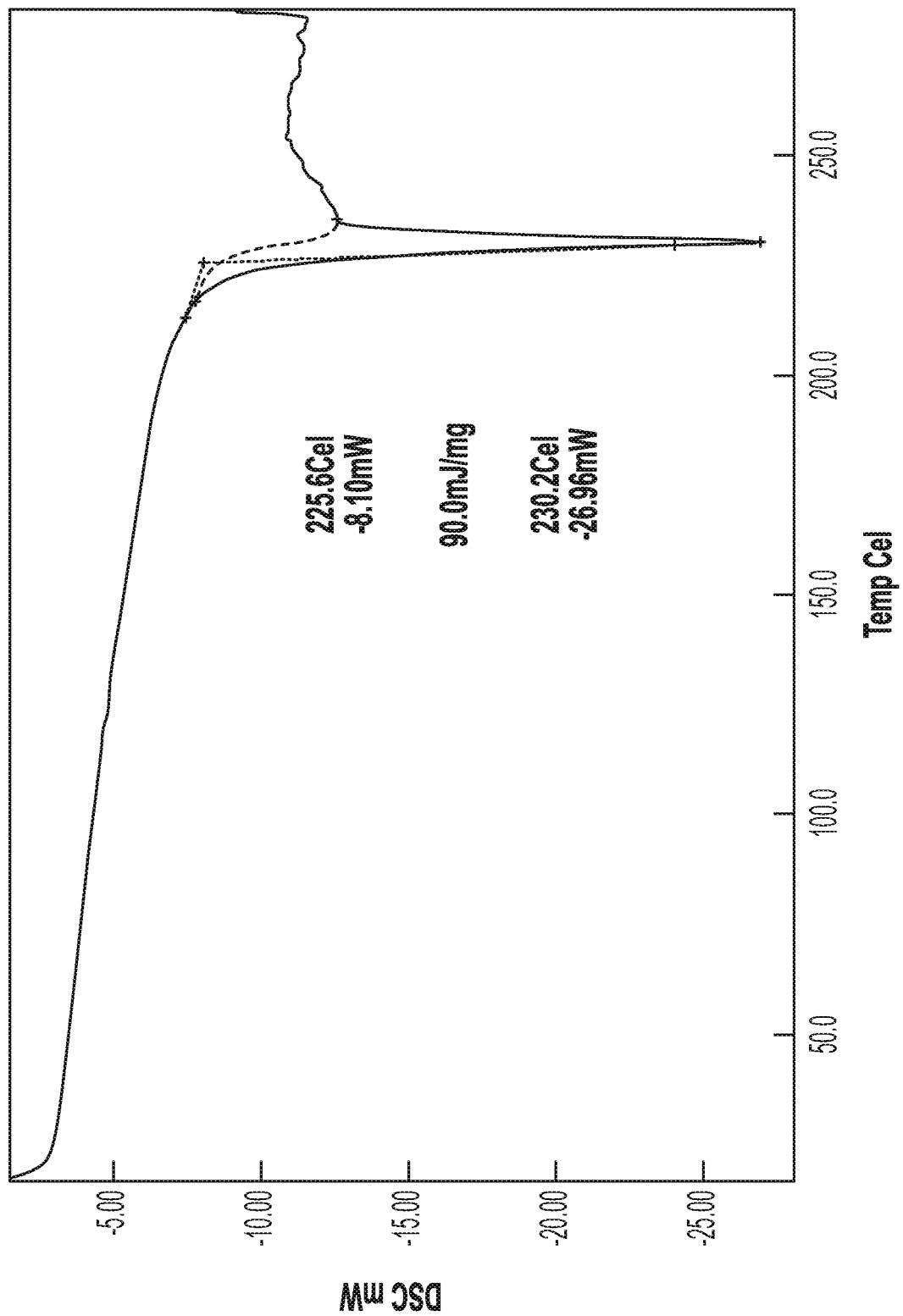
FIG. 11 shows an exemplary differential scanning calorimetry thermogram for the crystalline Form 1 of the (1S, 3R)-(−)-camphorate salt of 2-{4-[(3S)-piperidin-3-yl]phenyl}-2H-indazole-7-carboxamide (niraparib).

Item 55. The crystalline Form 1 of niraparib (1S,3R)-(−)-camphorate according to any one of items 34-54, characterised by a DSC thermogram substantially as shown in FIG. 11.

Item 56. The crystalline Form 1 of niraparib (1S,3R)-(−)-camphorate according to any one of items 34-55, characterised by an infra-red spectrum comprising peaks at about 3367 cm$^{-1}$, about 1693 cm$^{-1}$ and about 1648 cm$^{-1}$.

Figure 8:
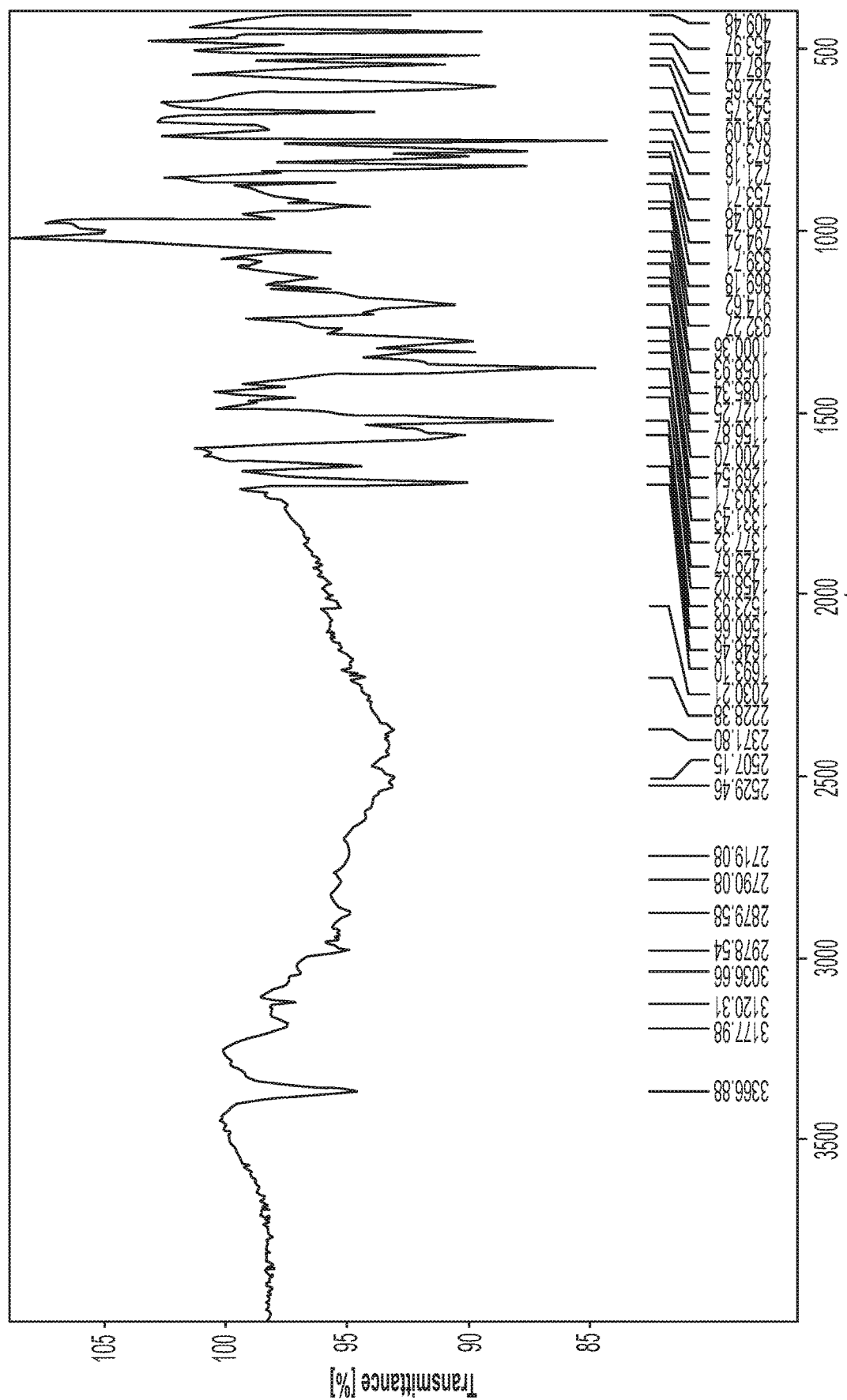
FIG. 8 shows an exemplary FT-IR spectrum for the crystalline Form 1 of the (1S,3R)-(−)-camphorate salt of 2-{4-[(3S)-piperidin-3-yl]phenyl}-2H-indazole-7-carboxamide (niraparib).

Item 57. The crystalline Form 1 of niraparib (1S,3R)-(−)-camphorate according to any one of items 34-56, characterised by an infra-red spectrum substantially as shown in FIG. 8.

Item 58. The crystalline Form 1 of niraparib (1S,3R)-(−)-camphorate according to any one of items 34-57, characterised by adsorbing less than about 1% by weight of water up to about 90% relative humidity at about 25° C.

Figure 12:
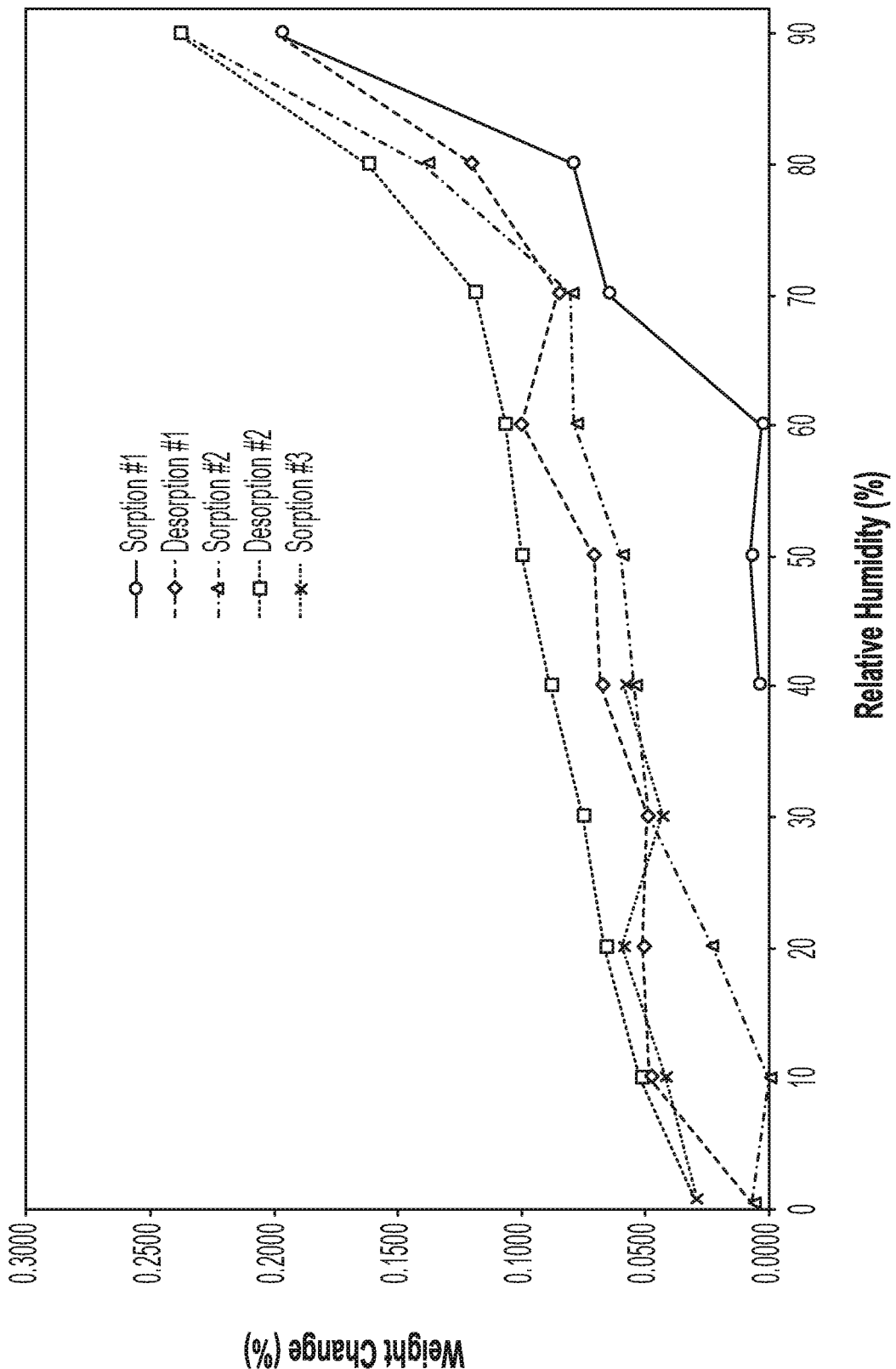
FIG. 12 shows an exemplary scanning gravimetric vapour sorption thermogram for the crystalline Form 1 of the (1S,3R)-(−)-camphorate salt of 2-{4-[(3S)-piperidin-3-yl]phenyl}-2H-indazole-7-carboxamide (niraparib).
Figure 13:
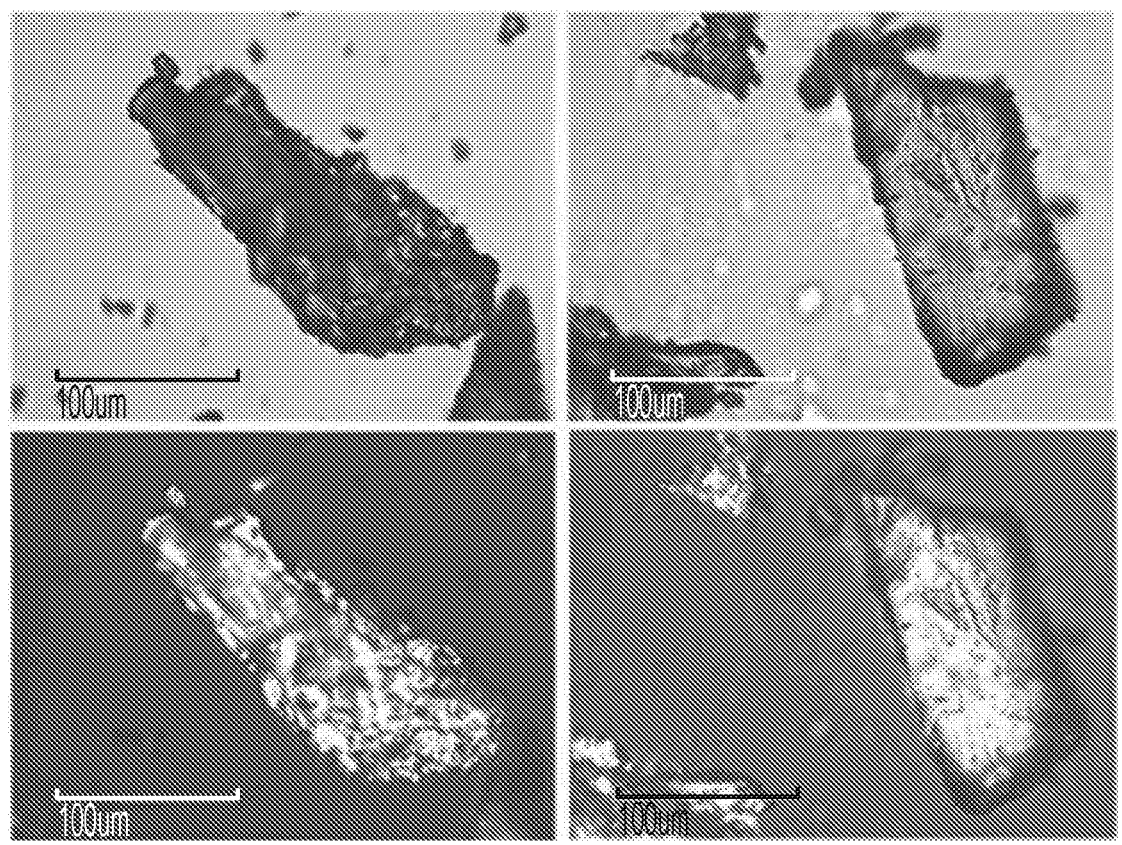
FIG. 13 shows visible light microscopic images of the crystalline Form 1 of the (1S,3R)-(−)-camphorate salt of 2-{4-[(3S)-piperidin-3-yl]phenyl}-2H-indazole-7-carboxamide (niraparib) (top: non-polarised; bottom: polarised).

Item 59. The crystalline Form 1 of niraparib (1S,3R)-(−)-camphorate according to any one of items 34-58, characterised by the GVS thermogram substantially as shown in FIG. 12.

Item 60. 2-{4-[(3S)-piperidin-3-yl]phenyl}-2H-indazole-7-carboxamide (niraparib) mandelate.

Item 61. 2-{4-[(3S)-piperidin-3-yl]phenyl}-2H-indazole-7-carboxamide (niraparib) (R)-(−)-mandelate.

Item 62. Crystalline 2-{4-[(3S)-piperidin-3-yl]phenyl}-2H-indazole-7-carboxamide (niraparib) (R)-(−)-mandelate.

Item 63. A crystalline Form 1 of 2-{4-[(3S)-piperidin-3-yl]phenyl}-2H-indazole-7-carboxamide (niraparib) (R)-(−)-mandelate.

Item 64. The crystalline Form 1 of niraparib (R)-(−)-mandelate according to item 63, having an XRPD pattern comprising one or more peaks at 18.5, 16.4, 17.4, 8.6 and/or 17.6±0.2° 2θ.

Item 65. The crystalline Form 1 of niraparib (R)-(−)-mandelate according to item 63 or item 64, having an XRPD pattern comprising at least two peaks at 18.5, 16.4, 17.4, 8.6 and/or 17.6±0.2° 2θ.

Item 66. The crystalline Form 1 of niraparib (R)-(−)-mandelate according to any one of items 63-65, having an XRPD pattern comprising at least three peaks at 18.5, 16.4, 17.4, 8.6 and/or 17.6±0.2° 2θ.

Item 67. The crystalline Form 1 of niraparib (R)-(−)-mandelate according to any one of items 63-66, having an XRPD pattern comprising at least four peaks at 18.5, 16.4, 17.4, 8.6 and/or 17.6±0.2° 2θ.

Item 68. The crystalline Form 1 of niraparib (R)-(−)-mandelate according to any one of items 63-67, having an XRPD pattern comprising peaks at 18.5, 16.4, 17.4, 8.6 and 17.6±0.2° 2θ.

Item 69. The crystalline Form 1 of niraparib (R)-(−)-mandelate according to any one of items 63-68, having an XRPD pattern comprising one or more peaks at 8.7, 18.4, 25.1, 27.6 and/or 13.7±0.2° 2θ.

Item 70. The crystalline Form 1 of niraparib (R)-(−)-mandelate according to any one of items 63-69, having an XRPD pattern comprising two or more peaks at 8.7, 18.4, 25.1, 27.6 and/or 13.7±0.2° 2θ.

Item 71. The crystalline Form 1 of niraparib (R)-(−)-mandelate according to any one of items 63-70, having an XRPD pattern comprising three or more peaks at 8.7, 18.4, 25.1, 27.6 and/or 13.7±0.2° 2θ.

Item 72. The crystalline Form 1 of niraparib (R)-(−)-mandelate according to any one of items 63-71, having an XRPD pattern comprising four or more peaks at 8.7, 18.4, 25.1, 27.6 and/or 13.7±0.2° 2θ.

Item 73. The crystalline Form 1 of niraparib (R)-(−)-mandelate according to any one of items 63-72, having an XRPD pattern comprising peaks at 8.7, 18.4, 25.1, 27.6 and 13.7±0.2° 2θ.

Item 74. The crystalline Form 1 of niraparib (R)-(−)-mandelate according to any one of items 63-73, having an XRPD pattern comprising peaks at 18.5, 16.4, 17.4, 8.6, 17.6, 8.7, 18.4, 25.1, 27.6 and 13.7±0.2° 2θ.

Item 75. The crystalline Form 1 of niraparib (R)-(−)-mandelate according to any one of items 63-74, having an XRPD pattern comprising one or more peaks at 18.5, 16.4, 17.4, 8.6, 17.6, 8.7, 18.4, 25.1, 27.6, 13.7, 8.4, 28.7, 28.0, 4.3, 21.5, 27.3, 14.1, 27.7, 12.4 and/or 16.1±0.2° 2θ.

Item 76. The crystalline Form 1 of niraparib (R)-(−)-mandelate according to any one of items 63-75, having an XRPD pattern comprising peaks with the 2θ values (±0.2° 2θ), and optionally also relative intensities, according to the following table:

| Pos. [°2θ] | Rel. Int. [%] |
|---|---|
| 4.3 | 22.3 |
| 8.4 | 27.0 |
| 8.6 | 57.9 |
| 8.7 | 48.3 |
| 12.4 | 17.4 |
| 13.7 | 31.9 |
| 14.1 | 19.9 |
| 16.1 | 17.0 |
| 16.4 | 99.2 |
| 17.4 | 75.9 |
| 17.6 | 52.5 |
| 18.4 | 44.4 |
| 18.5 | 100 |
| 21.5 | 22.2 |
| 25.1 | 39.0 |
| 27.3 | 20.3 |
| 27.6 | 35.9 |
| 27.7 | 19.0 |
| 28.0 | 22.5 |
| 28.7 | 24.8 |

Item 77. The crystalline Form 1 of niraparib (R)-(−)-mandelate according to any one of items 63-76, characterised by an XRPD pattern substantially as shown in FIG. 15.

Item 78. The crystalline Form 1 of niraparib (R)-(−)-mandelate according to any one of items 63-77, characterised by a melting point of about 190° C. to about 200° C.

Item 79. The crystalline Form 1 of niraparib (R)-(−)-mandelate according to any one of items 63-78, characterised by a melting point of about 197° C.

Item 80. The crystalline Form 1 of niraparib (R)-(−)-mandelate according to any one of items 63-79, characterised by a DSC thermogram in which the onset of melting (endothermic peak) is about 197° C. and/or wherein the peak minimum is about 201° C.

Item 81. The crystalline Form 1 of niraparib (R)-(−)-mandelate according to any one of items 63-80, characterised by a DSC thermogram substantially as shown in FIG. 18.

Item 82. The crystalline Form 1 of niraparib (R)-(−)-mandelate according to any one of items 63-81, characterised by an infra-red spectrum comprising peaks at about 3443 cm$^{-1}$, about 3340 cm$^{-1}$, about 1671 cm$^{-1}$ and about 1638 cm$^{-1}$.

Figure 14:
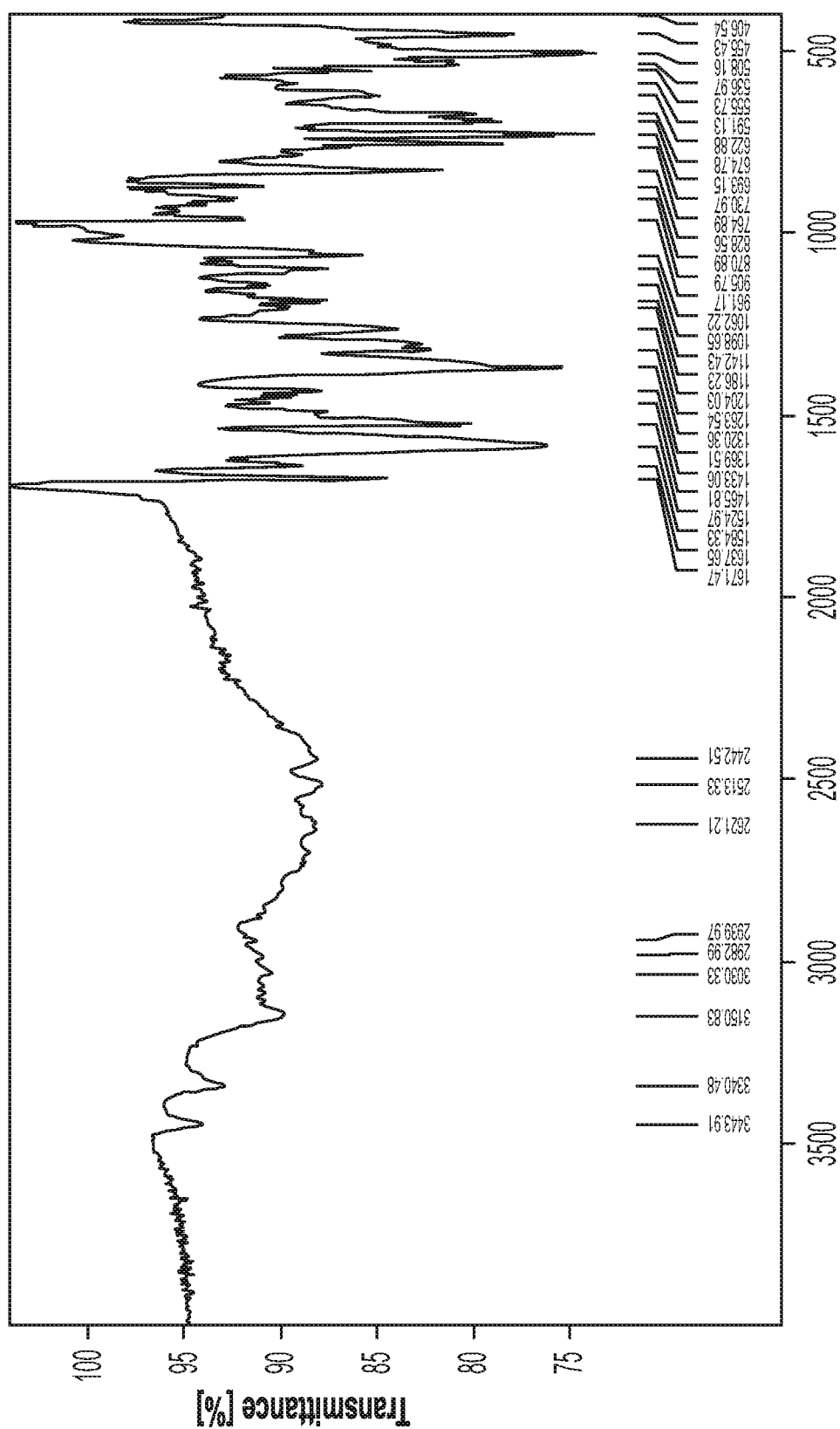
FIG. 14 shows an exemplary FT-IR spectrum for the crystalline Form 1 of the (R)-(−)-mandelate salt of 2-{4-[(3S)-piperidin-3-yl]phenyl}-2H-indazole-7-carboxamide (niraparib).

Item 83. The crystalline Form 1 of niraparib (R)-(−)-mandelate according to any one of items 63-82, characterised by an infra-red spectrum substantially as shown in FIG. 14.

Figure 19:
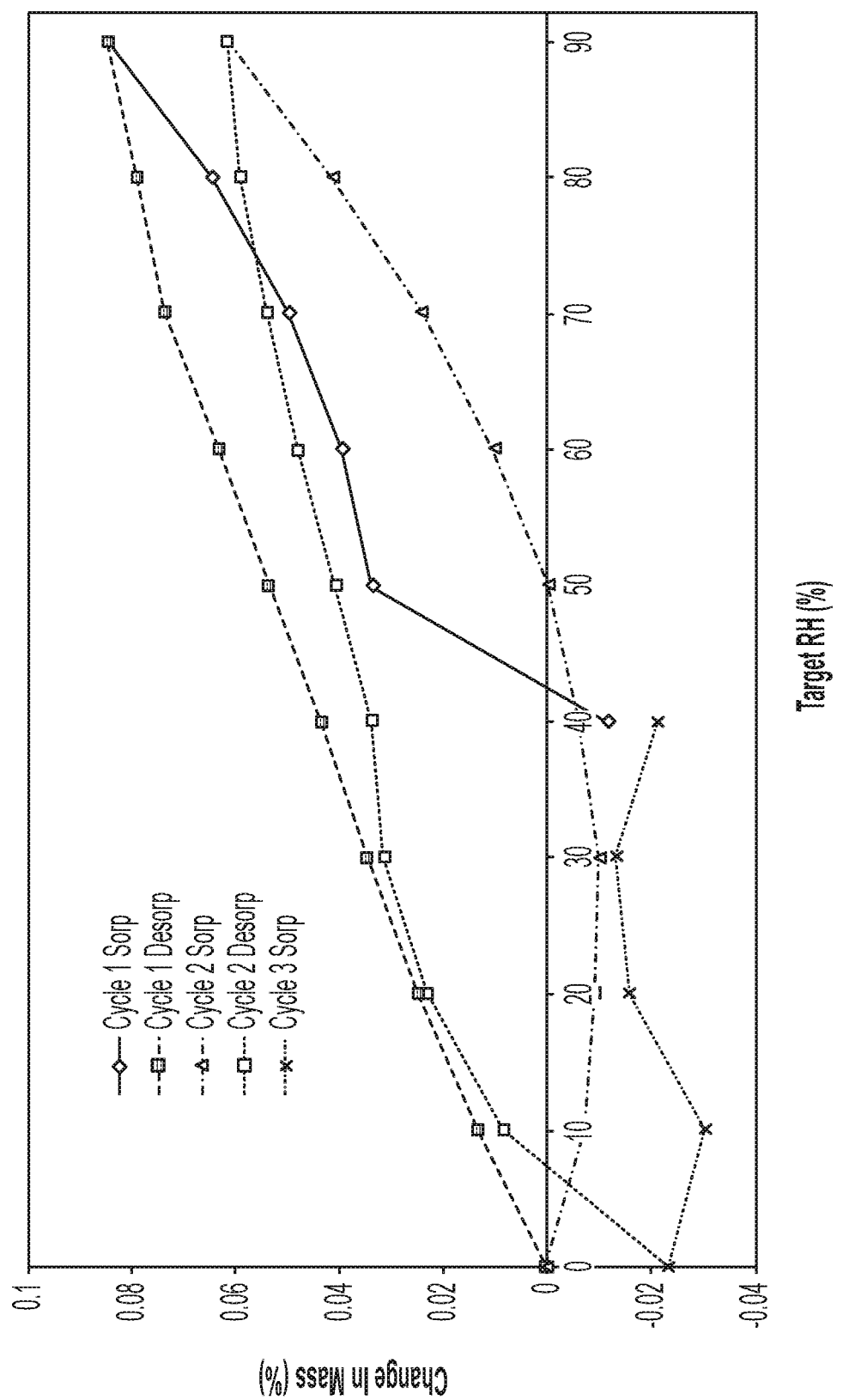
FIG. 19 shows an exemplary dynamic vapour sorption thermogram for the crystalline Form 1 of the (R)-(−)-mandelate salt of 2-{4-[(3S)-piperidin-3-yl]phenyl}-2H-indazole-7-carboxamide (niraparib).
Figure 20:
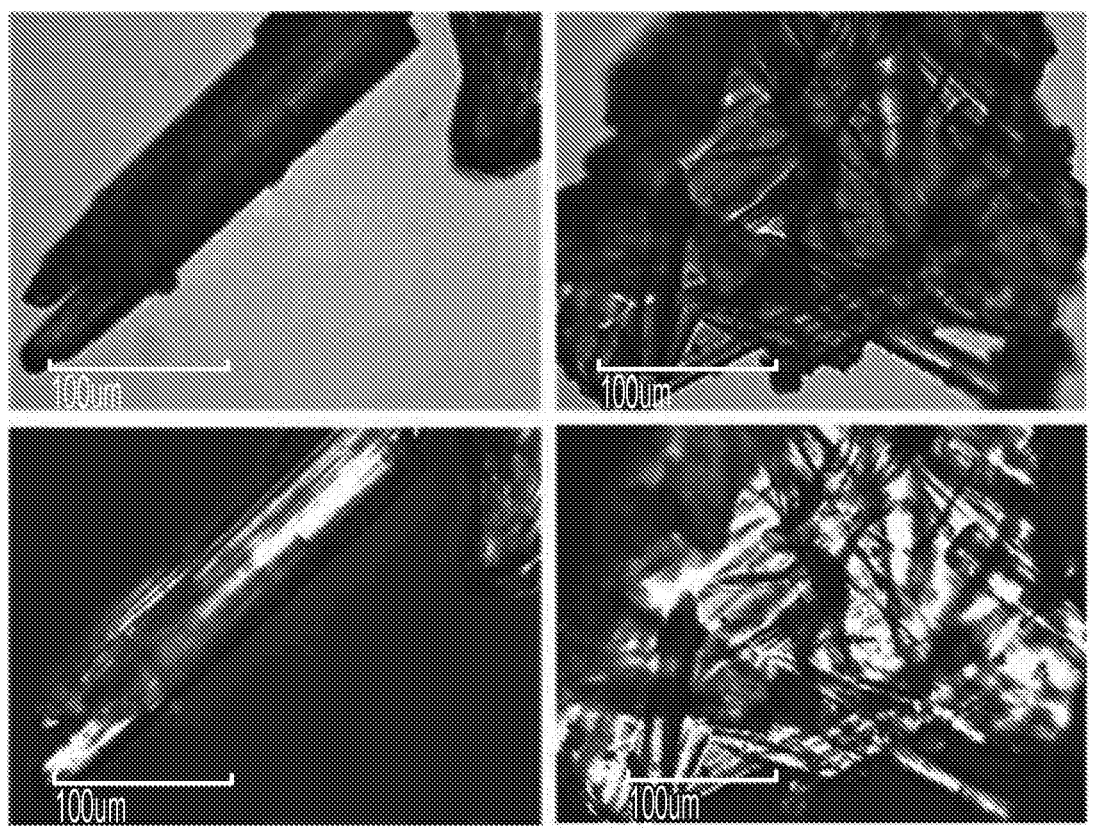
FIG. 20 shows visible light microscopic images of the crystalline Form 1 of the (R)-(−)-mandelate salt of 2-{4-[(3S)-piperidin-3-yl]phenyl}-2H-indazole-7-carboxamide (niraparib) (top: non-polarised; bottom: polarised).

Item 84. The crystalline Form 1 of niraparib (R)-(−)-mandelate according to any one of items 63-83, characterised by a DVS thermogram substantially as shown in FIG. 19.

Item 85. 2-{4-[(3S)-piperidin-3-yl]phenyl}-2H-indazole-7-carboxamide (niraparib) camsylate.

Item 86. 2-{4-[(3S)-piperidin-3-yl]phenyl}-2H-indazole-7-carboxamide (niraparib) (1S)-(+)-camsylate.

Item 87. Crystalline 2-{4-[(3S)-piperidin-3-yl]phenyl}-2H-indazole-7-carboxamide (niraparib) (1S)-(+)-camsylate.

Item 88. A crystalline Form 1 of 2-{4-[(3S)-piperidin-3-yl]phenyl}-2H-indazole-7-carboxamide (niraparib) (1S)-(+)-camsylate.

Item 89. The crystalline Form 1 of niraparib (1S)-(+)-camsylate according to item 88, having an XRPD pattern comprising one or more peaks at 16.0, 13.5, 17.6, 24.3 and/or 24.6±0.2° 2θ.

Item 90. The crystalline Form 1 of niraparib (1S)-(+)-camsylate according to item 88 or item 89, having an XRPD pattern comprising at least two peaks at 16.0, 13.5, 17.6, 24.3 and/or 24.6±0.2° 2θ.

Item 91. The crystalline Form 1 of niraparib (1S)-(+)-camsylate according to any one of items 88-90, having an XRPD pattern comprising at least three peaks at 16.0, 13.5, 17.6, 24.3 and/or 24.6±0.2° 2θ.

Item 92. The crystalline Form 1 of niraparib (1S)-(+)-camsylate according to any one of items 88-91, having an XRPD pattern comprising at least four peaks at 16.0, 13.5, 17.6, 24.3 and/or 24.6±0.2° 2θ.

Item 93. The crystalline Form 1 of niraparib (1S)-(+)-camsylate according to any one of items 88-92, having an XRPD pattern comprising peaks at 16.0, 13.5, 17.6, 24.3 and 24.6±0.2° 2θ.

Item 94. The crystalline Form 1 of niraparib (1S)-(+)-camsylate according to any one of items 88-93, having an XRPD pattern comprising one or more peaks at 11.1, 16.4, 23.7, 16.7 and/or 20.3±0.2° 2θ.

Item 95. The crystalline Form 1 of niraparib (1S)-(+)-camsylate according to any one of items 88-94, having an XRPD pattern comprising two or more XRPD peaks at 11.1, 16.4, 23.7, 16.7 and/or 20.3±0.2° 2θ.

Item 96. The crystalline Form 1 of niraparib (1S)-(+)-camsylate according to any one of items 88-95, having an XRPD pattern comprising three or more peaks at 11.1, 16.4, 23.7, 16.7 and/or 20.3±0.2° 2θ.

Item 97. The crystalline Form 1 of niraparib (1S)-(+)-camsylate according to any one of items 88-96, having an XRPD pattern comprising four or more peaks at 11.1, 16.4, 23.7, 16.7 and/or 20.3±0.2° 2θ.

Item 98. The crystalline Form 1 of niraparib (1S)-(+)-camsylate according to any one of items 88-97, having an XRPD pattern comprising peaks at 11.1, 16.4, 23.7, 16.7 and 20.3±0.2° 2θ.

Item 99. The crystalline Form 1 of niraparib (1S)-(+)-camsylate according to any one of items 88-98, having an XRPD pattern comprising peaks at 16.0, 13.5, 17.6, 24.3, 24.6, 11.1, 16.4, 23.7, 16.7 and 20.3±0.2° 2θ.

Item 100. The crystalline Form 1 of niraparib (1S)-(+)-camsylate according to any one of items 88-99, having an XRPD pattern comprising one or more peaks at 6.7, 16.4, 23.7 and/or 25.2±0.2° 2θ.

Item 101. The crystalline Form 1 of niraparib (1S)-(+)-camsylate according to any one of items 88-100, having an XRPD pattern comprising at least two peaks at 6.7, 16.4, 23.7 and/or 25.2±0.2° 2θ.

Item 102. The crystalline Form 1 of niraparib (1S)-(+)-camsylate according to any one of items 88-101, having an XRPD pattern comprising at least three peaks at 6.7, 16.4, 23.7 and/or 25.2±0.2° 2θ.

Item 103. The crystalline Form 1 of niraparib (1S)-(+)-camsylate according to any one of items 88-102, having an XRPD pattern comprising peaks at 6.7, 16.4, 23.7 and 25.2±0.2° 2θ.

Item 104. The crystalline Form 1 of niraparib (1S)-(+)-camsylate according to any one of items 88-103, having an XRPD pattern comprising at least one peak at 16.0, 13.5, 17.6, 24.3, 24.6, 11.1, 16.4, 23.7, 16.7, 20.3, 6.7, 25.2, 25.0, 25.8, 26.8, 22.8, 9.5, 16.9, 14.3 and/or 7.7±0.2° 2θ.

Item 105. The crystalline Form 1 of niraparib (1S)-(+)-camsylate according to any one of items 88-104, having an XRPD pattern comprising peaks with the 2θ values (±0.2° 2θ), and optionally also relative intensities, according to the following table:

| Pos. [°2θ] | Rel. Int. [%] |
|---|---|
| 6.7 | 13.8 |
| 7.7 | 8.9 |
| 9.5 | 10.4 |
| 11.1 | 22.2 |
| 13.5 | 58.6 |
| 14.3 | 9.1 |
| 16.0 | 100 |
| 16.4 | 20.4 |
| 16.7 | 19.1 |
| 16.9 | 9.8 |
| 17.6 | 55.4 |
| 20.3 | 14.5 |
| 22.8 | 11.6 |
| 23.7 | 19.6 |
| 24.3 | 47.4 |
| 24.6 | 45.9 |
| 25.0 | 12.9 |
| 25.2 | 13.4 |
| 25.8 | 12.0 |
| 26.8 | 11.6 |

Item 106. The crystalline Form 1 of niraparib (1S)-(+)-camsylate according to any one of items 88-105, characterised by an XRPD pattern substantially as shown in FIG. 22.

Item 107. The crystalline Form 1 of niraparib (1S)-(+)-camsylate according to any one of items 88-106, characterised by a melting point of about 235° C. to about 245° C.

Item 108. The crystalline Form 1 of niraparib (1S)-(+)-camsylate according to any one of items 88-107, characterised by a melting point of about 239° C.

Item 109. The crystalline Form 1 of niraparib (1S)-(+)-camsylate according to any one of items 88-108, characterised by a DSC thermogram in which the onset of melting (endothermic peak) is about 235° C. and/or wherein the peak minimum is about 246° C.

Figure 24:
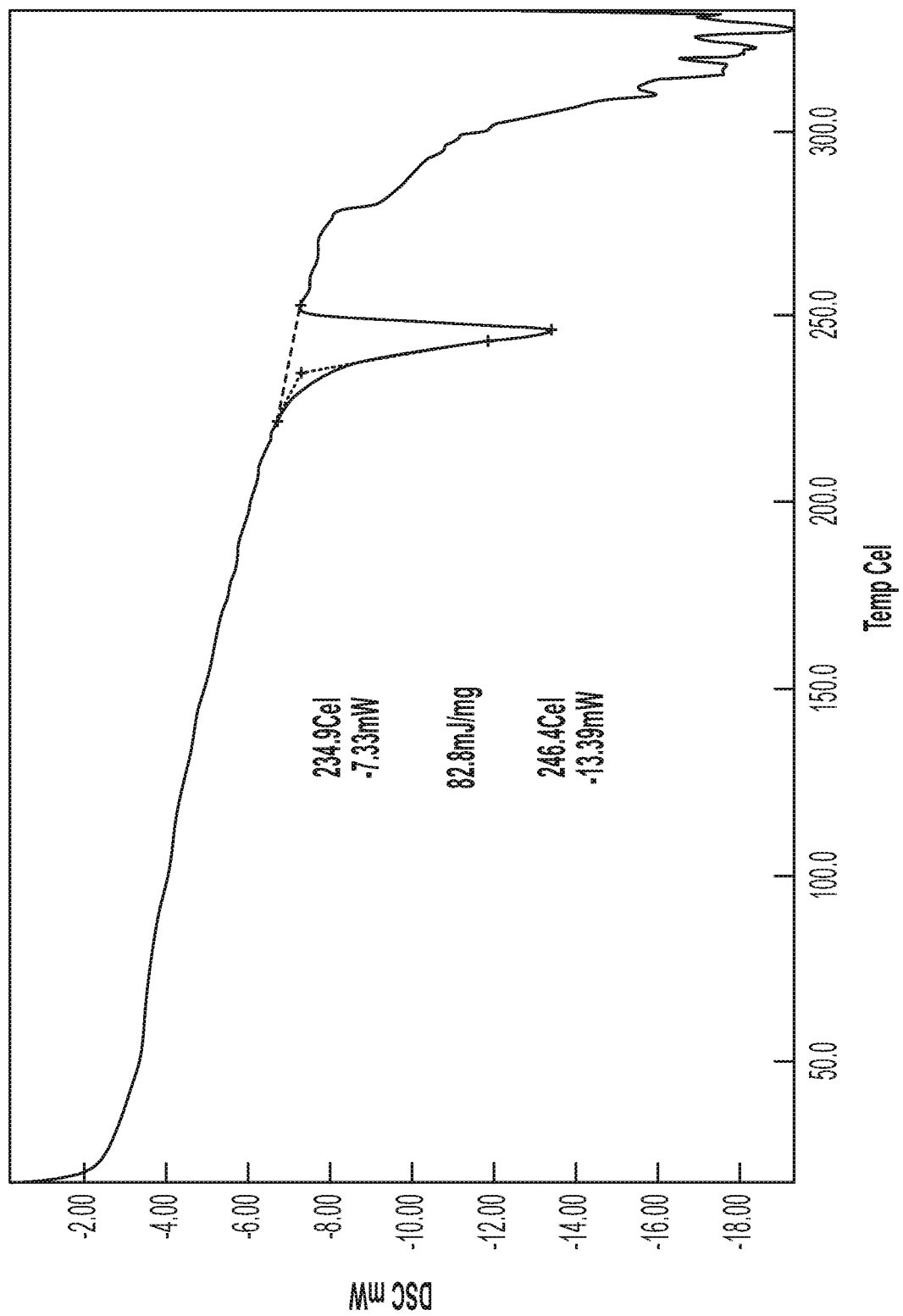
FIG. 24 shows an exemplary differential scanning calorimetry thermogram for the crystalline Form 1 of the (1S)-(+)-camsylate salt of 2-{4-[(3S)-piperidin-3-yl]phenyl}-2H-indazole-7-carboxamide (niraparib).

Item 110. The crystalline Form 1 of niraparib (1S)-(+)-camsylate according to any one of items 88-109, characterised by a DSC thermogram substantially as shown in FIG. 24.

Item 111. The crystalline Form 1 of niraparib (1S)-(+)-camsylate according to any one of items 88-110, characterised by an infra-red spectrum comprising peaks at about 3467 cm$^{-1}$, about 3306 cm$^{-1}$, about 1724 cm$^{-1}$, about 1660 cm$^{-1}$, and about 1611 cm$^{-1}$.

Figure 21:
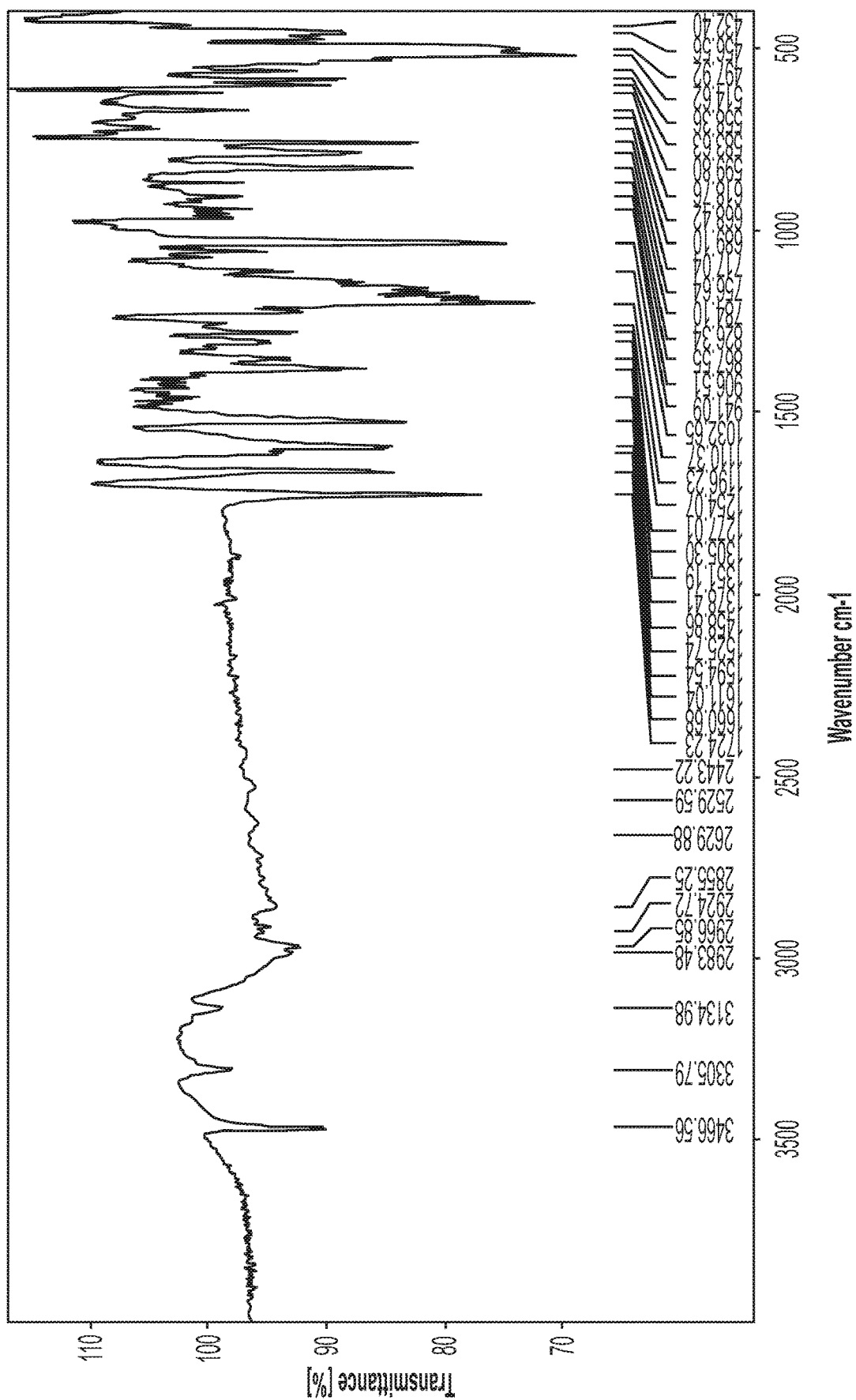
FIG. 21 shows an exemplary FT-IR spectrum for the crystalline Form 1 of the (1S)-(+)-camsylate salt of 2-{4-[(3S)-piperidin-3-yl]phenyl}-2H-indazole-7-carboxamide (niraparib).

Item 112. The crystalline Form 1 of niraparib (1S)-(+)-camsylate according to any one of items 88-112, characterised by an infra-red spectrum substantially as shown in FIG. 21.

Item 113. The crystalline Form 1 of niraparib (1S)-(+)-camsylate according to any one of items 88-112, characterised by adsorbing less than about 2% by weight of water up to about 90% relative humidity at about 25° C.

Item 114. The crystalline Form 1 of niraparib (1S)-(+)-camsylate according to any one of items 88-113, characterised by adsorbing about 1.3% by weight of water up to about 90% relative humidity at about 25° C.

Figure 25:
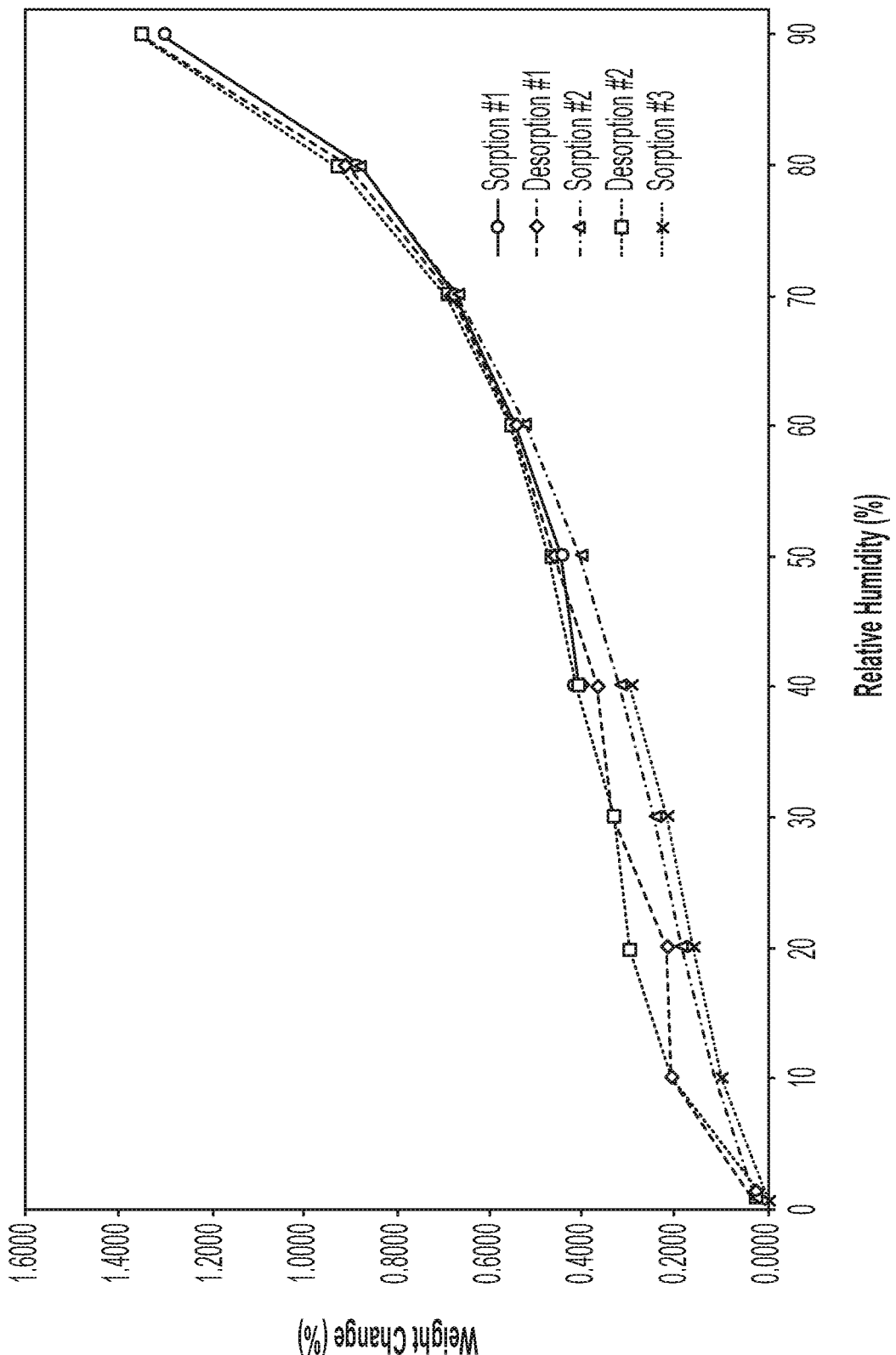
FIG. 25 shows an exemplary scanning gravimetric vapour sorption thermogram for the crystalline Form 1 of the (1S)-(+)-camsylate salt of 2-{4-[(3S)-piperidin-3-yl]phenyl}-2H-indazole-7-carboxamide (niraparib).
Figure 26:
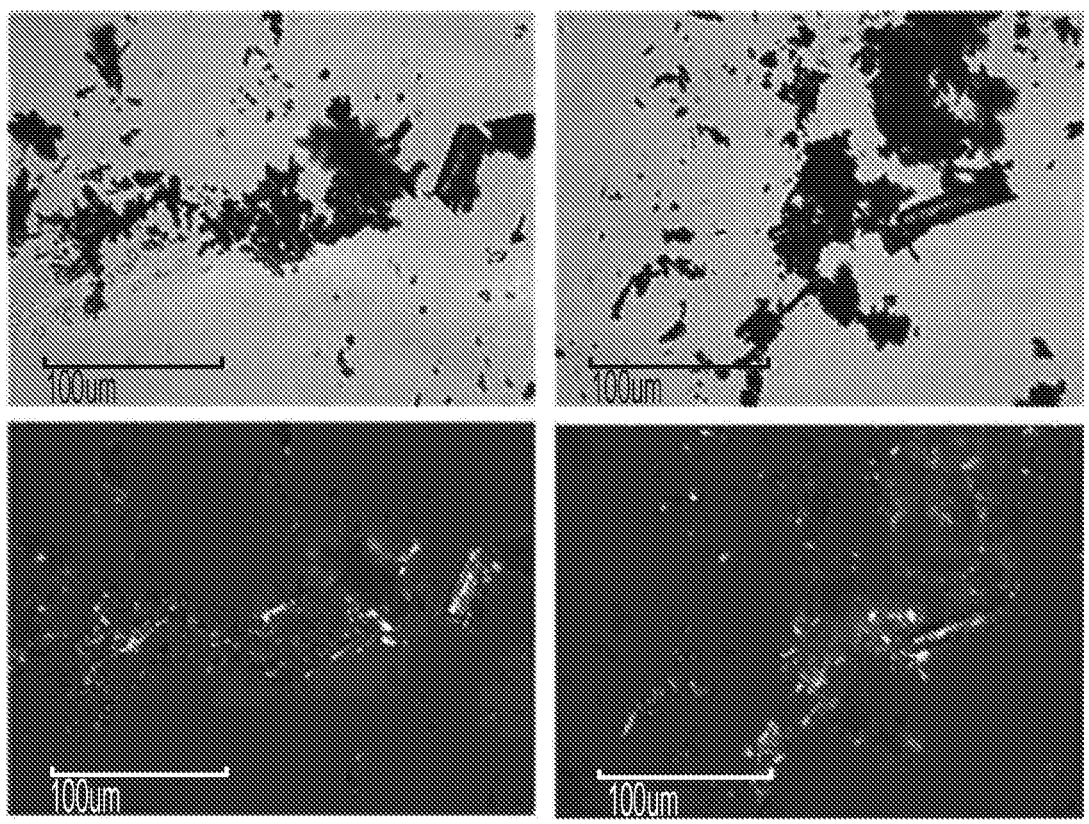
FIG. 26 shows visible light microscopic images of the crystalline Form 1 of the (1S)-(+)-camsylate salt of 2-{4-[(3S)-piperidin-3-yl]phenyl}-2H-indazole-7-carboxamide (niraparib) (top: non-polarised; bottom: polarised).

Item 115. The crystalline Form 1 of niraparib (1S)-(+)-camsylate according to any one of items 88-114, characterised by a GVS thermogram substantially as shown in FIG. 25.

Item 116. A pharmaceutical composition comprising the niraparib camphorate, niraparib mandelate or niraparib camsylate of any one of items 1 to 115, and at least one pharmaceutically acceptable excipient.

Item 117. The niraparib camphorate, niraparib mandelate or niraparib camsylate of any one of items 1 to 115, or the pharmaceutical composition of item 116, for use in therapy.

Item 118. Use of the niraparib camphorate, niraparib mandelate or niraparib camsylate of any one of items 1 to 115, or the pharmaceutical composition of item 116, in the manufacture of a medicament.

Item 119. A method of treating cancer, stroke, autoimmune diabetes, a neurological disease, an inflammatory disease, a metabolic disease or a cardiovascular disease in a subject, the method comprising administering to the subject an effective amount of the niraparib camphorate, niraparib mandelate or niraparib camsylate of any one of items 1 to 115, or the pharmaceutical composition of item 116.

Item 120. The method according to item 119, wherein said method is a method of treating cancer.

Item 121. The method according to item 120, wherein said cancer is associated with BRCA1 and/or BRCA2 mutations.

Item 122. The method according to item 120 or 121, wherein said cancer is associated with a mutation in ATM, ATR, BAP1, BARD1, BLM, BRIP1, MRE11A, NBN, PALB2, RAD51, RAD51B, RAD51C, RAD51D, RAD52, RAD54L, or XRCC2, or any combination thereof.

Item 123. The method according to any one of items 120 to 122, wherein said cancer is epithelial ovarian cancer, fallopian tube cancer, or primary peritoneal cancer.

Item 124. The niraparib camphorate, niraparib mandelate or niraparib camsylate of any one of items 1 to 115, or the pharmaceutical composition of item 116, for use in a method as defined in any one of items 119 to 123.

Item 125. Use of the niraparib camphorate, niraparib mandelate or niraparib camsylate of any one of items 1 to 115, or the pharmaceutical composition of item 116, in the manufacture of a medicament for use in a method as defined in any one of items 119 to 123.

EXAMPLES

Analytical Procedures
X-Ray Powder Diffraction (XRPD)

XRPD analysis was typically carried out on a PANalytical X'pert pro, scanning the samples between 3 and 35° 2θ. The material was gently ground to release any agglomerates and loaded onto a multi-well plate with Kapton or Mylar polymer film to support the sample. The multi-well plate was then placed into the diffractometer and analysed using Cu K radiation ($\alpha_1$ λ=1.54060 Å; $\alpha_2$=1.54443 Å; β=1.39225 Å; $\alpha_1:\alpha_2$ ratio=0.5) running in transmission mode (step size 0.0130° 2θ) using 40 kV/40 mA generator settings.

Unless otherwise stated, the XRPD analysis was carried out at room temperature and pressure and at a relative humidity of about 30-50% (e.g. about 40% relative humidity).

NMR Analysis

NMR methods were typically performed on a Bruker AVIIIHD spectrometer equipped with a DCH cryoprobe. Experiments were performed in deuterated DMSO and each sample was prepared to about 10 mM concentration. Unless otherwise stated, NMR spectra were acquired at room temperature (e.g. around 300K).

High Performance Liquid Chromatography-Ultraviolet Detection (HPLC-UV)

HPLC was typically performed using the following parameters:

| | |
|---|---|
| Column: | Waters Symmetry C18, 150 × 3.9 mm, 5 μm |
| Column Temperature: | 40° C. |
| Autosampler Temperature: | 5° C. |
| UV wavelength: | 220 nm |
| Injection Volume: | 4.3 μL |
| Flow Rate: | 1.962 mL/min |
| Mobile Phase A: | 0.1% Perchloric acid in water |
| Mobile Phase B: | Acetonitrile |

The gradient program typically used was:

| Time (minutes) | Solvent B [%] |
|---|---|
| 0 | 5 |
| 13.739 | 30 |
| 21.982 | 95 |
| 23.081 | 95 |
| 23.136 | 5 |
| 27.477 | 5 |

Polarised Light Microscopy (PLM)

The presence of crystallinity (birefringence) was typically determined using an Olympus BX50 polarising microscope, equipped with a Motic camera and image capture software (Motic Images Plus 2.0). All images were recorded using the 20× objective, unless otherwise stated.

Infrared Spectroscopy (FT-IR)

Infrared spectroscopy was typically carried out on a Bruker ALPHA P spectrometer. Sufficient material was placed onto the centre of the plate of the spectrometer and the spectra were obtained using the following parameters:

| | |
|---|---|
| Resolution: | 4 cm$^{-1}$ |
| Background Scan Time: | 16 scans |
| Sample Scan Time: | 16 scans |
| Data Collection: | 4000 to 400 cm$^{-1}$ |
| Result Spectrum: | Transmittance |
| Software: | OPUS version 6 |

Thermogravimetric Analysis (TGA)

Typically, approximately 5 mg of material was weighed into an open aluminium pan and loaded into a simultaneous thermogravimetric/differential thermal analyser (TG/DTA) and held at room temperature. The sample was then heated at a rate of 10° C./min from 20° C. to 350° C. during which time the change in sample weight was recorded along with any differential thermal events (DTA). Nitrogen was used as the purge gas, at a flow rate of 300 cm$^3$/min.

Differential Scanning Calorimetry (DSC)

Typically, approximately 5 mg of material was weighed into an aluminium DSC pan and sealed non-hermetically with a pierced aluminium lid. The sample pan was then loaded into a Seiko DSC6200 (equipped with a cooler) cooled and held at 20° C. Once a stable heat-flow response was obtained, the sample and reference were heated to melting (if possible) at a scan rate of 10° C./min and the resulting heat flow response monitored. Nitrogen was used as the purge gas, at a flow rate of 50 cm$^3$/min.

Gravimetric Vapour Sorption (GVS)

Typically, approximately 10-20 mg of sample was placed into a mesh vapour sorption balance pan and loaded into an IGASorp Moisture Sorption Analyser balance by Hiden Analytical. The sample was subjected to a ramping profile from 40-90% relative humidity (RH) at 10% increments, maintaining the sample at each step until a stable weight had been achieved (98% step completion, minimum step length 30 minutes, maximum step length 60 minutes) at 25° C. After completion of the sorption cycle, the sample was dried using the same procedure to 0% RH, and finally taken back to the starting point of 40% RH. Two cycles were performed. The weight change during the sorption/desorption cycles were plotted, allowing for the hygroscopic nature of the sample to be determined.

Dynamic Vapour Sorption (DVS)

Typically, approximately 10 mg of sample was placed into a mesh vapor sorption balance pan and loaded into a DVS-1/DVS Intrinsic/DVS Advantage dynamic vapor sorption balance by Surface Measurement Systems. The sample was subjected to a ramping profile from 40-90% relative humidity (RH) at 10% increments, maintaining the sample at each step until a stable weight had been achieved (dm/dt 0.004%, minimum step length 30 min, maximum step length 500 min) at 25° C. After completion of the sorption cycle, the sample was dried using the same procedure to 0% RH and then a second sorption cycle back to 40% RH. Two cycles were performed. The weight change during the sorption/desorption cycles were plotted, allowing for the hygroscopic nature of the sample to be determined.

Synthesis of Niraparib Tosylate Salt and Niraparib Freebase

Niraparib Tosylate Monohydrate

Niraparib tosylate monohydrate is obtained from niraparib, e.g. as described in WO 2014/088983 or PCT/US2018/029131. An exemplary XRPD pattern for the niraparib tosylate monohydrate is shown in FIG. 1.

Niraparib Freebase

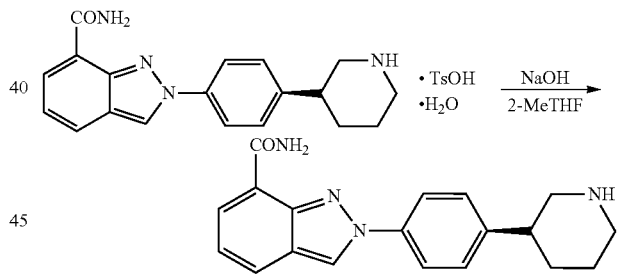

To a mixture of 50.0 g (97.9 mmol) niraparib tosylate monohydrate in 2-MeTHF (1 L) was added 1% NaOH solution (500 mL) at room temperature. After the mixture was stirred for 30 min., the aqueous layer was separated and extracted twice with 2-MeTHF (500 mL). The combined organic later was washed with water (1 L). The solution was concentrated under partial vacuum slowly below 30° C. to provide about 20 mL of suspension. The mixture was stirred for 30 min at room temperature and filtered to give an off-white solid (23.8 g, 75.9% yield). MS (ESI) $C_{19}H_{20}N_4O$ requires: 320, found: 321 [M+H]$^+$.

$^1$H NMR (500.12 MHz, DMSO-d$_6$) δ 9.27 (s, 1H), 8.59 (dd, 1H, J=1.8, 4.7 Hz), 8.07 (dd, 1H, J=1.1, 7.0 Hz), 8.04 (d, 2H, J=8.7 Hz), 8.02 (dd, 1H, J=1.1, 8.1 Hz), 7.90 (br. s, 1H), 7.46 (d, 2H, J=8.5 Hz), 7.27 (dd, 1H, J=7.2, 8.3 Hz), 3.00 (br. d, 1H, J=12.1 Hz), 2.94 (br. d, 1H, J=12.1 Hz), 2.70 (m, 1H), 2.51 (m, 2H), 1.91, (d, 1H, J=13.0 Hz), 1.68 (m, 1H), 1.61 (m, 1H), 1.49 (m, 1H).

$^{13}$C NMR (125.77 MHz, DMSO-d$_6$) δ 166.1, 146.5, 146.4, 138.0, 130.1, 128.7, 125.8, 123.9, 123.8, 122.3, 121.9, 121.1, 54.0, 46.4, 43.6, 40.6, 40.4, 40.3, 40.1, 39.9, 32.3, 27.0.

Example 1: Crystalline Niraparib Camphorate 1.1 Niraparib (1R,3S)-(+)-Camphorate (Form 1)—"(+)-Camphorate" Salt

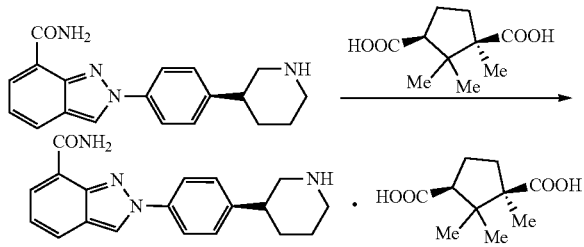

Niraparib free base (5 g, 15.6 mmol) was weighed into a vial followed by methanol (17.5 mL). After the addition of a solution of (1R,3S)-(+)-camphoric acid (16.4 mmol, 1.05 equiv.) in THF (16.4 mL), the resulting slurry was thermally cycled with agitation for 72 h (ambient conditions for 4 h then 40° C. for 4 h). Upon removal from the thermal cycle, the solid material present was isolated by centrifuge filtration, affording crude niraparib (1R,3S)-(+)-camphorate salt (5.69 g). Crude niraparib (1R,3S)-(+)-camphorate salt (5.24 g) and (1R,3S)-(+)-camphoric acid (4.0 g; 12.5 mmol; 0.8 equiv.) was slurried in methanol (200 mL) at 40° C. After stirring for approximately 0.5 hour, the batch was cooled down to room temperature and stirred for additional 24 hours. The resulting slurry was stored in a refrigerator for additional 24 hours before isolating the solids by filtration and drying the filtered solids in a vacuum oven at 40° C. for 3 h. This afforded niraparib (1R,3S)-(+)-camphorate salt (6.48 g, 75.0% overall yield) as a crystalline solid (m.p. 264° C.).

$^1$H NMR (500 MHz, DMSO-d$_6$) δ 9.28 (s, 1H), 8.57 (br. s, 1H), 8.07 (dt, 2H, J=1.9, 8.7 Hz), 8.06 (dd, 1H, J=1.0, 6.9 Hz), 8.02 (dd, 1H, J=1.0, 8.3 Hz), 7.89 (br. s, 1H), 7.49 (d, 2H, J=8.8 Hz), 7.27 (dd, 1H, J=7.1, 8.1 Hz), 3.11 (br. d, 1H, J=12.0 Hz), 3.06 (br. d, 1H, J=12.3 Hz), 2.80 (tt, 1H, J=3.5, 11.3 Hz), 2.75-2.56 (m, 3H), 2.39-2.27 (m, 1H), 2.05-1.88 (m, 2H), 1.79-1.54 (m, 4H), 1.41-1.32 (m, 1H), 1.18, (s, 3H), 1.11 (s, 3H), 0.80 (s, 3H).

FT-IR (cm$^{-1}$): 3359.44, 3182.612, 3120.66, 2980.97, 2964.28, 2886.27, 2860.66, 2701.37, 2513.23, 1692.94, 1648.76, 1557.44, 1523.02, 1434.04, 1396.55, 1377.75, 1331.85, 1304.91, 1264.73, 1229.82, 1203.47, 1156.66, 1127.69, 1091.44, 1060.29, 1001.87, 946.70, 871.18, 827.13, 794.09, 755.21, 717.77, 678.26, 615.99, 551.87, 535.68, 494.00, 463.87, 411.96. The IR spectrum of niraparib (1R,3S)-(+)-camphorate is shown in FIG. 2.

1.2 Niraparib (1S,3R)-(-)-Camphorate (Form 1) "(-)-Camphorate" Salt

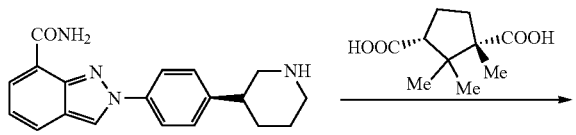

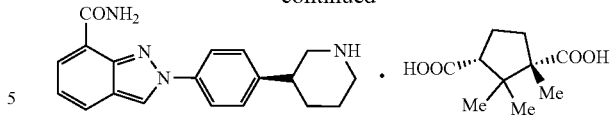

To a suspension of niraparib freebase (250 mg; 0.78 mmol) in ethanol (2.5 mL) was added a solution of (1S,3R)-(-)-camphoric acid in THF (1.58 mL, 1.0 M, 2.1 eq) slowly over 1 h at 40° C. The resulting solution was agitated for one hour at 40° C. The resulting suspension was cooled to room temperature over 1 h. The mixture was filtered and wet cake dried under vacuum at 40° C. for 3 h, to give niraparib (1S,3R)-(-)-camphorate (331 mg) as a crystalline solid (m.p. 226° C.).

$^1$H NMR (500 MHz, DMSO-d$_6$) δ 9.28 (s, 1H), 8.58 (br. s, 1H), 8.08 (dt, 2H, J=2.0, 8.6 Hz), 8.07 (dd, 1H, J=1.1, 7.0 Hz), 8.02 (dd, 1H, J=1.1, 8.3 Hz), 7.89 (br. s, 1H), 7.49 (d, 2H, J=8.6 Hz), 7.27 (dd, 1H, J=6.9, 8.2 Hz), 3.11 (br. d, 1H, J=11.9 Hz), 3.05 (br. d, 1H, J=12.5 Hz), 2.88-2.75 (m, 1H), 2.75-2.56 (m, 3H), 2.40-2.26 (m, 1H), 2.05-1.85 (m, 2H), 1.80-1.52 (m, 4H), 1.42-1.31 (m, 1H), 1.18 (s, 3H), 1.11 (s, 3H), 0.79 (s, 3H).

FT-IR (cm$^{-1}$): 3366.88, 3177.98, 3120.30, 3036.66, 2978.54, 2879.58, 2790.08, 2719.08, 2507.15, 2529.46, 2371.80, 2228.38, 2030.21, 1693.10, 1648.46, 1560.66, 1523.93, 1458.02, 1429.67, 1377.32, 1331.43, 1303.71, 1269.54, 1200.70, 1156.87, 1127.25, 1085.34, 1058.93, 1000.35, 932.27, 914.62, 869.18, 839.71, 794.24, 780.48, 753.71, 721.16, 673.17, 604.09, 543.75, 522.65, 487.43, 453.97, 409.48. The IR spectrum of niraparib (1S,3R)-(-)-camphorate is shown in FIG. 8.

Example 2: Crystalline Niraparib Mandelate

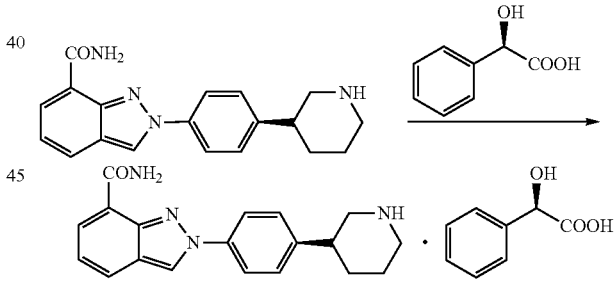

To a suspension 5.0 g (15.6 mmol) of niraparib free base in acetonitrile (100 mL) was added a solution of (R)-(-)-mandelic acid in THF (15.8 mL, 1.0 M, 1.05 eq.) as a bulk solution at room temperature. The resulting mixture was placed on a thermal cycle with agitation for 72 h at room temperature for 4 h followed by 40° C. for 4 h. The mixture was filtered at room temperature to give the title compound (5.9 g). Around the solid (5.5 g) was dissolved in of MeOH (80 mL) at 40° C. After cooling to room temperature, 10-20 mL of the solvent was allowed to evaporate. After 24 h, significant precipitation was observed. The suspension was stored in a fridge for a further 24 h before isolating the solids by filtration and drying the filtered solids in a vacuum oven at 40° C. for 3 h. This afforded the title salt (3.8 g, 50.6% overall yield) as a crystalline salt (m.p. 197° C.).

$^1$H NMR (500 MHz, DMSO-d$_6$) δ 9.30 (s, 1H), 8.58 (br. s, 1H), 8.10 (dt, 2H, J=1.9, 8.7 Hz), 8.08 (dd, 1H, J=1.1, 6.9

Hz), 8.02 (dd, 1H, J=1.1, 8.4 Hz), 7.90 (br. s, 1H), 7.48 (d, 2H, J=8.6 Hz), 7.41 (m, 2H), 7.27 (m, 3H), 7.17 (tt, 1H, J=1.9, 8.0 Hz), 4.65 (s, 1H), 3.30-3.19 (m, 2H), 3.00-2.90 (m, 2H), 2.87-2.76 (m, 1H), 1.90-1.64 (m, 4H).

FT-IR (cm$^{-1}$): 3443.90, 3340.48, 3150.83, 3030.33, 2982.99, 2939.97, 2621.21, 2513.33, 2442.51, 1671.47, 1637.65, 1584.33, 1524.97, 1433.06, 1465.81, 1369.51, 1320.36, 1263.54, 1204.03, 1186.23, 1142.43, 1098.65, 1062.22, 961.17, 905.79, 870.89, 828.56, 764.89, 730.97, 693.15, 674.78, 622.88, 591.13, 555.73, 536.97, 508.16, 455.43, 406.54. The IR spectrum of niraparib (R)-(−)-mandelate is shown in FIG. 14.

Example 3: Crystalline Niraparib Camsylate

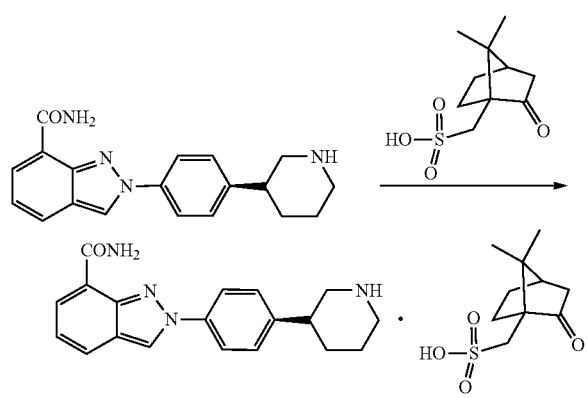

To a suspension of niraparib freebase (2.5 g; 7.8 mmol) in acetonitrile (100 mL) was added a solution of (1S)-(+)-camphor-10-sulfonic acid in THF (7.9 mL, 1.0 M, 1.05 eq.) as a bulk solution at room temperature. The mixture was placed on thermal cycle (4 h cycles between ambient temperature and 40° C.) with agitation. The solids were collected by filtration and fully dissolved in methanol (50 mL). Around 10 to 20 mL of the solvent in the resulting solution was allowed to evaporate very slowly over 24 h at room temperature. Precipitation was observed. The sample was placed in a fridge for a further 24 h. The mixture was filtered and wet cake dried in a vacuum oven, to give niraparib camsylate (1.6 g; 37% yield) as a crystalline solid (m.p. 239° C.).

$^{1}$H NMR (500 MHz, DMSO-d$_{6}$) δ 9.32 (s, 1H), 8.56 (br. s, 1H), 8.14 (dt, 2H, J=1.9, 8.7 Hz), 8.07 (dd, 1H, J=1.1, 7.0 Hz), 8.03 (dd, 1H, J=1.1, 8.4 Hz), 7.90 (br. s, 1H), 7.56 (d, 2H, J=8.6 Hz), 7.29 (dd, 1H, J=7.1, 8.4 Hz), 3.47-3.21 (m, 2H), 3.19-3.02 (m, 2H), 2.99-2.87 (m, 2H), 2.74-2.63 (m, 1H), 2.41 (d, 1H, J=14.7 Hz), 2.24 (dt, 1H, J=4.0, 18.0 Hz), 2.02-1.71 (m, 7H), 1.36-1.22 (m, 2H), 1.06 (s, 3H), 0.75 (s, 3H).

FT-IR (cm$^{-1}$): 3466.56, 3305.79, 3134.98, 2983.48, 2966.85, 2924.72, 2855.25, 2629.88, 2529.59, 2443.22, 1724.23, 1660.68, 1611.04, 1594.54, 1525.74, 1458.86, 1378.40, 1351.19, 1305.30, 1277.01, 1254.07, 1196.23, 1110.37, 1032.65, 941.09, 906.51, 867.55, 826.34, 784.10, 756.64, 717.04, 668.42, 689.10, 618.76, 599.80, 583.63, 558.36, 514.62, 497.92, 456.56, 432.40. The IR spectrum of niraparib camsylate is shown in FIG. 21.

Example 4: X-Ray Powder Diffraction (XRPD)

The XRPD patterns of the crystalline solids produced in Examples 1 to 3 are shown in FIGS. 3, 9, 15 and 22. The niraparib (R)-(−)-mandelate salt was ground up to produce a more homogeneous particle size prior to XRPD analysis. The crystalline form which is observed in each case is assigned as "Form 1".

Tables 1 to 4 below list XRPD diffraction angles from FIGS. 3, 8, 13 and 19, respectively.

TABLE 1

XRPD diffraction angles of niraparib (+)-camphorate (Form 1)

| No. | Pos. [°2θ] | d-spacing [Å] | Height [cts] | Area [cts*°2θ] | Rel. Int. [%] |
|---|---|---|---|---|---|
| 1 | 6.5108 | 13.57602 | 285.40 | 21.61 | 15.86 |
| 2 | 11.6932 | 7.56819 | 520.19 | 39.38 | 28.90 |
| 3 | 13.4174 | 6.59927 | 927.18 | 81.90 | 51.51 |
| 4 | 14.0869 | 6.28710 | 379.38 | 28.72 | 21.08 |
| 5 | 14.5365 | 6.09365 | 415.62 | 31.47 | 23.09 |
| 6 | 14.7742 | 5.99613 | 370.29 | 23.36 | 20.57 |
| 7 | 15.1598 | 5.84446 | 875.21 | 66.26 | 48.62 |
| 8 | 16.2399 | 5.45810 | 1799.92 | 158.99 | 100 |
| 9 | 17.5008 | 5.06762 | 1643.35 | 145.16 | 91.30 |
| 10 | 18.0220 | 4.92222 | 479.21 | 36.28 | 26.62 |
| 11 | 18.9334 | 4.68728 | 457.67 | 34.65 | 25.43 |
| 12 | 20.0059 | 4.43836 | 1077.80 | 108.80 | 59.88 |
| 13 | 20.3880 | 4.35602 | 741.58 | 74.86 | 41.20 |
| 14 | 21.5662 | 4.12064 | 630.48 | 55.69 | 35.03 |
| 15 | 22.2955 | 3.98747 | 284.47 | 25.13 | 15.80 |
| 16 | 22.7596 | 3.90720 | 468.11 | 53.16 | 26.01 |
| 17 | 23.9898 | 3.70955 | 545.92 | 62.00 | 30.33 |
| 18 | 24.4694 | 3.63793 | 244.65 | 15.44 | 13.59 |
| 19 | 26.9426 | 3.30934 | 312.85 | 23.69 | 17.38 |
| 20 | 27.6423 | 3.22714 | 322.41 | 48.82 | 17.91 |

TABLE 2

XRPD diffraction angles of niraparib (−)-camphorate (Form 1)

| No. | Pos. [°2θ] | d-spacing [Å] | Height [cts] | Area [cts*°2θ] | Rel. Int. [%] |
|---|---|---|---|---|---|
| 1 | 6.4886 | 13.62232 | 1269.34 | 80.09 | 16.69 |
| 2 | 11.6179 | 7.61708 | 1721.31 | 130.32 | 22.63 |
| 3 | 13.3941 | 6.61069 | 1462.27 | 147.62 | 19.23 |
| 4 | 13.9992 | 6.32629 | 852.61 | 64.55 | 11.21 |
| 5 | 14.5015 | 6.10829 | 972.94 | 73.66 | 12.79 |
| 6 | 15.0637 | 5.88155 | 3663.00 | 231.11 | 48.17 |
| 7 | 15.9946 | 5.54127 | 1322.07 | 66.73 | 17.38 |
| 8 | 16.1644 | 5.48344 | 3702.78 | 373.79 | 48.69 |
| 9 | 17.4476 | 5.08294 | 4636.38 | 468.04 | 60.97 |
| 10 | 18.8521 | 4.70732 | 1163.80 | 102.80 | 15.30 |
| 11 | 19.9303 | 4.45503 | 2265.25 | 228.68 | 29.79 |
| 12 | 20.1994 | 4.39628 | 2654.52 | 100.49 | 34.91 |
| 13 | 20.3162 | 4.37127 | 7604.79 | 767.7 | 100 |
| 14 | 21.4569 | 4.14138 | 832.09 | 84.00 | 10.94 |
| 15 | 21.8704 | 4.06400 | 838.11 | 84.61 | 11.02 |
| 16 | 22.1794 | 4.00809 | 1506.23 | 95.03 | 19.81 |
| 17 | 22.3371 | 3.98014 | 1545.52 | 156.02 | 20.32 |
| 18 | 23.8709 | 3.72776 | 1207.48 | 121.89 | 15.88 |
| 19 | 24.4013 | 3.64792 | 2383.46 | 240.61 | 31.34 |
| 20 | 26.8726 | 3.31780 | 1294.76 | 130.71 | 17.03 |

TABLE 3

XRPD diffraction angles of niraparib mandelate (Form 1)

| No. | Pos. [°2θ] | d-spacing [Å] | Height [cts] | Area [cts*°2θ] | Rel. Int. [%] |
|---|---|---|---|---|---|
| 1 | 4.2792 | 20.64949 | 818.36 | 41.31 | 22.32 |
| 2 | 8.3815 | 10.54960 | 988.52 | 37.42 | 26.97 |
| 3 | 8.5523 | 10.33926 | 2122.34 | 133.91 | 57.89 |
| 4 | 8.7258 | 10.13417 | 1771.69 | 89.43 | 48.33 |
| 5 | 12.3619 | 7.16024 | 636.88 | 32.15 | 17.37 |
| 6 | 13.6768 | 6.47469 | 1168.87 | 73.75 | 31.88 |

TABLE 3-continued

XRPD diffraction angles of niraparib mandelate (Form 1)

| No. | Pos. [°2θ] | d-spacing [Å] | Height [cts] | Area [cts*°2θ] | Rel. Int. [%] |
|---|---|---|---|---|---|
| 7 | 14.0556 | 6.30103 | 729.72 | 55.25 | 19.91 |
| 8 | 16.1037 | 5.50396 | 621.64 | 31.38 | 16.96 |
| 9 | 16.3561 | 5.41960 | 3636.38 | 275.32 | 99.19 |
| 10 | 17.4165 | 5.09195 | 2781.94 | 280.84 | 75.89 |
| 11 | 17.6061 | 5.03754 | 1925.96 | 121.52 | 52.54 |
| 12 | 18.3712 | 4.82943 | 1628.06 | 82.18 | 44.41 |
| 13 | 18.5106 | 4.79337 | 3665.91 | 277.55 | 100 |
| 14 | 21.5215 | 4.12909 | 811.84 | 102.44 | 22.15 |
| 15 | 25.1409 | 3.54227 | 1428.73 | 54.09 | 38.97 |
| 16 | 27.2835 | 3.26876 | 742.98 | 37.50 | 20.27 |
| 17 | 27.5713 | 3.23261 | 1315.55 | 82.09 | 35.89 |
| 18 | 27.6511 | 3.23147 | 694.58 | 43.34 | 18.95 |
| 19 | 28.0046 | 3.18356 | 825.99 | 103.08 | 22.53 |
| 20 | 28.6669 | 3.11151 | 907.58 | 75.51 | 24.76 |

TABLE 4

XRPD diffraction angles of niraparib camsylate (Form 1)

| No. | Pos. [°2θ] | d-spacing [Å] | Height [cts] | Area [cts*°2θ] | Rel. Int. [%] |
|---|---|---|---|---|---|
| 1 | 6.7400 | 13.11474 | 672.59 | 50.92 | 13.77 |
| 2 | 7.6851 | 11.50392 | 433.70 | 27.36 | 8.88 |
| 3 | 9.4756 | 9.33381 | 508.29 | 38.48 | 10.41 |
| 4 | 11.0949 | 7.97492 | 1085.66 | 95.90 | 22.23 |
| 5 | 13.5060 | 6.55616 | 2860.76 | 252.69 | 58.58 |
| 6 | 14.3332 | 6.17961 | 445.33 | 33.72 | 9.12 |
| 7 | 16.0270 | 5.53015 | 4883.43 | 492.98 | 100 |
| 8 | 16.3933 | 5.40738 | 994.88 | 100.43 | 20.37 |
| 9 | 16.7432 | 5.29516 | 931.07 | 82.24 | 19.07 |
| 10 | 16.9206 | 5.24004 | 476.19 | 36.05 | 9.75 |
| 11 | 17.6412 | 5.02758 | 2705.62 | 341.41 | 55.40 |
| 12 | 20.3314 | 4.36803 | 709.08 | 107.37 | 14.52 |
| 13 | 22.7905 | 3.90197 | 566.60 | 71.50 | 11.60 |
| 14 | 23.7383 | 3.74828 | 958.58 | 157.25 | 19.63 |
| 15 | 24.3037 | 3.66235 | 2315.28 | 321.37 | 47.41 |
| 16 | 24.6013 | 3.61871 | 2239.83 | 310.90 | 45.87 |
| 17 | 24.9551 | 3.56822 | 631.50 | 63.75 | 12.93 |
| 18 | 25.2364 | 3.52907 | 653.13 | 57.69 | 13.37 |
| 19 | 25.8321 | 3.44903 | 584.17 | 132.69 | 11.96 |
| 20 | 26.8066 | 3.32581 | 568.43 | 86.07 | 11.64 |

Example 5: Melting Characteristics

DSC was performed on the crystalline solids produced in Examples 1 to 3. The DSC thermograms can be found in FIGS. 5, 11, 18 and 24. Table 5 below lists parameters from those thermograms.

TABLE 5

| Niraparib Salt | Melting onset (° C.) | Melting point (° C.) | Endotherm (mJ/mg) |
|---|---|---|---|
| (+)-Camphorate | ~264 | ~268 | 242 |
| (−)-Camphorate | ~226 | ~230 | 90 |
| Mandelate | ~197 | ~201 | 114 |
| Camsylate | ~235 | ~246 | 83 |

Example 6: Hygroscopicity

GVS was performed on the crystalline solids produced in Examples 1and 3. DVS was performed on the crystalline solids produced in Example 2. The results are shown in FIGS. 6, 12, 19 and 25. Table 6 below summarizes the % mass increase observed at 90% RH for the samples. The camphorate and mandelate salts are not hygroscopic (<0.5% mass increase); the camsylate salt is slightly hygroscopic.

TABLE 6

| Niraparib Salt | % Mass increase |
|---|---|
| (+)-Camphorate | ~0.3 |
| (−)-Camphorate | ~0.2 |
| Mandelate | ~0.07 |
| Camsylate | ~1.3 |

Example 7: Storage Stability

A sample of each crystalline solid produced in Examples 1 to 3 above was stored at 40° C. and 75% RH for 24 hours, and was then analyzed by XRPD. All of the materials were unchanged after storage at 40° C./75% RH for 24 h.

Example 8: Single Crystal Structure of Niraparib (R)-(−)-Mandelate (Form 1)

SXRD analysis was conducted on an Agilent Technologies (Dual Source) SuperNova diffractometer using monochromated Cu Kα (λ=1.54184 Å) radiation. The diffractometer was fitted with an Oxford Cryosystems low temperature device to enable data collection to be performed at 120(1) K and the crystal encased in a protective layer of Paratone oil. The data collected were corrected for absorption effects based on Gaussian integration over a multifaceted crystal model, implemented as a part of the CrysAlisPro software package (Agilent Technologies, 2014).

The structure was solved by direct methods (SHELXS97)1 and developed by full least squares refinement on F2 (SHELXL97)1 interfaced via the OLEX2 software package. Images produced were done so via OLEX2.2 Data was collected, solved and refined in the orthorhombic space group P212121 and a search for higher metric symmetry using the ADDSYMM3 routine of PLATON4 but failed to uncover any higher order symmetry.

All non-hydrogen atoms were located in the Fourier map and their positions refined prior to describing their thermal movement of all non-hydrogen atoms anisotropically. Within the structure, one complete, crystallographically independent niraparib formula unit was found within the asymmetric unit, with associated mandelic acid formula unit of full stoichiometry. Within the structure, both the parent niraparib molecule and associated mandelic acid were found to be disordered across two positions, with occupancies of 50%. No further disorder was noted in the final structure. Within the disordered unit, the following distances were restrained to 1.54 Å with esd 0.01; C22A-C21 and C22B-C21.

All hydrogen atoms were placed in calculated positions using a riding model with fixed Uiso at 1.2 times for all CH, $CH_2$ and $NH_2$ groups, and 1.5 times for all OH groups. The highest residual Fourier peak was found to be 0.58 e.Å$^{-3}$ approx 0.30 Å from N2, and the deepest Fourier hole was found to be −0.37 e.Å$^{-3}$ approx. 1.55 Å from $N_2$.

Niraparib (R)-(−)-Mandelate Refinement Parameters

| Parameter | Value |
|---|---|
| Empirical formula | $C_{27}H_{28}N_4O_4$ |
| Formula weight | 472.53 |

-continued

| Parameter | Value |
|---|---|
| Temperature/K | 120(1) |
| Crystal system | orthorhombic |
| Space group | $P2_12_12_1$ |
| a/Å | 37.4885(14) |
| b/Å | 7.0805(3) |
| c/Å | 8.8782(4) |
| α/° | 90.00 |
| β/° | 90.00 |
| γ/° | 90.00 |
| Volume/Å$^3$ | 2356.59(17) |
| Z | 4 |
| $\rho_{calc}$g/cm$^3$ | 1.332 |
| μ/mm$^{-1}$ | 0.739 |
| F(000) | 1000.0 |
| Crystal size/mm$^3$ | 0.195 × 0.039 × 0.023 |
| Radiation | CuKα (λ = 1.54178) |
| 2Θ range for data collection/° | 9.44 to 155.08 |
| Index ranges | −47 ≤ h ≤ 46, −8 ≤ k ≤ 8, −11 ≤ l ≤ 9 |
| Reflections collected | 68572 |
| Independent reflections | 4889 [$R_{int}$ = 0.1302, $R_{sigma}$ = 0.0589] |
| Data/restraints/parameters | 4889/2/437 |
| Goodness-of-fit on F$^2$ | 1.072 |
| Final R indexes [I >= 2σ (I)] | $R_1$ = 0.0832, $wR_2$ = 0.2402 |
| Final R indexes [all data] | $R_1$ = 0.0943, $wR_2$ = 0.2542 |
| Largest diff. peak/hole/e Å$^{-3}$ | 0.58/−0.37 |
| Flack parameter | 0.1(5) |

Example 9: Light Microscopy

The crystalline solids produced in Examples 1 to 3 were assessed by light microscopy using visible and PLM. Micrographs are shown in FIGS. 7, 13, 20 and 26 and the results are summarised in Table 7 below.

TABLE 7

| Niraparib Salt | Nature | Size (of the order of) | Birefringent? |
|---|---|---|---|
| (+)-Camphorate (FIG. 7) | Aggregation of lath-likeparticles | 10 μm | Yes |
| (−)-Camphorate (FIG. 13) | Lath-like particles | 100 μm (some smaller particles observed) | Yes |
| Mandelate (FIG. 20) | Lath-like particles | 300 μm | Yes |
| Camsylate (FIG. 26) | Aggregation of lath-likeparticles | 10 μm (various sizes observed) | Yes |

Example 10: Solubility Study

The solubility of the crystalline solids produced in Examples 1.1, 2 and 3 above was compared to the solubility of crystalline niraparib tosylate monohydrate (as characterised by the XRPD pattern FIG. 1) using the following protocol:

In an initial procedure (performed in triplicate), the salts were added in small aliquots to deionised water or to buffer solutions (10 mL) until saturation was achieved (~20 mg was initially added), and the resulting slurry was shaken at 37° C. for 24 h. The following buffers (50 mM in each case) were used:

pH 1 25 mL KCl solution (1.49 g dissolved in 100 mL water) and 42.5 mL HCl solution (1.66 mL of concentrated HCl (~37%) made up to 100 mL with water) were added together and made up to 100 mL with water;

pH 4.5 anhydrous sodium acetate (1.07 g) was dissolved in water (about 150 mL) before adding 5.9 mL acetic acid solution (11.6 mL glacial acetic acid made up to 100 mL with water). The resulting solution was made up to 500 mL with water; and pH 6.8 25 mL of KH$_2$PO$_4$ solution (2.72 g dissolved in about 80 mL water and made up to 100 mL with water) and 11.2 mL of NaOH solution (800 mg of sodium hydroxide was dissolved and diluted to 100 mL with water) were added together and made up to 100 mL with water.

A further ~20 to 30 mg of the appropriate salt was added after the first hour to the following samples: (i) (1R,3S)-(+)-camphorate in pH 1 buffer; (ii) (R)-(−)-mandelate 1 in water, pH 1 buffer and pH 4.5 buffer; and (iii) (1S)-(+)-camsylate in all solvents.

Each sample was then filtered and the concentration of niraparib in the mother liquor was assessed by HPLC. Any solids which were isolated by filtration were assessed by XRPD to determine whether the form of the material had changed.

For those samples with a solubility of greater than 30 mg/ml, solutions were observed after the first 30 mg of the solids were added. The solubility assessment of these samples was repeated using the following procedure (samples prepared in triplicate):

The appropriate salt (30 mg) was weighed into a vial and water or buffer solution (1 mL) was added. The samples were shaken at 37° C. for 24 h. After 1 h and after about 17 h, further salt was added to the mandelate samples (except those in pH 1 buffer solution) to give an approximate 50-60 mg of solids. For the mandelate pH 1 samples further material was loaded until saturation was reached, when a biphasic system was observed. The samples were analysed as described above.

The solubility of the niraparib salts is shown in Table 8 below. In each case, the solubility value reported is the mean average of the triplicate measurements, based on the concentration of niraparib freebase in solution.

TABLE 8

| | Solubility (mg/mL) | | | |
|---|---|---|---|---|
| Niraparib Salt | pH 1 | pH 4.5 | pH 6.8 | Water |
| Tosylate | 0.9 | 0.6 | 0.9 | 0.5 |
| (+)-Camphorate | 21.4 | 0.3 | 1.2 | 0.2 |
| Mandelate | 163.1 | 53.8 | 7.8 | 45.4 |
| Camsylate | 11.5 | 7.1 | 1.7 | 5.9 |

The data in Table 8 suggest that camphorate, mandelate and camsylate salts have a greater solubility than the tosylate salt, especially in low pH media. The mandelate salt, in particular, displays a high solubility across a wide range of pH values, which is an advantageous property (and surprising, given its lack of hygroscopicity).

The teachings of all patents, published applications and references cited herein are incorporated by reference in their entirety.

While the present invention has particularly been shown and described with reference to exemplary embodiments thereof, it will be understood by those skilled in the art that various changes in form and details may be made therein without departing from the sprit and scope of the invention encompassed by the appended claims.

The invention claimed is:

1. A 2-{4-[(3S)-piperidin-3-yl]phenyl}-2H-indazole-7-carboxamide salt selected from the group consisting of:
2-{4-[(3S)-piperidin-3-yl]phenyl}-2H-indazole-7-carboxamide (1R,3S)-(+)-camphorate;
2-{4-[(3S)-piperidin-3-yl]phenyl}-2H-indazole-7-carboxamide (1S,3R)-(−)-camphorate;
2-{4-[(3S)-piperidin-3-yl]phenyl}-2H-indazole-7-carboxamide (R)-(−)-mandelate; and
2-{4-[(3S)-piperidin-3-yl]phenyl}-2H-indazole-7-carboxamide (1S)-(+)-camsylate;
wherein the salt is a crystalline form;
wherein the 2-{4-[(3S)-piperidin-3-yl]phenyl}-2H-indazole-7-carboxamide (1R,3S)-(+)-camphorate crystalline form is characterized by an X-ray powder diffraction (XRPD) pattern comprising at least three diffraction angles, when measured using Cu K radiation, selected from a group consisting of about 13.4, 15.2, 16.2, 17.5, 18.0, 20.0, 20.4, 21.6, and 24.0 degrees 2θ;
wherein the 2-{4-[(3S)-piperidin-3-yl]phenyl}-2H-indazole-7-carboxamide (1S,3R)-(−)-camphorate crystalline form is characterized by an X-ray powder diffraction (XRPD) pattern comprising at least three diffraction angles, when measuring using Cu K radiation, selected from a group consisting of about 11.6, 15.1, 16.2, 17.4, 19.9, 20.2, 20.3, 22.3, and 24.4 degrees 2θ;
wherein the 2-{4-[(3S)-piperidin-3-yl]phenyl}-2H-indazole-7-carboxamide (R)-(−)-mandelate crystalline form is characterized by an X-ray powder diffraction (XRPD) pattern comprising at least three diffraction angles, when measured using Cu K radiation, selected from a group consisting of about 8.6, 8.7, 13.7, 16.4, 17.4, 18.4, 18.5, 21.5, 25.1, 27.3, 27.6, 28.0, and 28.7 degrees 2θ; and
wherein the 2-{4-[(3S)-piperidin-3-yl]phenyl}-2H-indazole-7-carboxamide (1S)-(+)-camsylate crystalline form is characterized by an X-ray powder diffraction (XRPD) pattern comprising at least three diffraction angles, when measured using Cu K radiation, selected from a group consisting of about 11.1, 13.5, 16.0, 16.4, 16.7, 17.6, 20.3, 23.7, 24.3, and 24.6 degrees 2θ.

2. The 2-{4-[(3S)-piperidin-3-yl]phenyl}-2H-indazole-7-carboxamide salt according to claim 1, wherein the salt is 2-{4-[(3S)-piperidin-3-yl]phenyl}-2H-indazole-7-carboxamide (1R,3S)-(+)-camphorate.

3. The 2-{4-[(3S)-piperidin-3-yl]phenyl}-2H-indazole-7-carboxamide salt according to claim 2, wherein the 2-{4-[(3S)-piperidin-3-yl]phenyl}-2H-indazole-7-carboxamide (1R,3S)-(+)-camphorate crystalline form is characterized by an X-ray powder diffraction (XRPD) pattern substantially in accordance with FIG. 3.

4. The 2-{4-[(3S)-piperidin-3-yl]phenyl}-2H-indazole-7-carboxamide salt according to claim 1, wherein the salt is 2-{4-[(3S)-piperidin-3-yl]phenyl}-2H-indazole-7-carboxamide (1S,3R)-(−)-camphorate.

5. The 2-{4-[(3S)-piperidin-3-yl]phenyl}-2H-indazole-7-carboxamide salt according to claim 4, wherein the 2-{4-[(3S)-piperidin-3-yl]phenyl}-2H-indazole-7-carboxamide (1S,3R)-(−)-camphorate crystalline form is characterized by an X-ray powder diffraction (XRPD) pattern substantially in accordance with FIG. 9.

6. The 2-{4-[(3S)-piperidin-3-yl]phenyl}-2H-indazole-7-carboxamide salt according to claim 1, wherein the salt is 2-{4-[(3S)-piperidin-3-yl]phenyl}-2H-indazole-7-carboxamide (R)-(−)-mandelate.

7. The 2-{4-[(3S)-piperidin-3-yl]phenyl}-2H-indazole-7-carboxamide salt according to claim 6, wherein the 2-{4-[(3S)-piperidin-3-yl]phenyl}-2H-indazole-7-carboxamide (R)-(−)-mandelate crystalline form is characterized by an X-ray powder diffraction (XRPD) pattern substantially in accordance with FIG. 15.

8. The 2-{4-[(3S)-piperidin-3-yl]phenyl}-2H-indazole-7-carboxamide salt according to claim 1, wherein the salt is 2-{4-[(3S)-piperidin-3-yl]phenyl}-2H-indazole-7-carboxamide (1S)-(+)-camsylate.

9. The 2-{4-[(3S)-piperidin-3-yl]phenyl}-2H-indazole-7-carboxamide salt according to claim 8, wherein the 2-{4-[(3S)-piperidin-3-yl]phenyl}-2H-indazole-7-carboxamide (1S)-(+)-camsylate crystalline form is characterized by an X-ray powder diffraction (XRPD) pattern substantially in accordance with FIG. 22.

10. A pharmaceutical composition comprising the 2-{4-[(3S)-piperidin-3-yl]phenyl}-2H-indazole-7-carboxamide salt according to claim 1, and at least one pharmaceutically acceptable excipient.

11. The pharmaceutical composition according to claim 10, wherein the pharmaceutical composition is adapted for oral administration.

12. A method of treating epithelial ovarian cancer, fallopian tube cancer, primary peritoneal cancer, stroke, autoimmune diabetes, or a cardiovascular disease in a human in need thereof, the method comprising administering to the human an effective amount of the 2-{4-[(3S)-piperidin-3-yl]phenyl}-2H-indazole-7-carboxamide salt according to claim 1.

13. The method according to claim 12, wherein said method is a method of treating stroke, autoimmune diabetes, or a cardiovascular disease.

14. The method according to claim 13, wherein said cancer is associated with a mutation in ATM, ATR, BAP1, BARD1, BLM, BRCA1, BRCA2, BRIP1, MRE11A, NBN, PALB2, RAD51, RAD51B, RAD51C, RAD51D, RAD52, RAD54L, or XRCC2, or any combination thereof.

15. The method according to claim 12, wherein said method is a method of treating epithelial ovarian cancer, fallopian tube cancer, or primary peritoneal cancer.

* * * * *

UNITED STATES PATENT AND TRADEMARK OFFICE
CERTIFICATE OF CORRECTION

PATENT NO. : 12,297,184 B2
APPLICATION NO. : 17/282344
DATED : May 13, 2025
INVENTOR(S) : Alistair James Stewart et al.

It is certified that error appears in the above-identified patent and that said Letters Patent is hereby corrected as shown below:

On the Title Page

Item (60), (Related Application Data), Delete "62/740,869," and insert -- 62/740,872, --.

Signed and Sealed this
First Day of July, 2025

Coke Morgan Stewart
*Acting Director of the United States Patent and Trademark Office*